United States Patent
Wells et al.

(10) Patent No.: US 10,781,425 B2
(45) Date of Patent: *Sep. 22, 2020

(54) METHODS AND SYSTEMS FOR CONVERTING PRECURSOR CELLS INTO INTESTINAL TISSUES THROUGH DIRECTED DIFFERENTIATION

(71) Applicant: Children's Hospital Medical Center, Cincinnati, OH (US)

(72) Inventors: James M. Wells, Cincinnati, OH (US); Aaron M. Zorn, Cincinnati, OH (US); Jason R. Spence, Ann Arbor, MI (US); Noah F. Shroyer, Houston, TX (US)

(73) Assignee: Children's Hospital Medical Center, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/627,588

(22) Filed: Jun. 20, 2017

(65) Prior Publication Data
US 2017/0362573 A1    Dec. 21, 2017

Related U.S. Application Data

(63) Continuation of application No. 13/695,887, filed as application No. PCT/US2011/035518 on May 6, 2011, now Pat. No. 9,719,068.

(60) Provisional application No. 61/332,178, filed on May 6, 2010.

(51) Int. Cl.
*C12N 5/071* (2010.01)
*C12N 5/077* (2010.01)

(52) U.S. Cl.
CPC ......... *C12N 5/0679* (2013.01); *C12N 5/0661* (2013.01); *C12N 2501/119* (2013.01); *C12N 2501/155* (2013.01); *C12N 2501/16* (2013.01); *C12N 2501/385* (2013.01); *C12N 2501/415* (2013.01); *C12N 2502/02* (2013.01); *C12N 2502/45* (2013.01)

(58) Field of Classification Search
CPC .................................................. C12N 5/0679
See application file for complete search history.

(56) References Cited

U.S. PATENT DOCUMENTS

| | | |
|---|---|---|
| 5,942,435 A | 8/1999 | Wheeler |
| 6,607,501 B2 | 8/2003 | Gorsuch |
| 7,160,719 B2 | 1/2007 | Nyberg |
| 7,291,626 B1 | 11/2007 | Beachy et al. |
| 7,326,572 B2 | 2/2008 | Fisk et al. |
| 7,510,876 B2 | 3/2009 | D'Amour et al. |
| 7,541,185 B2 | 6/2009 | D'Amour et al. |
| 7,625,753 B2 | 12/2009 | Kelly et al. |
| 7,695,958 B2 | 4/2010 | Funatsu et al. |
| 7,704,738 B2 | 4/2010 | D'Amour et al. |
| 7,776,592 B2 | 8/2010 | Wandinger-Ness et al. |
| 7,985,585 B2 | 7/2011 | D'Amour et al. |
| 7,993,916 B2 | 8/2011 | Agulnick et al. |
| 8,187,878 B2 | 5/2012 | Dalton et al. |
| 8,216,836 B2 | 7/2012 | D'Amour et al. |
| 8,298,822 B2 | 10/2012 | Kruse et al. |
| 8,318,492 B2 | 11/2012 | Choo et al. |
| 8,501,476 B2 | 8/2013 | Morgan et al. |
| 8,586,357 B2 | 11/2013 | D'Amour et al. |
| 8,603,809 B2 | 12/2013 | Kruse |
| 8,609,406 B2 | 12/2013 | Subramanian et al. |
| 8,609,413 B2 | 12/2013 | Suter et al. |
| 8,632,645 B2 | 1/2014 | D'Amour et al. |
| 8,633,024 B2 | 1/2014 | D'Amour et al. |
| 8,642,339 B2 | 2/2014 | Sato et al. |
| 8,647,873 B2 | 2/2014 | D'Amour et al. |
| 8,658,151 B2 | 2/2014 | Kelly et al. |
| 8,685,386 B2 | 4/2014 | West et al. |
| 8,685,730 B2 | 4/2014 | Odorico et al. |
| 8,758,323 B2 | 6/2014 | Michaud et al. |
| 9,127,254 B2 | 9/2015 | Cohen et al. |
| 9,133,439 B2 | 9/2015 | Davis et al. |
| 9,181,301 B2 | 11/2015 | Carlson et al. |
| 9,200,258 B2 | 12/2015 | Mezghanni et al. |
| 9,206,393 B2 | 12/2015 | Kruse |
| 9,234,170 B2 | 1/2016 | Snoeck et al. |
| 9,334,479 B2 | 5/2016 | Herrera Sanchez et al. |
| 9,375,514 B2 | 6/2016 | Kruse et al. |
| 9,381,181 B2 | 7/2016 | Roberts et al. |
| 9,394,522 B2 | 7/2016 | Brolen et al. |

(Continued)

FOREIGN PATENT DOCUMENTS

| | | |
|---|---|---|
| CN | 103154237 A | 6/2013 |
| CN | 103561751 A | 2/2014 |

(Continued)

OTHER PUBLICATIONS

Spence et al. (2011, Nature, vol. 470, pp. 105-110) (Year: 2011).*

(Continued)

*Primary Examiner* — Thaian N. Ton
*Assistant Examiner* — David A. Montanari
(74) *Attorney, Agent, or Firm* — Knobbe, Martens, Olson & Bear, LLP

(57) ABSTRACT

The generation of complex organ tissues from human embryonic and pluripotent stem cells (PSCs) remains a major challenge for translational studies. It is shown that PSCs can be directed to differentiate into intestinal tissue in vitro by modulating the combinatorial activities of several signaling pathways in a step-wise fashion, effectively recapitulating in vivo fetal intestinal development. The resulting intestinal "organoids" were three-dimensional structures consisting of a polarized, columnar epithelium surrounded by mesenchyme that included a smooth muscle-like layer. The epithelium was patterned into crypt-like SOX9-positive proliferative zones and villus-like structures with all of the major functional cell types of the intestine. The culture system is used to demonstrate that expression of NEUROG3, a pro-endocrine transcription factor mutated in enteric anendocrinosis is sufficient to promote differentiation towards the enteroendocrine cell lineage. In conclusion, PSC-derived human intestinal tissue should allow for unprecedented studies of human intestinal development, homeostasis and disease.

14 Claims, 26 Drawing Sheets

(56) References Cited

U.S. PATENT DOCUMENTS

| | | |
|---|---|---|
| 9,446,076 B2 | 9/2016 | Gaussin et al. |
| 9,447,380 B2 | 9/2016 | Subramanian et al. |
| 9,476,030 B2 | 10/2016 | Gadue et al. |
| 9,499,795 B2 | 11/2016 | D'Amour et al. |
| 9,605,243 B2 | 3/2017 | D'Amour et al. |
| 9,616,039 B2 | 4/2017 | Roberts et al. |
| 9,618,500 B2 | 4/2017 | Giselbrecht et al. |
| 9,650,609 B2 | 5/2017 | Nyberg |
| 9,675,646 B2 | 6/2017 | Bitar |
| 9,677,085 B2 | 6/2017 | Guye et al. |
| 9,719,067 B2 | 8/2017 | Snoeck et al. |
| 9,719,068 B2 | 8/2017 | Wells et al. |
| 9,732,116 B2 | 8/2017 | Steiner et al. |
| 9,763,964 B2 | 9/2017 | Pellicciari et al. |
| 9,765,301 B2 | 9/2017 | Huch Ortega et al. |
| 9,771,562 B2 | 9/2017 | Shen et al. |
| 9,790,470 B2 | 10/2017 | Vallier et al. |
| 9,828,583 B2 | 11/2017 | Rauagopal et al. |
| 9,849,104 B2 | 12/2017 | Bisgaier et al. |
| 9,850,461 B2 | 12/2017 | Rizzi et al. |
| 9,856,458 B2 | 1/2018 | Rosowski et al. |
| 9,878,005 B2 | 1/2018 | Johns et al. |
| 9,914,920 B2 | 3/2018 | Goodwin et al. |
| 9,926,532 B2 | 3/2018 | Esteban et al. |
| 9,938,499 B2 | 4/2018 | Slukvin et al. |
| 10,130,748 B2 | 11/2018 | Nyberg et al. |
| 10,220,386 B2 | 3/2019 | Williamson et al. |
| 10,265,453 B2 | 4/2019 | Flieg et al. |
| 2003/0129751 A1 | 7/2003 | Grikscheit et al. |
| 2005/0266554 A1 | 12/2005 | D'Amour et al. |
| 2006/0236415 A1 | 10/2006 | Silversides et al. |
| 2007/0238169 A1 | 10/2007 | Abilez et al. |
| 2007/0239083 A1 | 10/2007 | Voss |
| 2009/0263357 A1 | 10/2009 | Sayre et al. |
| 2010/0075295 A1 | 3/2010 | Dryden et al. |
| 2010/0151568 A1 | 6/2010 | D'Amour et al. |
| 2011/0151564 A1 | 6/2011 | Menu et al. |
| 2011/0218512 A1 | 9/2011 | Tullis et al. |
| 2012/0071451 A1 | 3/2012 | Spenard et al. |
| 2012/0135519 A1 | 5/2012 | Ameri et al. |
| 2012/0196312 A1 | 8/2012 | Sato et al. |
| 2013/0031645 A1 | 1/2013 | Touboul et al. |
| 2013/0115673 A1 | 5/2013 | West et al. |
| 2013/0316442 A1 | 11/2013 | Meurville et al. |
| 2014/0038279 A1 | 2/2014 | Ingber et al. |
| 2014/0044713 A1 | 2/2014 | De Lau et al. |
| 2014/0193905 A1 | 7/2014 | Kelly et al. |
| 2014/0212910 A1 | 7/2014 | Bhatia et al. |
| 2014/0243227 A1 | 8/2014 | Clevers et al. |
| 2014/0273210 A1 | 9/2014 | Baker et al. |
| 2014/0302491 A1 | 10/2014 | Nadauld et al. |
| 2014/0308695 A1 | 10/2014 | Bruce et al. |
| 2014/0336282 A1 | 11/2014 | Ewald et al. |
| 2015/0017140 A1 | 1/2015 | Bhatia et al. |
| 2015/0197802 A1 | 7/2015 | Zink et al. |
| 2015/0201588 A1 | 7/2015 | Kamb et al. |
| 2015/0238656 A1 | 8/2015 | Orlando et al. |
| 2015/0330970 A1 | 11/2015 | Knoblich et al. |
| 2015/0343018 A1 | 12/2015 | Sansonetti et al. |
| 2015/0361393 A1 | 12/2015 | Nicholas et al. |
| 2016/0002602 A1 | 1/2016 | Almeida-Porada et al. |
| 2016/0022873 A1 | 1/2016 | Besner et al. |
| 2016/0060707 A1 | 3/2016 | Goldenberg et al. |
| 2016/0068805 A1 | 3/2016 | Martin et al. |
| 2016/0101133 A1 | 4/2016 | Basu et al. |
| 2016/0102289 A1 | 4/2016 | Yu et al. |
| 2016/0121023 A1 | 5/2016 | Edelman et al. |
| 2016/0122722 A1 | 5/2016 | Ejiri et al. |
| 2016/0143949 A1 | 5/2016 | Ingber et al. |
| 2016/0177270 A1 | 6/2016 | Takebe et al. |
| 2016/0184387 A1 | 6/2016 | Charmot et al. |
| 2016/0206664 A1 | 7/2016 | Sokal et al. |
| 2016/0237400 A1 | 8/2016 | Xian |
| 2016/0237401 A1 | 8/2016 | Vallier et al. |
| 2016/0237409 A1 | 8/2016 | Little et al. |
| 2016/0245653 A1 | 8/2016 | Park et al. |
| 2016/0256672 A1 | 9/2016 | Arumugaswami et al. |
| 2016/0257937 A1 | 9/2016 | Wauthier et al. |
| 2016/0263098 A1 | 9/2016 | Mantzoros |
| 2016/0289635 A1 | 10/2016 | Sasai et al. |
| 2016/0312181 A1 | 10/2016 | Freed et al. |
| 2016/0312190 A1 | 10/2016 | Ghaedi et al. |
| 2016/0312191 A1 | 10/2016 | Spence et al. |
| 2016/0319240 A1 | 11/2016 | Chan et al. |
| 2016/0340645 A1 | 11/2016 | D'Amour et al. |
| 2016/0340749 A1 | 11/2016 | Stelzer et al. |
| 2016/0354408 A1 | 12/2016 | Hariri et al. |
| 2016/0361466 A1 | 12/2016 | Yanagawa et al. |
| 2016/0376557 A1 | 12/2016 | Dubart Kupperschmitt et al. |
| 2017/0002330 A1 | 1/2017 | Vunjak-Novakovic et al. |
| 2017/0027994 A1 | 2/2017 | Kotton et al. |
| 2017/0035661 A1 | 2/2017 | Kyrkanides et al. |
| 2017/0035784 A1 | 2/2017 | Lancaster et al. |
| 2017/0037043 A1 | 2/2017 | Liu |
| 2017/0067014 A1 | 3/2017 | Takebe et al. |
| 2017/0101628 A1 | 4/2017 | Ingber et al. |
| 2017/0107469 A1 | 4/2017 | Costa et al. |
| 2017/0107483 A1 | 4/2017 | Pendergraft et al. |
| 2017/0107498 A1 | 4/2017 | Sareen et al. |
| 2017/0128625 A1 | 5/2017 | Bhatia et al. |
| 2017/0151049 A1 | 6/2017 | La Francesca et al. |
| 2017/0152486 A1 | 6/2017 | Shen et al. |
| 2017/0152528 A1 | 6/2017 | Zhang |
| 2017/0184569 A1 | 6/2017 | Keshavarzian et al. |
| 2017/0191030 A1 | 7/2017 | Huch Ortega et al. |
| 2017/0198261 A1 | 7/2017 | Sabaawy et al. |
| 2017/0204375 A1 | 7/2017 | Accili et al. |
| 2017/0205396 A1 | 7/2017 | Izpisua Belmonte et al. |
| 2017/0205398 A1 | 7/2017 | Bruce et al. |
| 2017/0239262 A1 | 8/2017 | Lefebvre |
| 2017/0240863 A1 | 8/2017 | Sokal et al. |
| 2017/0240964 A1 | 8/2017 | Leung et al. |
| 2017/0258772 A1 | 9/2017 | Sabatini et al. |
| 2017/0260501 A1 | 9/2017 | Semechkin et al. |
| 2017/0266145 A1 | 9/2017 | Nahmias et al. |
| 2017/0267970 A1 | 9/2017 | Gupta et al. |
| 2017/0267977 A1 | 9/2017 | Huang et al. |
| 2017/0275592 A1 | 9/2017 | Sachs et al. |
| 2017/0285002 A1 | 10/2017 | Taniguchi et al. |
| 2017/0296621 A1 | 10/2017 | Sansonetti et al. |
| 2017/0304294 A1 | 10/2017 | Wu et al. |
| 2017/0304369 A1 | 10/2017 | Ang et al. |
| 2017/0319548 A1 | 11/2017 | Lefebvre |
| 2017/0321188 A1 | 11/2017 | Viczian et al. |
| 2017/0321191 A1 | 11/2017 | Kojima |
| 2017/0335283 A1 | 11/2017 | Wang et al. |
| 2017/0342385 A1 | 11/2017 | Sachs et al. |
| 2017/0348433 A1 | 12/2017 | Kay et al. |
| 2017/0349659 A1 | 12/2017 | Garcia et al. |
| 2017/0349884 A1 | 12/2017 | Karp et al. |
| 2017/0360962 A1 | 12/2017 | Kay et al. |
| 2018/0021341 A1 | 1/2018 | Harriman et al. |
| 2018/0030409 A1 | 2/2018 | Lewis et al. |
| 2018/0042970 A1 | 2/2018 | Rossen et al. |
| 2018/0059119 A1 | 3/2018 | Takats et al. |
| 2019/0078055 A1 | 3/2019 | Wells et al. |
| 2019/0153397 A1 | 5/2019 | Wells et al. |
| 2019/0298775 A1 | 10/2019 | Takebe et al. |
| 2019/0314387 A1 | 10/2019 | Takebe et al. |
| 2019/0367882 A1 | 12/2019 | Wells et al. |

FOREIGN PATENT DOCUMENTS

| | | |
|---|---|---|
| CN | 105985395 A | 10/2016 |
| EP | 3228306 A1 | 10/2017 |
| JP | 2003-521673 A | 7/2003 |
| JP | 2008-503203 A | 2/2008 |
| JP | 2008-505638 A | 2/2008 |
| JP | 2013-066414 A | 4/2013 |
| KR | 10-2006-0114355 A | 11/2006 |
| WO | WO 92/07615 | 5/1992 |
| WO | WO 98/21312 | 5/1998 |
| WO | WO 2003/082201 A2 | 10/2003 |
| WO | WO 2005/001072 A1 | 1/2005 |

(56) References Cited

FOREIGN PATENT DOCUMENTS

| | | |
|---|---|---|
| WO | WO 2005/081970 A2 | 9/2005 |
| WO | WO 2005/097974 A2 | 10/2005 |
| WO | WO 2005/113747 A2 | 12/2005 |
| WO | WO 2006/126236 A1 | 11/2006 |
| WO | WO 2008/075339 A2 | 6/2008 |
| WO | WO 2009/022907 A2 | 2/2009 |
| WO | WO 2009/146911 A2 | 12/2009 |
| WO | WO 2010/008905 A2 | 1/2010 |
| WO | WO 2010/090513 A2 | 8/2010 |
| WO | WO 2010/094694 A1 | 8/2010 |
| WO | WO 2010/127399 A1 | 11/2010 |
| WO | WO 2010/143747 A1 | 12/2010 |
| WO | WO 2011/139628 A1 | 11/2011 |
| WO | WO 2011/140441 A2 | 11/2011 |
| WO | WO 2012/014076 A2 | 2/2012 |
| WO | WO 2012/027474 A1 | 3/2012 |
| WO | WO 0212/089669 A1 | 7/2012 |
| WO | WO 2012/118799 A2 | 9/2012 |
| WO | WO 2012/154834 A1 | 11/2012 |
| WO | WO 2012/155110 A1 | 11/2012 |
| WO | WO 2012/166903 A1 | 12/2012 |
| WO | WO 2012/168930 A2 | 12/2012 |
| WO | WO 2012/178215 A1 | 12/2012 |
| WO | WO 2013/040087 A2 | 3/2013 |
| WO | WO 2013/067498 A1 | 5/2013 |
| WO | WO 2013/086486 A1 | 6/2013 |
| WO | WO 2013/086502 A1 | 6/2013 |
| WO | WO 2013/093812 A2 | 6/2013 |
| WO | WO 2013/096741 A2 | 6/2013 |
| WO | WO 2013/127921 A1 | 6/2013 |
| WO | WO 2013/155060 A1 | 10/2013 |
| WO | WO 2013/174794 A1 | 11/2013 |
| WO | WO 2013/192290 A1 | 12/2013 |
| WO | WO 2014/013334 A2 | 1/2014 |
| WO | WO 2014/048637 A1 | 4/2014 |
| WO | WO 2014/053596 A1 | 4/2014 |
| WO | WO 2014/082096 A1 | 5/2014 |
| WO | WO 2014/090993 A1 | 6/2014 |
| WO | WO 2014/127170 A1 | 8/2014 |
| WO | WO 2014/151921 A1 | 9/2014 |
| WO | WO 2014/153230 A1 | 9/2014 |
| WO | WO 2014/153294 A1 | 9/2014 |
| WO | WO 2014/159356 | 10/2014 |
| WO | WO 2014/173907 A1 | 10/2014 |
| WO | WO 2014/182885 A2 | 11/2014 |
| WO | WO 2014/197934 A1 | 12/2014 |
| WO | WO 2014/199622 A1 | 12/2014 |
| WO | WO 2015/021358 A2 | 2/2015 |
| WO | WO 2015/060790 A1 | 4/2015 |
| WO | WO 2015/075175 A1 | 5/2015 |
| WO | WO 2015/076388 A1 | 5/2015 |
| WO | WO 2015/108893 A1 | 7/2015 |
| WO | WO 2015/123183 A1 | 8/2015 |
| WO | WO 2015/129822 A1 | 9/2015 |
| WO | WO 2015/130919 A1 | 9/2015 |
| WO | WO 2015/135893 A1 | 9/2015 |
| WO | WO 2015/138032 A2 | 9/2015 |
| WO | WO 2015/152954 A1 | 10/2015 |
| WO | WO 2015/156929 A1 | 10/2015 |
| WO | WO 2015/157163 A1 | 10/2015 |
| WO | WO 2015/168022 A1 | 11/2015 |
| WO | WO 2015/0173425 A1 | 11/2015 |
| WO | WO 2015/183920 A2 | 12/2015 |
| WO | WO 2015/184273 A1 | 12/2015 |
| WO | WO 2015/184375 A2 | 12/2015 |
| WO | WO 2015/185714 A1 | 12/2015 |
| WO | WO 2015/196012 A1 | 12/2015 |
| WO | WO 2015/200901 A1 | 12/2015 |
| WO | WO 2016/011377 | 1/2016 |
| WO | WO 2016/015158 | 2/2016 |
| WO | WO 2016/030525 A1 | 3/2016 |
| WO | WO 2016/033163 A1 | 3/2016 |
| WO | WO 2016/057571 A1 | 4/2016 |
| WO | WO 2016/061464 A1 | 4/2016 |
| WO | WO 2016/073989 A2 | 5/2016 |
| WO | WO 2016/083612 A1 | 6/2016 |
| WO | WO 2016/083613 A2 | 6/2016 |
| WO | WO 2016/085765 A1 | 6/2016 |
| WO | WO 2016/094948 A1 | 6/2016 |
| WO | WO 2016/103002 A1 | 6/2016 |
| WO | WO 2016/103269 A1 | 6/2016 |
| WO | WO 2016/121512 A1 | 8/2016 |
| WO | WO 2016/140716 A1 | 9/2016 |
| WO | WO 2016/141137 A1 | 9/2016 |
| WO | WO 2016/144769 A1 | 9/2016 |
| WO | WO 2016/164413 A1 | 10/2016 |
| WO | WO 2016/168950 A1 | 10/2016 |
| WO | WO 2016/174604 A1 | 11/2016 |
| WO | WO 2016/176208 A1 | 11/2016 |
| WO | WO 2016/183143 A1 | 11/2016 |
| WO | WO 2016/193441 A2 | 12/2016 |
| WO | WO 2016/207621 A1 | 12/2016 |
| WO | WO 2016/210313 A1 | 12/2016 |
| WO | WO 2016/210416 | 12/2016 |
| WO | WO 2017/009263 A1 | 1/2017 |
| WO | WO 2017/036533 | 3/2017 |
| WO | WO 2017/037295 A1 | 3/2017 |
| WO | WO 2017/041041 A1 | 3/2017 |
| WO | WO 2017/048193 A1 | 3/2017 |
| WO | WO 2017/048322 | 3/2017 |
| WO | WO 2017/049243 A1 | 3/2017 |
| WO | WO 2017/059171 A1 | 4/2017 |
| WO | WO 2017/060884 A1 | 4/2017 |
| WO | WO 2017/066507 A1 | 4/2017 |
| WO | WO 2017/066659 | 4/2017 |
| WO | WO 2017/070007 A2 | 4/2017 |
| WO | WO 2017/070224 A1 | 4/2017 |
| WO | WO 2017/070471 A1 | 4/2017 |
| WO | WO 2017/070506 A1 | 4/2017 |
| WO | WO 2017/075389 A1 | 5/2017 |
| WO | WO 2017/077535 A1 | 5/2017 |
| WO | WO 2017/079632 A1 | 5/2017 |
| WO | WO 2017/083705 A1 | 5/2017 |
| WO | WO 2017/096192 A1 | 6/2017 |
| WO | WO 2017/096282 A1 | 6/2017 |
| WO | WO 2017/112901 A1 | 6/2017 |
| WO | WO 2017/115982 A1 | 7/2017 |
| WO | WO 2017/117333 A1 | 7/2017 |
| WO | WO 2017/117547 A1 | 7/2017 |
| WO | WO 2017/117571 A1 | 7/2017 |
| WO | WO 2017/120543 A1 | 7/2017 |
| WO | WO 2017/121754 A1 | 7/2017 |
| WO | WO 2017/123791 A1 | 7/2017 |
| WO | WO 2017/136462 | 8/2017 |
| WO | WO 2017/136479 A1 | 8/2017 |
| WO | WO 2017/139455 A1 | 8/2017 |
| WO | WO 2017/139638 A1 | 8/2017 |
| WO | WO 2017/142069 A1 | 8/2017 |
| WO | WO 2017/143100 A1 | 8/2017 |
| WO | WO 2017/149025 A1 | 9/2017 |
| WO | WO 2017/153992 A1 | 9/2017 |
| WO | WO 2017/160234 A1 | 9/2017 |
| WO | WO 2017/160671 A1 | 9/2017 |
| WO | WO 2017/172638 A1 | 10/2017 |
| WO | WO 2017/174609 A1 | 10/2017 |
| WO | WO 2017/176810 A1 | 10/2017 |
| WO | WO 2017/184586 | 10/2017 |
| WO | WO 2017/192997 | 11/2017 |
| WO | WO 2017/205511 A1 | 11/2017 |
| WO | WO 2017/218287 A1 | 12/2017 |
| WO | WO 2017/220586 A1 | 12/2017 |
| WO | WO 2018/011558 A1 | 1/2018 |
| WO | WO 2018/019704 A1 | 2/2018 |
| WO | WO 2018/026947 A1 | 2/2018 |
| WO | WO 2018/027023 A1 | 2/2018 |
| WO | WO 2018/027112 A1 | 2/2018 |
| WO | WO 2018/035574 A1 | 3/2018 |
| WO | WO 2018/038042 A1 | 3/2018 |
| WO | WO 2018/044685 A1 | 3/2018 |
| WO | WO 2018/044885 A1 | 3/2018 |
| WO | WO 2018/044937 A2 | 3/2018 |
| WO | WO 2018/044940 A1 | 3/2018 |
| WO | WO 2018/085615 A1 | 5/2018 |
| WO | WO 2018/094522 A1 | 5/2018 |

(56) References Cited

FOREIGN PATENT DOCUMENTS

| WO | WO 2018/106628 A1 | 6/2018 |
|---|---|---|
| WO | WO 2018/197544 A1 | 11/2018 |
| WO | WO 2019/074793 A1 | 4/2019 |

OTHER PUBLICATIONS

Wells et al. (2014, Development, vol. 141, pp. 752-760) (Year: 2014).*
Tacer et al. (2010, Mol. Endocrinol., vol. 24(10), pp. 2050-2064) (Year: 2010).*
Ornitz et al. (2015, WIREs Dev. Biol., vol. 4, pp. 215-266) (Year: 2015).*
Zorn et al. (ePUB Aug. 12, 2009, Annual Rev. Cell Dev. Biol., vol. 25, pp. 221-251) (Year: 2009).*
Prakash R. (2014, IJP, vol. 1(6), pp. 366-372) (Year: 2014).*
Brevini et al., 2010, Theriogenology, vol. 74, pp. 544-550 (Year: 2010).*
Paris et al. (2010, Theriogenology, vol. 74, pp. 516-524) (Year: 2010).*
Munoz et al. (2008, Theriogenology, vol. 69, pp. 1159-1164) (Year: 2008).*
Gomez et al. (2010, Theriogenology, vol. 74, pp. 498-515) (Year: 2010).*
Jean et al. (2013, Develop. Growth Differ., vol. 55, pp. 41-51) (Year: 2013).*
Buta et al. (2013, Stem Cell Res., vol. 11, pp. 552-562) (Year: 2013).*
European Exam Report dated May 18, 2018 for Application No. EP 15791404.5, 3 pgs.
International Search Report and Written Opinion dated Jun. 14, 2018 for Application No. PCT/US2018/018585, 14 pgs.
Adorini, L., et al., "Farnesoid X receptor targeting 1 steatohepatitis," Drug Discovery Today, Sep. 2012, 17(17/18):988-997, 10 pgs.
Altman, G.H., et al., "Cell differentiation by mechanical stress," The FASEB Journal, 2001, 16(2):270-272, 13 pgs.
Bohorquez, D.V., et al., "An Enteroendocrine Cell—Enteric Glia Connection Revealed by 3D Electron Microscopy,." Plos One, Feb. 2014, 9(2):e89881, 13 pgs.
Cabezas, J., et al., "Nonalcoholic Fatty Liver Disease: A Pathological View," Liver Biopsy—Indications, Procedures, Results, Chapter 8, InTech, 2012, pp. 161-188, 29 pgs.
Dahl, A., et al., "Translational Regenerative Medicine—Hepatic Systems," Chapter 34, Clinical Aspects of Regenerative Medicine, eds. A. Atala, M.D. and J. Allickson, PhD, Elsevier, Inc., 2015, pp. 469-484, 16 pgs.
Date, S., et al., "Mini-Gut Organoids: Reconstitution of the Stem Cell Niche," Annual Review of Cell and Developmental Biology, Nov. 2015, 31:269-289.
Discher, D.E., et al., "Growth Factors, Matrices, and Forces Combine and Control Stem Cells," Science, Jun. 2009, 324:1673-1677, 5 pgs.
Eicher, A.K., et al., "Translating Developmental Principles to Generate Human Gastric Organoids," Cellular and Molecular Gastroenterology and Hepatology, 2018, 5(3):353-363, 11 pgs.
Gori, M., et al., "Investigating nonalcoholic Fatty Liver Disease in a Liver-on-a-Chip Microfluidic Device," Plos One, Jul. 2016, 11(7):e0159729, 15 pgs.
Gradwohl, G., et al., "neurogenin3 is required for the development of the four endocrine cell lineages of the pancreas," Proc Natl Acad Sci USA, 2000, 97:1607-1611, 5 pgs.
Green, M.D., et al., "Generation of anterior foregut endoderm from human embryonic and induced pluripotent stem cells," Nature Biotechnology, Mar. 2011, 29(3):267-Z72, 7 pgs.
Guilak, F., et al., "Control of Stem Cell Fate by Physical Interactions with the Extracellular Matrix," Cell Stem Cell, Jul. 2009, 5:17-26, 10 pgs.

Hannon, N.R.F., et al., "Generation of Multipotent Foregut Stem Cells from Human Pluripotent Stem Cells," Stem Cell Reports, Oct. 2013, 1:263-306, 14 pgs.
Hardy, T., et al., "Nonalcoholic fatty liver disease: new treatments," Curr Opin Gastroenterol, May 2015, 31(3):175-183, 9 pgs.
Katoh, M., "WNT Signaling in Stem Cell Biology and Regenerative Medicine," Current Drug Targets, 2008, 9(7):565-570, 6 pgs.
Kim, T-H., et al., "Stomach development, stem cells and disease," Development, 2016, 143:554-565, 12 pgs.
Koike, M., et al., "Effects of mechanical strain on proliferation and differentiation of bone marrow stromal cell line ST2," J Bone Miner Metab, 2005, 23:219-225, 7 pgs.
Kolahchi, A.R., et al., "Microfluidic-Bases Multi-Organ Platforms for Drug Discovery," Micromachines, 2016, 7(162):1-33, 33 pgs.
Lin, C., et al., "The application of engineered liver tissues for novel drug discovery," Expert Opinion on Drug Discovery, 2015, 10(5):519-540.
Luo, X., et al., "Generation of endoderm lineages from pluripotent stem cells," Regenerative Medicine, 2017, 12(1):77-89, 13 pgs.
McCracken, K.W., et al., "Mechanisms of embryonic stomach development," Seminars in Cell & Development Biology, 2017, 66:36-42, 7 pgs.
Micallef, S.J., et al., "Endocrine cells develop within pancreatic bud-like structures derived from mouse ES cells differentiated in response to BMP4 and retinoic acid," Stem Cell Research, 2007, 1:25-36, 12 pgs.
Mudaliar, S., et al., "Efficacy and Safety of the Farnesoid X Receptor Agonist Obeticholic Acid in Patients with Type 2 Diabetes and Nonalcoholic Fatty Liver Disease," Gastroenterology, 2013, 145:574-582, 10 pgs.
Nandivada, P., et al., "Treatment of Parenteral Nutrition-Associated Liver Disease: The Role of Lipid Emulsions," Advances in Nutrition, Reviews from ASN EB 2013 Symposia, pp. 711-717, 7 pgs.
Neuschwander-Tetri, B.A., et al., "Farnesoid X nuclear receptor ligand obeticholic acid for non-cirrhotic, non-alcoholic steatohepatitis (FLINT): a multicentre, randomised, placebo-controlled trial," Lancet, 2015, 385:956-965, 10 pgs.
Park, H.R., et al., "Lipotoxieity of Palrnaitie Acid on Neural Progenitor Cells and Hippocampal Neurogenesis," Toxicol Res, 2011, 27(2):103-110, 8 pgs.
Park, J.S., et al., "Differential Effects of Equiaxial and Uniaxial Strain on Mesenchymal Stem Cells," Biotechnology and Bioengineering, Nov. 2004, 88(3):359-368, 10 pgs.
Park, J.S., et al., "The effect of matrix stiffness on the differentiation of mesenhymal stem cells in response to TGF-β," Biomaterials, 2011, 32:3921-3930, 10 pgs.
Pennisi, C.P., Ph.D., et al., "Uniaxial Cyclic Strain Drives Assembly and Differentiation of Skeletal Myocytes," Tissue Engineering: Part A, 2011, 17(19-20):2543-2550, 8 pgs.
Pompaiah, M., et al., "Gastric Organoids: An Emerging Model System to Study *Helicobacter pylori* Pathogenesis," Molecular Pathogenesis and Signal Transduction by *Helicobacter pylori*, Current Topics in Microbiology and Immunology, N. Tegtmeyer, et al., (eds), 2017, pp. 149-168.
Qi, M-C., et al., "Mechanical strain induces osteogenie differentiation: Cbfa1 and Ets-1 expression in stretched rat mesenehymal stem cells," Int J Oral Maxillofae Surg, 2008, 37:453-458, 6 pgs.
Reilly, G.C., et al., "Intrinsic extracellular matrix properties regulate stem cell differentiation," Journal of Biomeehanies, 2010, 43:55-62, 8 pgs.
Rennert, K., et al., "A microfluidically perfused three dimensional human liver model," Biomaterials, 2015, 71:119-131, 13 pgs.
Saenz, J.B., et al., "Stomach growth in a dish: A protocol has been developed to grow structures that resemble the main part of the stomach in vitro from human embryonic stem cells—an advance that provides insights into stomach development," Nature, Jan. 2017, 541:160-161, 2 pgs.
Saha, S., et al., "Inhibition of Human Embryonic Stem Cell Differentiation by Medical Strain," Journal of Cellular Physiology, 2006, 206:126-137, 12 pgs.

(56) References Cited

OTHER PUBLICATIONS

Schmelter, M., et al., "Embryonic stem cells utilize reactive oxygen species as transducers of mechanical strain-induced cardiovascular differentiation," The FASEB Journal, Jun. 2006, 20(8):1182-1184, 16 pgs.
Schuppan, D., et al., "Non-alcoholic steatohepatitis: Pathogenesis and novel therapeutic approaches," Journal of Gastroenterology and Hepatology, 2013, 28(Suppl 1):68-76, 9 pgs.
Shimizu, N., et al., "Cyclic strain induces mouse embryonic stem cell differentiation into vascular smooth muscle cells by activating PDGF receptor β," J Appl Physiol, 2008, 104:766-772, 7 pgs.
Singh, S., et al., "Comparative Effectiveness of Pharmacological Interventions for Nonalcoholic Steatohepatitis: A Systematic Review and Network Meta-analysis," Hepatology, Nov. 2015, 62(5):1417-1432, 16 pgs.
Skardal, A., et al., "Organoid-on-a-chip and body-on-a-chip systems for drug screening and disease modeling," Drug Discovery Today, Sep. 2016, 21(9):1399-1411, 13 pgs.
Snoeck, H-W., "Generation of Anterior Foregut Derivatives from Pluripotent Stem Cells," Stem Cells Handbook, S. Sell (ed.), 2013, pp. 161-175.
Sonntag, F., et al., "Design and prototyping of a chip-based multi-micro-organoid culture system for substance testing, predictive to human (substance) exposure," Journal of Biotechnology, 2010, 148:70-75, 6 pgs.
Ward, D.F., Jr., et al., "Mechanical Strain Enhances Extracellular Matrix-Induced Gene Focusing and Promotes Osteogenic Differentiation of Human Mesenchymal Stem Cells Through an Extracellular-Related Kinase-Dependent Pathway," Stem Cells and Development, 2007, 16:467-479, 14 pgs.
Willet, S.G., et al., "Stomach Organ and Cell Lineage Differentiation: From Embryogenesis to Adult Homeostasis," Cellular and Molecular Gastroenterology and Hepatology, 2016, 2(5):546-559, 14 pgs.
Zhang, W., et al., "Elastomeric Free-Form Blood Vessels for Interconnecting Organs on Chip Systems," Lab Chip Apr. 2016, 16(9):1579-1586, 19 pgs.
Zhang, Y.S., et al., "Multisensor-integrated organs-on-chips platforms for automated and continual in situ monitoring of organoid behaviors," PNAS Early Edition, 2017, 10 pgs.
Zhang, Y.S., et al., "Seeking the right context for evaluating nanomedicine: from tissue models in petri dishes to microfluidic organs-on-a-chip," Nanomedicine (Lond.), 2015, 10(5):685-688, 4 pgs.
Zhou, J., et al., "The Potential for Gut Organoid Derived Interstitial Cells of Cajal in Replacement Therapy," International Journal of Molecular Sciences, Sep. 2017, 18:1-17, 17 pgs.
International Search Report and Written Opinion dated Jan. 18, 2018 for Application No. PCT/US2017/059865, 12 pgs.
International Search Report and Written Opinion dated Jan. 19, 2018 for Application No. PCT/US2017/059845, 13 pgs.
International Search Report and Written Opinion dated Jan. 29, 2018 for Application No. PCT/US2017/059860, 13 pgs.
Stark, R., et al., "Development of an endoluminal intestinal lengthening capsule," Journal of Pediatric Surgery, 2012, 47:136-141, 6 pgs.
European Exam Report dated Jul. 4, 2018 for Application No. EP 15728704.6, 3 pgs.
International Searching Authority Invitation to Pay Additional Fees and, Where Applicable, Protest Fee, dated Jun. 27, 2018 for Application No. PCT/US/2018/029083, 3 pgs.
Ader. M., et al., "Modeling human development in 3D culture," Current Opinion in Cell Biology, 2014, 31:23-28, 6 pgs.
Aurora, M., et al., "hPSC-derived lung and intestinal organoids as models of human fetal tissue," Developmental Biology, 2016, 420:230-238, 9 pgs.
Baptista, P.M., et al., "The Use of Whole Organ Decellularization for the Generation of a Vascularized Liver Organoid," Hepatology, 2011, 53(2):604-617, 14 pgs.
Barker, N., et al., "Tissue-Resident Adult Stem Cell Populations of Rapidly Self-Renewing Organs," Cell Stem Cell, Dec. 2010, 7:656-670, 15 pgs.
Bartfeld, S., et al., "Stem cell-derived organoids and their application for medical research and patient treatment," J Mol Med, 2017, 95:729-738, 10 pgs.
Baumann, K., "Colonic organoids for drug testing and colorectal disease modelling," Nature Reviews Molecular Cell Biology, Jul. 2017, 1 pg.
Bitar, K.N., et al., "Intestinal Tissue Engineering: Current Concepts and Future Vision of Regenerative Medicine in the Gut," Neurogastroenterol Motil., Jan. 2012, 24(1):7-19, 20 pgs.
Bruens, L., et al., "Expanding the Tissue Toolbox: Deriving Colon Tissue from Human Pluripotent Stem Cells," Cell Stem Cell, Jul. 2017, 21(1):3-5, 3 pgs.
Brugmann, S.A., et al., "Building additional complexity to in vitro-derived intestinal tissues," Stem Cell Research & Therapy. 2013, 4( Suppl 1):S1, 5 pgs.
Cao, L., et al., "Development of Intestinal Organoids as Tissue Surrogates: Cell Composition and the Epigenetie Control of Differentiation," Molecular Carcinogenesis, 2015, 54:189-202, 14 pgs.
Cieslar-Pobuda, A., et al., The expression pattern of PFKFB3 enzyme distinguishes between induced-pluripotent stem cells and cancer stem cells, Oncotarget, 6(30):29753-29770, 18 pgs.
Clevers, H., "Modelng Development and Disease with Organoids," Cell, Jun. 2016, 165:1586-1597, 12 pgs.
Correia, C., et al., "Combining Hypoxia and Bioreactor Hydrodynamics Boosts Induced Pluripotent Stem Cell Differentiation Towards Cardiomyocytes," Stem Cell Rev and Rep, 2014, 10:786-801, 16 pgs.
Davenport, C., et al., "Anterior-Posterior Patterning of Definitive Endoderm Generated from Human Embryonic Stem Cells Depends on the Differential Signaling of Retinoic Acid. Wnt-, and BMP-Signaling," Stem Cells, 2016, 34:2635-2647, 13 pgs.
Dedhia, P.H., et al., "Organoid Models of Human Gastrointestinal Development and Disease," Gastroenterology, 2016, 150:1098-1112, 15 pgs.
Ezashi, T., et al., "Low $O_2$ tensions and the prevention of differentiation of hES cells," PNAS. Mar. 2005, 102(13):4783-4788, 6 pgs.
Fatehullah, A., et al., "Organoids as an in vitro model of human development and disease," Nature Cell Biology, Mar. 2106, 18(3):246-254, 9 pgs.
Finkbeiner, S.R., et al., "A Gutsy Task: Generating Intestinal Tissue from Human Pluripotent Stem Cells," Dig Dis Sci, 2013, 58:1176-1184, 9 pgs.
Finkbeiner, S.R., et al., "Stem Cell-Derived Human Intestinal Organoids as an Infection Model for Rotaviruses," mBio, Jul./Aug. 2012, 3(4):e00159-12, 6 pgs.
Gessner, R.C., et al., "Functional ultrasound imaging for assessment of extracellular matrix scaffolds used for liver organoid formation," Biomaterials, 2013, 34:9341-9351, 11 pgs.
Gouon-Evans, V., et al., "BMP-4 is required for hepatic specification of mouse embryonic stem cell-derived definitive endoderm," Nature Biotechnology, Nov. 2006, 24(11):1402-1411, 10 pgs.
Han, M-E., et al., "Gastric stem cells and gastric cancer stem cells," Anatomy & Cell Biology, 2013, 46:8-18, 11 pgs.
Howell, J.C., et al., "Generating intestinal tissue from stem cells: potential for research and therapy," Regen Med., 6(6):743-755, 22 pgs.
Huch, M., et al., "Lgr5$^+$ liver stem cells, hepatic organoids and regenerative medicine," Regen. Med., 2013, 8(4):385-387, 3 pgs.
Huch, M., et al., "Modeling mouse and human development using organoid cultures," Development, 2015, 142:3113-3125, 13 pgs.
Kostrzewski, T., et al., "Three-dimensional perfused human in vitro model of non-alcoholic fatty liver disease," World J Gastroenterol, 2017, 23(2):204-215, 13 pgs.
Kretzschmar, K., et al., "Organoids: Modeling Development and the Stem Cell Niche in a Dish," Developmental Cell, Sep. 2016, 38:590-600, 11 pgs.
Kuratnik, A., et al., "Intestinal organoids as tissue surrogates for toxicological and pharmacological studies," Biochemical Pharmacology, 2013, 85:1721-1726, 6 pgs.

(56) References Cited

OTHER PUBLICATIONS

Li, Y., et al., "In vitro organogenesis from pluripotent stem cells," Organogenesis, Jun. 2014, 10(2):159-163, 5 pgs.
Lu, Y., et al., "A Novel 3D Liver Organoid System for Elucidation of Hepatic Glucose Metabolism," Biotechnol Bioeng., Feb. 2012, 109(2):595-604, 21 pgs.
McCracken, K.W., "Mechanisms of endoderm patterning and directed differentiation of human stem cells into foregut tissues," Dissertation, Graduate School of the University of Cincinnati, Jun. 19, 2014, 185 pgs.
Ogaki, S., et al., "Wnt and Notch Signals Guide Embryonic Stem Cell Differentiation into the Intestinal Lineages," Stem Cells, 2013, 31:1086-1096, 11 pgs.
Park, K.I., et al., "Acute injury directs the migration, proliferation, and differentiation of solid organ stem cells: Evidence for the effect of hypoxia-ischemia in the CNS on clonal "reporter" neural stem cells," Experimental Neurology, 2006, 199:159-178, 23 pgs.
Pastula, A., et al., "Three-Dimensional Gastrointestinal Organoid Culture in Combination with Nerves or Fibroblasts: A Method to Characterize the Gastrointestinal Stem Cell Niche." Stem Cells International, 2016, 16 pgs.
Pulikkot, S., "Establishment of a 3D Culture Model of Gastric Stem Cells Supporting Their Differentiation into Mucous Cells Using Microfibrous Polycaprolactone Scaffold," Dissertation, United Arab Emirates University, College of Medicine and Health Sciences, May 2015, 187 pgs. (4 parts: Part 1—58 pgs; Part 2—69 pgs; Part 3—31 pgs; Part 4—29 pgs.).
Ramachandran, S.D., et al., "In Vitro Generation of Functional Liver Organoid—Like Structures Using Adult Human Cells," Plos One, Oct. 2015, 14 pgs.
Ray, K., "Engineering human intestinal organoids with a functional ENS," Nature Reviews Gastroenterology & Hepatology, Nov. 2016, 1 pg.
Saito, M., et al., "Reconstruction of liver organoid using a bioreactor," World J Gastroenterol, Mar. 2006, 12(12):1881-1888, 8 pgs.
Sampaziotis, F., et al., "Potential of Human Induced Pluripotent Stem Cells in Studies of Liver Disease," Hepatology, Jul. 2015, 62(1):303-311, 9 pgs.
Sasai, Y., "Next-Generation Regenerative Medicine: Organogenesis from Stem Cells in 3D Culture," Cell Stem Cell, May 2013, 12:520-530, 11 pgs.
Schlieve, C.R., et al., "Created of Warm Blood and Nerves: Restoring an Enteric Nervous System in Organoids," Cell Stem Cell, Jan. 2017, 20:5-7, 3 pgs.
Shah, S.B., et al., "Cellular self-assembly and biomaterials-based organoid models of development and diseases," Acta Biomaterialia, 2017, 53:29-45, 17 pgs.
Sinagoga, K.L., et al., "Generating human intestinal tissues from pluripotent stem cells to study development and disease," The EMBO Journal, 2015, 34(9):1149-1163, 15 pgs.
Snykers, S., et al., "In Vitro Differentiation of Embryonic and Adult Stem Cells into Hepatocytes: State of the Art," Stem Cells, 2009, 27:577-605, 29 pgs.
Soto-Gutierrez, A., et al., "Engineering of an Hepatic Organoid to Develop Liver Assist Devices," Cell Transplant, 2010, 19(6):815-822, 12 pgs.
Sugawara, T., et al., "Organoids recapitulate organs?," Stem Cell Investig, 2018, vol. 5, Iss. 3, 4 pgs.
Sui, L., et al., "Signaling pathways during maintenance and definitive endoderm differentiation of embryonic stem cells," Int J Dev Bio, 2013, 57:1-12, 12 pgs.
Sun, Y., et al., "Genome engineering of stem cell organoids for disease modeling," Protein Cell, 2017, 8(5):315-327, 13 pgs.
Tamminen, K., et al., "Intestinal Commitment and Maturation of Human Pluripotent Stem Cells Is Independent fo Exogenous FGF4 and R-spondin1," PLOS One, Jul. 2015, 10(7):e0134551, 19 pgs.
Toivonen, S., et al., "Activin A and Wnt-dependent specification of human definitive endoderm cells," Experimental Cell Research, 2013, 319:2535-2544, 10 pgs.

Tsakmaki, A., et al., "3D intestinal organoids in metabolic research: virtual reality in a dish," Current Opinion in Pharmacology, 2017, 37:51-58, 8 pgs.
Wang, A., et al., "Generating cells of the gastrointestinal system: current approaches and applications for the differentiation of human pluripotent stem cells," J Mol Med, 2012, 90:763-771, 9 pgs.
Workman, M.J., "Generating 3D human intestinal organoids with an enteric nervous system," Thesis, Graduate School of the University of Cincinnati, Oct. 2014, 61 pgs.
Xinaris, C., et al., "Organoid Models and Applications in Biomedical Research," Nephron 2015, 130:191-199, 9 pgs.
Yin, C., et al., "Hepatic stellate cells in liver development, regeneration, and cancer," The Journal of Clinical Investigation, May 2013, 123(5):1902-1910, 9 pgs.
Singaporean Written Opinion dated Oct. 19, 2017 for Application No. SG11201609953X, 8 pgs.
Cao, L., et al., "Development of Intestinal Organoids as Tissue Surrogates: Cell Composition and the Epigenetic Control of Differentiation," Molecular Carcinogenesis, 2015, 54:189-202, 14 pgs.
Clevers, H., "Modeling Development and Disease with Organoids," Cell, Jun. 2016, 165:1586-1597, 12 pgs.
Correia, C., et al., "Combining Hypoxia and Bioreaetor Hydrodynamics Boosts Induced Pluripotent Stem Cell Differentiation Towards Cardiomyoeytes," Stem Cell Rev and Rep, 2014, 10:786-801, 16 pgs.
Davenport, C., et al., "Anterior-Posterior Patterning of Definitive Endoderm Generated from Human Embryonic Stem Cells Depends on the Differential Signaling of Retinoic Acid, Wnt-, and BMP-Signaling," Stem Cells, 2016, 34:2635-2647, 13 pgs.
Finkbeiner, S.R., et al., "A Gutsy Task: Generating Intestinal Tissue from Human Plulipotent Stem Cells," Dig Dis Sci, 2013, 58:1176-1184, 9 pgs.
Ray, K., "Engineering human intestinal organoids with a functional ENS," Nature Reviews Gastroenterology & Hematology, Nov. 2016, 1 pg.
Sampaziotis, F., et al., "Potential of Human Induced Pluripotent Stem Cells in Studies of Liver Disease," Hematology, Jul. 2015, 62(1):303-311, 9 pgs.
Snykers, S., et al., "In Vitro Differentiation of Embryonic and Adult Stem Cells into Hepatoeytes: State of the Art," Stem Cells, 2009, 27:577-605, 29 pgs.
Tamminen, K., et al., "Intestinal Commitment and Maturation of Human Pluripotent Stem Cells Is Independent fo Exogenous FGF4 and R-spondinl," Plos One, Jul. 2015, 10(7):e0134551, 19 pgs.
Workman, M.J., "Generating 3D human intestinal organoids with an enteric nervous system," Thesis, Graduate School of the University of Cincinnati, Oct. 2014, 61 pgs.
Amieva, M.R., et al. "*Helicobacter pylori* enter and survive within multivesicular vacuoles of epithelial cells," Cell. Microbiol., 2002, 4(10):677-690, 15 pgs.
Anderson, G., et al., "Loss of enteric dopaminergic neurons and associated changes in colon motility in an MPTP mouse model of Parkinson's disease," Exp Neurol, Sep. 2007, 207:4-12, 16 pgs.
Anlauf, M., et al., "Chemical coding of the human gastrointestinal nervous system: cholinergic, VIPergic, and catecholaminergic phenotypes," The Journal of Comparative Neurology, 2003, 459:90-111, 22 pgs.
Baetge, G., et al., "Transient catecholaminergic (TC) cells in the vagus nerves and bowel of fetal mice: relationship to the development of enteric neurons," Developmental Biology, 1989, 132:189-211, 23 pgs.
Bajpai, R., et al., "CHD7 cooperates with PBAF to control multipotent neural crest formation," Nature, Feb. 18, 2010, 463:958-962, 7 pgs.
Bergner, A.J., et al., "Birthdating of myenteric neuron subtypes in the small intestine of the mouse," The Journal of Comparative Neurology, 2014, 522:514-527, 14 pgs.
Blaugrund, E., et al., "Distinct subpopulations of enteric neuronal progenitors defined by time of development, sympathoadrenal lineage markers and Mash-1-dependence," Development 122, 1996, 309-320, 12 pgs.
Burns, A.J., et al., "Neural stem cell therapies for enteric nervous system disorders," Nature Reviews/Gastroenterology & Hepatology, May 2014, 11:317-328, 12 pgs.

(56) References Cited

OTHER PUBLICATIONS

Campbell, F.C., et al., "Transplantation of cultured small bowel enterocytes," Gut, 1993, 34:1153-1155, 4 pgs.
Chen, T-W., et al., "Ultrasensitive fluorescent proteins for imaging neuronal activity," Nature, Jul. 18, 2013, 499:295-300, 8 pgs.
Cheng, X., et al., "Self-renewing endodermal progenitor lines generated from human pluripotent stem cells," Cell Stem Cell, Apr. 6, 2012, 10:371-384, 14 pgs.
Churin, Y., et al., "*Helicobacter pylori* CagA protein targets the c-Met receptor and enhances the motogenic response," J. Cell Biol., 2003, 161:249-255, 7 pgs.
Costa, M., et al., "A method for genetic modification of human embryonic stem cells using electroporation," Nature Protocols, Apr. 5, 2007, 2:792-796, 5 pgs.
Covacci, A., et al., "Molecular characterization of the 128-kDa immunodominant antigen of *Helicobacter pylori* associated with cytotoxicity and duodenal ulcer," Proc Natl Acad Sci USA, Jun. 1993, 90:5791-5795, 5 pgs.
Curchoe, C.L., et al., "Early acquisition of neural crest competence during hESCs neuralization," PloS One, Nov. 2010, 5:1-17, 17 pgs.
Dekaney, C.M., et al., "Expansion of intestinal stem cells associated with long-term adaptation following ileocecal resection in mice," Am J Physiol Gastrointest Liver Physiol, Sep. 13, 2007, 293:G1013-G1022, 10 pgs.
Denham, M., et al., "Multipotent caudal neural progenitors derived from human pluripotent stem cells that give rise to lineages of the central and peripheral nervous system," Stem Cells, Mar. 5, 2015, 33:1759-1770, 12 pgs.
Fordham, R.P., et al., "Transplantation of expanded fetal intestinal progenitors contributes to colon regeneration after injury," Cell Stem Cell, Dec. 5, 2013, 13:734-744, 11 pgs.
Fu, M., et al., "HOXB5 expression is spatially and temporarily regulated in human embryonic gut during neural crest cell colonization and differentiation of enteric neuroblasts," Developmental Dynamics, 2003, 228:1-10, 10 pgs.
Fu, M., et al., "Embryonic development of the ganglion plexuses and the concentric layer structure of human gut: a topographical study," Anatomy and Embryology, Feb. 27, 2004, 208:33-41, 10 pgs.
Furness, J.B., "The enteric nervous system and neurogastroenterology," Nature Reviews/Gastroenterology & Hepatology, May 2012, 9:286-294, 9 pgs.
Gracz, A.D., et al., "Brief report: CD24 and CD44 mark human intestinal epithelial cell populations with characteristics of active and facultative stem cells," Stem Cells, Apr. 4, 2013, 31:2024-2030, 7 pgs.
Groneberg, D.A., et al., "Intestinal peptide transport: ex vivo uptake studies and localization of peptide carrier PEPT1," Am J Physiol Gastrointest Liver Physiol, Sep. 2001, 281:G697-G704, 8 pgs.
Grosse, A.S., et al., "Cell dynamics in fetal intestinal epithelium: implications for intestinal growth and morphogenesis," Development, 2011, 138:4423-4432, 10 pgs.
Hao, M.M., et al., "Development of enteric neuron diversity," J. Cell. Mol. Med., 2009 13:1193-1210, 18 pgs.
Hockemeyer, D., et al., "Genetic engineering of human ES and iPS cells using Tale nucleases," Nat Biotechnol., 2012, 29:731-734, 8 pgs.
Huebsch, N., et al., "Automated video-based analysis of contractility and calcium flux in human-induced pluripotent stem cell-derived cardiomyocytes cultured over different spatial scales," Tissue Engineering: Part C, 2015, 21:467-479, 15 pgs.
Johansson, K.A., et al., "Temporal Control of Neurogenin3 Activity in Pancreas Progenitors Reveals Competence Windows for the Generation of Different Endocrine Cell Types," Dev Cell, 2007, 12:457-465, 9 pg.
Johnson, L.R., et al., "Stimulation of rat oxyntic gland mucosal growth by epidermal growth factor," Am. J. Physiol., 1980, 238:G45-49, 5 pgs.
Jung, P., et al., "Isolation and in vitro expansion of human colonic stem cells," Nature Medicine, Oct. 2011, 17:1225-1227, 3 pgs.

Juno, R.J., et al., "A serum factor after intestinal resection stimulates epidermal growth factor receptor signaling and proliferation in intestinal epithelial cells," Surgery, Aug. 2002, 132:377-383, 7 pgs.
Juno, R.J., et al., "A serum factor(s) after small bowel resection induces intestinal epithelial cell proliferation: effects of timing, site, and extent of resection," Journal of Pediatric Surgery, Jun. 2003, 38:868-874, 7 pg.
Kabouridis, P.S., et al., "Microbiota controls the homeostasis of glial cells in the gut lamina propria," Neuron, Jan. 21, 2015, 85:289-295, 8 pgs.
Kawaguchi, Y., et al., "The role of the transcriptional regulator Ptf1a in converting intestinal to pancreatic progenitors," Nat Genet, 2002, 32:128-134, 7 pgs.
Kosinski, C., et al., "Indian hedgehog regulates intestinal stem cell fate through epithelial-mesenchymal interactions during development," Gastroenterology, Sep. 2010, 139:893-903, 17 pgs.
Kovalenko, P.L., et al., "The correlation between the expression of differentiation markers in rat small intestinal mucosa and the transcript levels of schlafen 3," JAMA Surg., Sep. 4, 2013, 148:1013-1019, 7 pgs.
Kudoh, T., et al., "Distinct roles for Fgf, Wnt and retinoic acid in posteriorizing the neural ectoderm," Development, 2002, 129:4335-4346, 12 pgs.
Kumar, M., et al., "Signals from lateral plate mesoderm instruct endoderm toward a pancreatic fate," Dev Biol, 2003, 259:109-122, 14 pgs.
Lahar, N., et al., "Intestinal suhepithelial myofibroblasts support in vitro and in vivo growth of human small intestinal epithelium," PLoS One, Nov. 2011, 6:e26898, 9 pgs.
Lancaster, M.A., et al., "Organogenesis in a dish: modeling development and disease using organoid technologies," Science, Jul. 18, 2014, 345:283 & 1247125-1—9, 11 pgs.
Le Douarin, N.M., et al., "Neural crest cell plasticity and its limits," Development 131, 2004, 4637-4650, 14 pgs.
Lee, G., et al., "Isolation and directed differentiation of neural crest stem cells derived from human embryonic stem cells," Nature Biotechnology, Dec. 2007, 25:1468-1475, 9 pgs.
Levin, D.E., et al., "Human tissue-engineered small intestine forms from postnatal progenitor cells," Journal of Pediatric Surgery, 2013, 48:129-137, 9 pgs.
Longmire, T.A., et al., "Efficient Derivation of Purified Lung and Thyroid Progenitors from Embryonic Stem Cells," Stem Cell, 2012, 10:398-411, 14 pgs.
Lui, V.C., et al., "Perturbation of hoxb5 signaling in vagal neural crests down-regulates ret leading to intestinal hypo ganglionosis in mice," Gastroenterology, 2008, 134:1104-1115, 12 pgs.
Majumdar, A.P.N., "Postnatal Undernutrition: Effect of Epidermal Growth Factor on Growth and Function of the Gastrointestinal Tract in Rats," J. Pediatr. Gastroenterol. Nutr., 1984, 3:618-625, 8 pgs.
Martín, M., et al., "Dorsal pancreas agenesis in retinoic acid-deficient Raldh2 mutant mice," Dev Biol., 2005, 284:399-411, 13 pgs.
McKeown, S.J., et al., "Hirsehsprung disease: a developmental disorder of the enterie nervous system," Wiley Interdisciplinary Reviews Developmental Biology, Jan./Feb. 2013, 2:113-129, 17 pgs.
Meerbrey, K.L., et al., "The pINDUCER lentiviral toolkit for inducible RNA interference in vitro and in vivo." Proc Natl Acad Sci USA, 2011, 108:3665-3670, 6 pgs.
Mica, Y., et al., "Modeling neural crest induction, melanocyte specification and disease-related pigmentation defects in hESCs and patient-specific iPSCs," Cell Reports, Apr. 25, 2013, 3:1140-1152, 27 pgs.
Mills, J.C., et al., "Gastric Epithelial Stem Cells," Gastroenterology, 2011, 140:412-424, 13 pgs.
Molotkov, A., et al., "Retinoie Acid Generated by Raldh2 in Mesoderrn is Required for Mouse Dorsal Endodermal Pancreas Development," Dev Dyn, 2005, 232:950-957, 8 pgs.
Mou, H., et al., "Generation of Multipotent Lung and Airway Progenitors from Mouse ESCs and Patient-Specific Cystic Fibrosis iPSCs," Stem Cell, 2012, 10:385-397, 13 pgs.

(56) References Cited

OTHER PUBLICATIONS

Obermayr, F., et al., "Development and developmental disorders of the enteric nervous system," Nature Reviews/Gastroenterology & Hepatology, Jan. 2013, 10:43-57, 15 pgs.
Okita, K., et al., "An Efficient Nonviral Method to Generate Integration-Free Human-Induced Pluripotent Stem Cells from Cord Blood and Peripheral Blood Cells," Stem Cells, 2013, 31:458-466, 9 pgs.
Olbe, L., et al., "A Mechanism by Which *Helicobacter pylori* Infection of the antrum Contributes to the Development of Duodenal Ulcer," Gastroenterology, 2001, 110:1386-1394, 9 pgs.
Parkin, D.M., "The global health burden of infection-associated cancers in the year 2002," Int. J. Cancer, 2006, 118:3030-3044, 15 pgs.
Peek, R.M., Jr., et al., "*Helicobacter pylori* cagA+ Strains and Dissociation of Gastric Epithelial Cell Proliferation From Apoptosis," J. Natl. Cancer Inst., 1997, 89:863-868, 7 pgs.
Peek, R.M., Jr., "*Helicobacter pylori* infection and disease: from humans to animal models," Dis Model Mech, 2008, 1:50-55, 6 pgs.
Saffrey, M.J., "Cellular changes in the enteric nervous system during ageing," Developmental Biology, 2013, 382:344-355, 12 pgs.
Sasselli, V., et al., "The enteric nervous system," Developmental Biology, Jan. 2012, 366:64-73, 10 pgs.
Sato, T., et al., "Long-term expansion of epithelial organoids from human colon, adenoma, adenocarcinoma, and Barrett's epithelium," Gastroenterology, Nov. 1, 2011, 141:1762-1772, 11 pgs.
Schonhoff, S.E., et al., "Neurogenin 3-expressing progenitor cells in the gastrointestinal tract differentiate into both endocrine and non-endocrine cell types," Dev Biol, 2004, 270:443-454, 12 pgs.
Schumacher, M.A., et al., "Gastric Sonic Hedgehog Acts as a Macrophage Chemoattractant During the Immune Response to *Helicobacter pylori*," Gastroenterology, 2012, 142:1150-1159, 16 pgs.
Si-Tayeb, K., et al., "Highly Efficient Generation of Human Hepatocyte-Like Cells from Induced Pluripotent Stem Cells," Hepatology, 2010, 51:297-305, 9 pgs.
Spear, P.C., et al., "Interkinetic nuclear migration: A mysterious process in search of a function," Develop. Growth Differ., 2012, 54:306-316, 12 pgs.
Tait, I.S., et al., "Colonic mucosal replacement by syngeneic small intestinal stem cell transplantation," The American Journal of Surgery, Jan. 1994, 167:67-72, 6 pgs.
Tait, I.S., et al., "Generation of neomucosa in vivo by transplantation of dissociated rat postnatal small intestinal epithelium," Differentiation, 1994 56:91-100, 10 pgs.
Tang, W., et al., "Faithful expression of multiple proteins via 2A-peptide self-processing: a versatile and reliable method for manipulating brain circuits," The Journal of Neuroscience, Jul. 8, 2009, 29:8621-8629, 9 pgs.
Teo, A.K.K., et al., "Activin and BMP4 Synergistically Promote Formation of Definitive Endoderm in Human Embryonic Stem Cells," Stem Cells, 2012, 30:631-642, 12 pgs.
Tiso, N., et al., "BMP signalling regulates anteroposterior endoderm patterning in zebrafish," Mech Dev, 2002, 118:29-37, 9 pgs.
Verzi, M.P., et al., "Role of the Homeodomain Transcription Factor Bapxl in Mouse Distal Stomach Development," Gastroenterology, 2009, 136:1701-1710, 10 pgs.
Wallace, A.S., et al., "Development of the enteric nervous system, smooth muscle and interstitial cells of Cajal in the human gastrointestinal tract," Cell and Tissue Research, Jan. 26, 2005, 319:367-382, 16 pgs.
Wang, F., et al., "Isolation and characterization of intestinal stem cells based on surface marker combinations and colony-formation assay," Gastroenterology, 2013, 145:383-395.el-e21, 34 pgs.
Wang, Z., et al., "Retinoic acid regulates morphogenesis and patterning of posterior foregut derivatives," Dev Biol, 2006, 297:433-445.

Warlich, E., et al., "Lentiviral vector design and imaging approaches to visualize the early stages of cellular reprogramming," Mol. Ther., Apr. 2011, 19:782-789, 9 pgs.
Wen, S. et al., "*Helicobacter pylori* virulence factors in gastric carcinogenesis," Cancer Lett., 2009, 282:1-8, 8 pgs.
Williamson, R.C.N., et al., "Humoral stimulation of cell proliferation in small bowel after transection and resection in rats," Gastroenterology, 1978, 75:249-254, 6 pgs.
Xia, H.H-X., et al. "Antral-Type Mueosa in the Gastric Incisura, Body, and Fundus (Antralization): A Link Between *Helicobacter pylori* Infection and Intestinal Metanlasia?", Am. J. Gastroenterol., 2000, 95:114-121, 8 ps.
Young, H.M et al., "Expression of Ret-, $p75^{NTR}$-, Phox2a-, Phox2b-, and tyrosine hydroxylase-immunoreactivity by undifferentiated neural crest-derived cells and different classes of enteric neurons in the embryonic mouse gut," Developmental Dynamics, 1999, 216:137-152, 16 pgs.
Young, H.M et al., "GDNF is a chemoattractant for emetic neural cells," Developmental biology, Dec. 19, 2000, 229:503-516, 14 pgs.
Yuan, Y., et al., "Peptic ulcer disease today," Nat Clin Pract Gastroenterol Hepatol, 2006, 3:80-89 10 pgs.
Yui, S., et al., "Functional engraftment of colon epithelium expanded in vitro from a single adult Lgr5(+) stem cell." Nature Medicine. Apr. 2012, 18:618-623, 8 pgs.
Zhang, D., et a., "Neural crest regionalisation for enteric nervous system formation: implications for Hirschsprung's disease and stem cell therapy," Developmental Biology, Jan. 18, 2010, 339:280-294, 15 pgs.
European Exam Report dated Sep. 28, 2017 for Application No. EP 15728704.6, 4 pgs.
International Preliminary Report on Patentability dated Apr. 18, 2017 for Application No. PCT/US2015/055956, 8 pgs.
International Search Report and Written Opinion dated Jan. 19, 2017 for Application No. PCT/US2016/058864, 11 pgs.
International Search Report and Written Opinion dated Aug. 14, 2017 for Application No. PCT/US2017/013109, 17 pgs.
U.S. Appl. No. 15/312,939, filed Nov. 21, 2016, Wells et al.
U.S. Appl. No. 15/515,840, filed Mar. 30, 2017, Wells et al.
U.S. Appl. No. 61/332,178, filed May 6, 2010.
U.S. Appl. No. 62/003,719, filed May 28, 2014.
U.S. Appl. No. 62/065,131, filed Oct. 17, 2014.
Arora, N., et al., "A process engineering approach to increase organoid yield," Development, 2017, 144:1128-1136, 9 pgs.
Asai, A., et al., "Paracrine signals regulate human liver organoid maturation from induced pluripotent stem cells," Development, 2017, 144:1056-1064, 9 pgs.
Eberhard, J., et al., "A cohort study of the prognostic and treatment predictive value of SATB2 expression in colorectal cancer," British Journal of Cancer, 2012, 106:931-938, 8 pgs.
Li, Z., et al., "SATB2 is a sensitive marker for lower gastrointestinal well-differentiated neuroendocrine tumors," Int J Clin Exp Pathol, 2015, 8(6):7072-7082, 11 pgs.
McCauley, H.A., et al., "Pluripotent stem cell-derived organoids: using principles of developmental biology to grow human tissues in a dish," Development, 2017, 144:958-962, 5 pgs.
McCracken, K.W., et al., "Wnt/β-catenin promotes gastric fundus specification in mice and humans," Nature, Jan. 2017, 541(7636):182-187, 31 pgs.
Munera, J.O., et al., "Generation of Gastrointestinal Organoids from Human Pluripotent Stem Cells, Organ Regeneration," In: Tsuji, T., (eds), Organ Regeneration. Methods in Molecular Biology, vo. 1597, Humana Press, New York, NY, 2017, 11 pgs.
Munera, J.O., et al., "Differentiation of Human Pluripotent Stem Cells into Colonic Organoids via Transient Activation of BMP Signaling," Cell Stem Cell, Jul. 2017, 21(1):51-64.e6, 21 pgs.
Rankin, S.A., et al., "Timing is everything: Reiterative Wnt, BMP and RA signaling regulate developmental competence during endoderm organogenesis," Developmental Biology, Feb. 1, 2018, 434(1):121-132, 12 pgs.
Workman, M.J., et al., "Engineered human pluripotent-stem-cell-derived intestinal tissues with a functional enteric nervous system," Nat Med, Jan. 2017, 23(1):49-59, 29 pgs.

(56) References Cited

OTHER PUBLICATIONS

Zachos, N.C., et al., "Human Enteroids/Colonoids and Intestinal Organoids Functionally Recapitulate Normal Intestinal Physiology and Pathophysiology," The Journal of Biological Chemistry, Feb. 2016, 291(8):3759-3766, 8 pgs.
International Search Report and Written Opinion dated Feb. 21, 2018 for Application No. PCT/US2017/064600, 15 pgs.
Singaporean Second Written Opinion dated Sep. 4, 2018 for Application No. SG11201609953X, 6 pgs.
Deward, A.D., et al., "Cellular Heterogeneity in the Mouse Esophagus Implicates the Presence of a Nonquiescent Epithelial Stem Cell Population," Cell Reports, 2014, 9:701-711, 12 pgs.
Trisno, S.L., et al., "Esophageal Organoids from Human Pluripotent Stem Cells Delineate Sox2 Functions during Esophageal Specification," Cell Stem Cell, 2018, 23:501-515, 23 pgs.
International Search Report and Written Opinion dated Jan. 8, 2019 for Application No. PCT/US2018/054635, 16 pgs.
Aimera, V., et al., "Novel Plasma Biomarkers Associated with Liver Disease Seventy in Adults with Nonalcoholic Fatty Liver Disease," Hepatology, 2017, 65(1):65-77, 21 pgs.
Aleo, M.D., et al., "Human Drug-Induced Liver Injury Severity is Highly Associated with Dual Inhibition of Liver Mitochondrial Function and Bile Salt Export Pump," Hepatology, 2014, 60:1015-1022, 8 pgs.
Allard, J., et al., "Immunohistochemical toolkit for tracking and quantifying xenotransplanted human stem cells," Regenerative Medicine, 2014, 9(4):437-452, 11 pgs.
Arroyo, J.D., et al., "Argonaute2 complexes carry a population of circulating microRNAs independent of vesicles in human plasma," PNAS, 2011, 108(12):5003-5008, 6 pgs.
Bahar Halpern, K., et al. "Single-cell spatial reconstruction reveals global division of *labour in the mammalian liver*," Nature, 2017, 542:352-356, 18 pgs.
Bar-Ephraim, Y.E., et al., "Modelling cancer immunomodulation using epithelial organoid cultures," bioRxiv, 2018, accessed from Http://dx.doi.org/10.1101/377655v1.full, 13 pgs.
Barth, C.A., et al., "Transcellular transport of fluorescein in hepatocyte monolayers: Evidence for functional polarity of cells in culture," Proc Natl Acad Sci USA, 1982, 79:4985-4987, 3 pgs.
Begriche, K., et al., "Drug-induced toxicity on mitochondria and lipid metabolism: Mechanistic diversity and deleterious consequences for the liver," J Hepatol, 2011, 54:773-794, 22 pgs.
Bell, L.N., et al., "Epidemiology of Idiosyncratic Drug-Induced Liver Injury," Semin Liver Dis, 2009, 29(4):337-347, 11 pgs.
Bergeles, C., et al., "From Passive Tool Holders to Microsurgeons: Safer, Smaller, Smarter Surgical Robots," IEEE Trans Biomed Eng, 2014, 61(5):1565-1576, 12 pgs.
Bernardi, P., "The permeability transition pore. Control points of a cyclosporin A-sensitive mitochondrial channel involved in cell death," Biochim Biophys Acta, 1996, 1275:5-9, 5 pgs.
Bharadwaj, S., et al., "Current status of intestinal and multivisceral transplantation," Gastroentrerol Rep (Oxf)., 2017, 5(1):20-28, 9 pgs.
Bhutani, N., et al., Reprogramming towards pluripotency requires AID-dependent DNA demethylation, Nature, 2010, 463(7284):1042-1047, 17 pgs.
Bohan, T.P., et al., "Effect of L-carnitine treatment for valproate-induced hepatotoxicity," Neurology, 2001, 56:1405-1409, 5 pgs.
Boroviak, T., et al., "Single cell transcriptome analysis of human, marmoset and mouse embryos reveals common and divergent features of preimplantation development," Development, 2018, 145(21):dev167833, 35 pgs.
Bort, R., et al., "Dielofenae Toxicity to Hepatoeytes: A Role for Drug Metabolism in Cell Toxicity," J Pharmacol Exp Ther, 1998, 288(1):65-72, 8 pgs.
Boullata, J.I., et al. "A.S.P.E.N. Clinical Guidelines: Parenteral Nutrition Ordering, Order Review, Compounding, Labeling, and Dispensing," J Parenter Enteral Nutr, 2014, 38(3):334-377, 44 pgs.
Bragdon, B., et al., "Bone Morphogenetie Proteins: A critical review," Cellular Signalling, 2011, 23:609-620, 12 pgs.

Bravo, P., et al., "Efficient In Vitro Vectorial Transport of a Fluorescent Conjugated Bile Acid Analogue by Polarized Hepatic Hybrid WIF-B and WIF-B9 Cells," Hepatology, 1998, 27:576-583, 8 pgs.
Browning, J.D., et al., "Molecular mediators of hepatic steatosis and liver injury," J Clin Invest, 2004, 114(2):147-152, 6 pgs.
Burke, P., et al., "Towards a single-chip, implantable RFID system: is a single-cell radio possible?" Biomed Microdevices, 2010, 12:589-596, 8 pgs.
Burn, S.F., et al., "Left-right asymmetry in gut development: What happens next?" BioEssays, 2009, 31:1026-1037, 12 pgs.
Caneparo, L., et al., "Intercellular Bridges in Vertebrate Gastrulation," PloS ONE, 2011, 6(5):e20230, 6 pgs.
Capeling, M.M., et al., "Nonadhesive Alginate Hydrogels Support Growth of Pluripotent Stem Cell-Derived Intestinal Organoids," Stem Cell Reports, Feb. 2019, 12(2):381-394, 14 pgs.
Chai, P.R., et al., "Utilizing an Ingestible Biosensor to Assess Real-Time Medication Adherence," J Med Toxicol, 2015, 11:439-444, 6 pgs.
Chai, P.R., et al., "Ingestible Biosensors for Real-Time Medical Adherence Monitoring: MyTMed," Proc Annu Hawaii Int Conf Syst Sci, Jan. 2016, 2016:3416-3423, 12 pgs.
Chang, J.H., et al., "Evaluating the In Vitro Inhibition of UGT1A1, OATP1B1, OATP1B3, MRP2, and BSEP in Predicting Drug-Induced Hyperbilirubinemia," Mol Pharm, 2013, 10:3067-3075, 9 pgs.
Chatterjee, S., et al., "Hepatocyte-based in vitro model for assessment of drug-induced cholestasis." Toxicol Amol Pharmacol, 2014, 274:124-136, 13 pgs.
Chen, B., et al., "Dynamic Imaging of Genomic Loci in Living Human Cells by an Optimized CRISPR/Cas System," Cell, 2013, 155(7):1479-1491, 23 pgs.
Chen, L.Y., et al., "Mass fabrication and delivery of 3D multilayer µTags into living cells," Sci Rep, 2013, 3:2295, 6 pgs.
Chen, Y., et al., "Retinoic acid signaling is essential for pancreas development and promotes endocrine at the expense of exocrine cell differentiation in *Xenopus*," Dev Biol, 2004, 271:144-160, 17 pgs.
Christofpersson, J., et al., "Developing organ-on-a-chip concepts using bio-mechatronic design methodology," Biofabrication, 2017, 9:025023, 14 pgs.
Chughlay, M.F., et al., "N-acetyleysteine for non-paracetamol drug-induced liver injury: a systematic review," Br J Clin Pharmacol, 2016, 81:1021-1029, 9 pgs.
Clarke, L.L., "A guide to Ussing chamber studies of mouse intestine," Am J Physiol Gastrointest Liver Physiol, 2009, 296:G1151-G1166, 16 pgs.
Collier, A.J., et al., "Comprehensive Cell Surface Protein Profiling Identifies Specific Markers of Human Naïve and Primed Pluripotent States," Cell Stem Cell, 2017, 20:874-890, 25 pgs.
Cortez, et al., "Transplantation of human intestinal organoids into the mouse mesentery: A more physiological and anatomic engraftment site," Surgery, 2018, 164:643-650, 8 pgs.
Crocenzi, F.A., et al., "$Ca^{2+}$-Dependent Protein Kinase C Isoforms Are Critical to Estradiol 17β-D-Glucuronide-Induced Cholestasis in the Rat," Hepatology, 2008, 48:1885-1895, 12 pgs.
Cutrin, J.C., et al., "Reperfusion Damage to the Bile Canalieuli in Transplanted Human Liver," Hematology, 1996, 24:1053-1057, 5 pgs.
Das, R., "RFID Forecasts, Players and Opportunities 2017-2027," IDTeehEx, 2017, downloaded from https://www.idtechex.com/en/researeh-report/rfid-forecasts-players-and-opportunities-2017-2027/546, 8 pgs. Summary only.
Dash, A., et al., "Pharmacotoxicology of clinically-relevant concentrations of obeticholic acid in an organotypic human hepatocyte system," Toxicology In Vitro, 2017, 39:93-103, 11 pgs.
Davidson, M.D., et al., "Long-term exposure to abnormal glucose levels alters drug metabolism pathways and insulin sensitivity in primary human hepatoeytes," Sci Rep, 2016, 6:28178, 11 pgs.
Dekkers, J.F., et al., "A functional CFTR assay using piimary cystic fibrosis intestinal organoids," Nat Med, 2013, 19(7):939-945, 9 pgs.
Demehri, F.R., et al., "Development of an endolurninal intestinal attachment for clinically applicable distraction enterogenesis device," Journal of Pediatric Surgery, 2016, 51:101-106, 6 pgs.

(56) References Cited

OTHER PUBLICATIONS

Demehri, F.R., et al., "Development of an endoluminal intestinal lengthening device using a geometric intestinal attachment approach," Surgery, 2015, 158(3):802-811, 10 pgs.

Dumortier, G., et al., "Tolérance hépatique des antipsychotiques atypiques, [Hepatic tolerance of atypical antipsychotic drugs]," L'Encéphale, 2002, 28(1):542-551, 10 pgs.

Dvir-Ginzberg, M., et al., "Liver Tissue Engineering Within Alginate Scaffolds: Effects of Cell-Seeding Density on Hepatocyte Viability, Morphology, and Function," Tissue Eng, 2003, 9(4):757-766, 10 pgs.

Edling, Y., et al., "Increased sensitivity for troglitazone-induced cytotoxicity using a human in vitro co-culture model," Toxicol In Vitro, 2009, 23:1387-1395, 9 pgs.

Ekser, B., et al., "Comparable outcomes in intestinal retransplantation: Single-center cohort study," The Journal of Clinical and Translational Research, 2018, 32(7):e13290, 10 pgs.

El Kasmi, K.C., et al., "Phytosterols Promote Liver Injury and Kupffer Cell Activation in Parenteral Nutrition-Associated Liver Disease," Sci Transl Med, 2013, 5(206):206ra137, 10 pgs.

El Taghdouini, A., et al., "In vitro reversion of activated primary human hepatic stellate cells," Fibrogenesis & Tissue Repair, 2015, 8:14, 15 pgs.

The Encode Project Consortium, "An integrated encyclopedia of DNA elements in the human genome," Nature, 2012, 489:57-74, 18 pgs.

Engmann, J., et al., "Fluid mechanics of eating, swallowing and digestion—overview and perspectives," Food & Function, 2013, 4:443-447, 5 pgs.

Fahrmayr, C., et al., "Phase I and II metabolism and MRP2-mediated export of bosentan in a MDCKII-OATP1B1-CYP3A4-UGT1A1-MRP2 quadruple-transfected cell line," Br J Phatmacol, 2013, 169:21-33, 13 pgs.

Falasca, L., et al., "The effect of retinoic acid on the re-establishment of differentiated hepatocyte phenotype in primary culture," Cell Tissue Res, 1998, 293:337-347, 11 pgs.

Finkenzeller, K., *RFID Handbook: Fundamentals and Applications in Contactless Smart Cards, Radio Frequency Identification and Near-Field Communication, Third Edition*. John Wiley & Sons, Ltd., Chichester, West Sussex, 2010, 8 pgs. (Table of Contents Only).

Fisher, A., et al., "Entacapone-Induced Hepatotoxicity and Hepatic Dysfunction," Mov Disord, 2002, 17:1362-1365, 4 pgs.

Fromenty, B., "Drug-induced liver injury in obesity," J Hepatol, 2013, 58:824-826, 3 pgs.

Gafni, O., et al., "Derivation of novel human ground state naïve pluripotent stem cells," Nature, 2013, 504:282-286, 20 pgs.

Geerts, A., et al., "Formation of Normal Desmin Intermediate Filaments in Mouse Hepatic Stellate Cells Requires Vimentin," Hepatology, 2001, 33:177-188, 12 pgs.

Gerdes, H-H., et al., "Tunneling nanotubes, an emerging intercellular communication route in development," 2013, 130:381-387, 7 pgs.

Giles, D.A., et al., "Thermoneutral housing exacerbates nonalcoholic fatty liver disease in mice and allows for sex-independent disease modeling," Nature Medicine, 2017, 23(7):829-838, 13 pgs.

Glorioso, J.M., et al., "Pivotal Preclinical Trial of the Spheroid Reservoir Bioartificial Liver," J Hepatol, 2015, 63(2):388-398, 27 pgs.

Gomez-Pinilla, P.J., et al., "Ano1 is a selective marker of interstitial cells of Cajal in the human and mouse gastrointestinal tract," Am J Physiol Gastrointest Liver Physiol, 2009, 296:G1370-G1381, 12 pgs.

Grapin-Botton, A., "Three-dimensional pancreas organogenesis models," Diabetes Obes Metab, 2016, 18(Suppl 1):33-40, 8 pgs.

Gregersen, H., et al., "The Zero-Stress State of the Gastrointestinal Tract: Biomechanical and Functional Implications," Digestive Diseases and Sciences, 2000, 45(12):2271-2281, 11 pgs.

Guo, G., et al., "Epigenetic resetting of human pluripoteney," Development, 2017, 144:2748-2763, 17 pgs.

Gurdon, J.B., "Adult Frogs Delived from the Nuclei of Single Somatic Cells," Dev Biol, 1962, 4:256-273, 18 pgs.

Gurken, A., "Advances in small bowel transplantation," Turk J Surg., 2017, 33(3):135-141, 7 pgs.

Haimovich, G., et al., "Intercellular mRNA trafficking via membrane nanotube-like extensions in mammalian cells," 2017, PNAS, pp. E9873-E9882, 10 pgs.

Han, B., et al., "Microbiological safety of a novel bio-artificial liver support system based on porcine hepatocytes: a experimental study," European Journal of Medical Research, 2012, 17:13, 8 pgs.

Hassan, W., et al., "Reduced Oxidative Stress Conttibutes to the Lipid Lowering Effects of Isoquercitrin in Free Fatty Acids Induced Hepatocytes," Oxid Med Cell Longev, 2014, 313602, 18 pgs.

Heidari, R., et al., "Factors affecting drug-induced liver injury: antithyroid drugs as instances," Clin Mol Hepatol, 2014, 20:237-248, 12 pgs.

Hernandez, F., et al., "Refining Indications for Intestinal Retransplantation," International Small Bowel Symposium 2013; Abstract 12.241 (online: https://www.tts.org/component/%20tts/?view=presentation&id=13241) Accessed Jun. 12, 2017, 3 pgs.

Hooton, D., et al., "The Secretion and Action of Brush Border Enzymes in the Mammalian Small Intestine," Rev Physiol Biochem Pharmacol, 2015, 168:59-118, 60 pgs.

Hou, P., et al., "Pluripotent Stem Cells Induced from Mouse Somatic Cells by Small-Molecule Compounds," Science, 2013, 341:651-654, 4 pgs.

Hsu, F., et al., "The UCSC Known Genes," Bioinformatics, 2006, 22(9):1036-1046, 11 pgs.

Hu, H., et al., "Long-Term Expansion of Functional Mouse and Human Hepatocytes as 3D Organoids," Cell, 2018, 175:1591-1606, 36 pgs.

Hu, X., et al., "Micrometer-Scale Magnetic-Resonance-Coupled Radio-Frequency Identification and Transceivers for Wireless Sensors in Cells," Physical Review Applied, 2017, 8:014031, 13 pgs.

Huch, M., et al., "Long-Term Culture of Genome-Stable Bipotent Stem Cells from Adult Human Liver," Cell, 2015, 160:299-312, 14 pgs.

Hynds, R.E., et al., "The relevance of human stem cell-derived organoid models for epithelial translational medicine," Stem Cells, 2013, 31(3):417-422, 11 pgs.

Ijpenberg, A., et al., "Wt1 and retinoic acid signaling are essential for stellate cell development and liver morphogenesis," Dev Biol, 2007, 312:157-170, 14 pgs.

Inoue, H., et al., "iPS cells: a game changer for future medicine," EMBO J, 2014, 33(5):409-417, 9 pgs.

Ito, K., et al., "Temporal Transition of Mechanical Characteristics of HUVEC/MSC Spheroids Using a Microfluidic Chip with Force Sensor Probes," Micromachines, 2016, 7:221, 14 pgs.

Jalan-Sakrikar, N., et al., "Hedgehog Signaling Overcomes an EZH2-Dependent Epigenetic Barrier to Promote Cholangiocyte Expansion," PLoS One, 2016, 11(12):e0168266, 19 pgs.

Kanuri, G., et al., "In Vitro and in Vivo Models of Non-Alcoholic Fatty Liver Disease (NAPLD)," Int J Mol Sci, 2013, 14:11963-11980, 18 pgs.

Karlikow, M., et al., "*Drosophila* cells use nanotube-like structures to transfer dsRNA and RNAi machinery between cells," Scientific Reports, 2016, 6:27085, 9 pgs.

Keitel, V., et al., "De Novo Bile Salt Transporter Antibodies as a Possible Cause of Recurrent Graft Failure After Liver Transplantation: A Novel Mechanism of Cholestasis," Hepatology, 2009, 50:510-517, 8 pgs.

Kelly, G.M., et al., "Retinoic Acid and the Development of the Endoderm," J Dev Biol. 2015, 3:25-56, 32 pgs.

Khan, F.A., et al., "Overview of intestinal and multivisceral transplantation," UpToDate, Sep. 2018 [online: https://www.uptodate.com/contents/overview-of-intestinal-and-multivisceral-transplantation/print], 32 pgs.

Kilens, S., et al., "Parallel derivation of isogenic human primed and naïve induced pluripotent stem cells." Nat Commun, 2018, 9:360, 13 pgs.

Kilpinen, H., et al., "Common genetic variation drives molecular heterogeneity in human iPSCs," Nature, 2017, 546(7658):370-375, 51 pgs.

(56) References Cited

OTHER PUBLICATIONS

Kim, D., et al., "HISAT: a fast spliced aligner with low memory requirements," Nature Methods, 2015, 12(4):357-360, 6 pgs.
Kock, K., et al., "A Perspective on Efflux Transport Proteins in the Liver," Clin Pharmacol Ther, 2012, 92(5):599-612, 29 pgs.
Koehler, E.M, et al., "Presence of Diabetes Mellitus and Steatosis Is Associated With Liver Stiffness In A General Population: The Rotterdam Study," Hepatology, 2016, 63:138-147, 10 pgs.
Kolodny, G.M., "Evidence for Transfer of Macromolecular RNA Between Mammalian Cells in Culture." Exp Cell Res, 1971, 65:313-324, 12 pgs.
Kordes, C., et al., "Hepatic stellate cells contribute to progenitor cells and liver regeneration," J Clin Invest, 2014, 124(12):5503-5515, 13 pgs.
Krähenbühl, S., et al., "Toxicity of Bile Acids on the Electron Transport Chain of Isolated Rat Liver Mitochondria," Hepatology, 1994, 19:471-479, 9 pgs.
Kubal, C.A., et al., "Challenges with Intestine and Multivisceral Re-Transplantation: Importance of Timing of Re-Transplantation and Optimal Immunosuppression," Ann Transplant, 2018, 23:98-104, 7 pgs.
Kullak-Ublick, G.A., et al., "Drug induced liver injury: recent advantages in diagnosis and risk assessment," Gut, 2017, 66:1154-1164, 11 pgs.
Kumar, J.A., et al., "Controversies in the Mechanism of Total Parenteral Nutrition Induced Pathology," Children, 2015, 2:358-370, 13 pgs.
Kurpios, N.A., et al., "The direction of gut looping is established by changes in the extracellular matrix and in cell:cell adhesion," PNAS, 2008, 105(25):8499-8506, 8 pgs.
Lê, S., et al., "FactoMineR: An R Package for Multivariate Analysis," Journal of Statistical Software, 2008, 25(1):1-18, 18 pgs.
Le Vee, M., et al., "Polarized expression of drug transporters in differentiated human hepatoma HepaRG cells," Toxicol In Vitro, 2013, 27:1979-1986, 8 pgs.
Lechner, C., et al., "Development of a fluorescence-based assay for drug interactions with human Multidrug Resistance Related Protein (MRP2; ABCC2) in MDCKII-MRP2 membrane vesicles," Eur J Pharm Biopharm, 2010, 75:284-290, 7 pgs.
LEE, W.M., et al., "Intravenous N-Acetyleysteine Improves Transplant-Free Survival In Early Stage Non-Acetaminophen Acute Liver Failure," Gastroenterology, 2009, 137(3):856-864, 18 pgs.
Leslie, E.M., et al., "Differential Inhibition of Rat and Human $Na^+$-Dependent Taurocholate Cotransporting Polypeptide (NTCP/SLC10A1) by Bosentan: A Mechanism for Species Differences in Hepatotoxicity," J Pharmacol Exp Ther, 2007, 321(3):1170-1178, 9 pgs.
Leung, A.A., et al., "Tolerance testing of passive radio frequency identification tags for solvent, temperature, and pressure conditions encountered in an anatomic pathology or biorepository setting," J Pathol Inform, 2010, 1:21, 6 pgs.
Li, N., et al., "A Systematic Assessment of Mitochondrial Function Identified Novel Signatures for Drug-Induced Mitochondrial Disruption in Cells," Toxicol Sci, 2014, 142(1):261-273, 13 pgs.
Lin, Y., et al., "Differentiation, Evaluation, and Application of Human Induced Pluripotent Stem Cell-Derived Endothelial Cells," Arterioscler Thromb Vasc Biol, 2017, 37:2014-2025, 12 pgs.
Liu, L., et al., "A Review of Locomotion Systems for Capsule Endoscopy," IEEE Rev Biomed Eng, 2015, 8:138-151, 14 pgs.
Loike, J.D., et al., "Opinion: Develop Organoids, Not Chimeras, for Transplantation," The Scientist Magazine, Aug. 2019, (online: http://www.the-scientist.com/news-opinion/opinion--develop-organoids--not-chimeras--for-transplantation-66339), 3 pgs.
Love, M.I., et al., "Moderated estimation of fold change and dispersion for RNA-seq data with DESeq2," Genome Biol, 2014, 15:550, 21 pgs.
Low, L.A., et al., "Organs-on-chips: Progress, challenges, and future directions," Experimental Biology and Medicine, 2017, 242:1573-1578, 6 pgs.

Luntz, J., et al., "Mechanical Extension Implants for Short-Bowel Syndrome," Smart Structures and Materials 2006: Smart Structures and Integrated Systems, Proc of SPIE, 2006, 6173:617309-1-617309-11, 11 pgs.
MacParland, S.A., et al., "Single cell RNA sequencing of human liver reveals distinct intrahepatic macrophage populations," Nat Commun 2018, 9:4383, 21 pgs.
Mahe, M.M., et al., "In Vivo Model of Small Intestine," Methods Mol Biol, 2017, 1597:229-245, 17 pgs.
Makin, A.J., et al., "A 7-Year Experience of Severe Acetaminophen-Induced Hepatotoxicity (1987-1993)," Gastroenterology, 1995, 109:1907-1916, 10 pgs.
Malinen, M.M., et al., "Differentiation of liver progenitor cell line to functional organotypic cultures in 3D nanofibrillar cellulose and hyaluronan-gelatin hydrogels," Biomaterials, 2014, 35:5110-5121, 12 pgs.
Mammoto, A., et al., "Mechanosensitive mechanisms in transcriptional regulation," Journal of Cell Science, 2012, 125:3061-3073, 13 pgs.
Marcum, Z.A., et al., "Medication Adherence to Multi-Drug Regimens," Clin Geriatr Med, 2012, 28(2):287-300, 15 pgs.
Marini, F., et al., "pcaEXplorer: an R/Bioconductor package for interacting with RNA-seq principal components," BMC Bioinformatics, 2019, 20:331, 8 pgs.
Marini, F., "pcaExplorer: Interactive Visualization of RNA-seq Data Using a Principal Components Approach," bioconductor.org, R package version 2.3.0, 2017, 7 pgs.
Markova, S.M., et al., "Association of CYP2C9*2 With Bosentan-Induced Liver Injury." Clin Phatmacol Ther., Dec. 2013, 94(6):678-86, 9 pgs.
Marsh, M.N., et al., "A study of the small intestinal mucosa using the scanning electron microscope," Gut, 1969, 10:940-949, 10 pgs.
McCracken, K.W., et al., "Erratum: Wnt/β-catenin promotes gastric fundus specification in mice and humans." Nature, 2017, 543:136, 1 pg.
McKenzie, T.J., et al., "Artificial and Bioartificial Liver Support," Seminars in Liver Disease, 2008, 28(2):210-217, 8 pgs.
Mercaldi, C.J., et al., "Methods to Identify and Compare Parenteral Nutrition Administered From Hospital-Compounded and Premixed Multichamber Bags in a Retrospective Hospital Claims Database," J Parenter Enteral Nutr, 2012, 36(3):330-336, 7 pgs.
Michaut, A., et al., "A cellular model to study drug-induced liver injury in nonalcoholic fatty liver disease: application to acetaminophen," Toxicol Appl Pharmacol, 2016, 292:40-55, 35 pgs.
Miki, T., et al., "Hepatic Differentiation of Human Embryonic Stem Cells Is Promoted by Three-Dimensional Dynamic Perfusion Culture Conditions," Tissue Eng: Part C Methods, 2011, 17(5):557-568, 12 pgs.
Mörk, L.M., et a., "Comparison of Culture Media for Bile Acid Transport Studies in Primary Human Hepatocytes." J Clin Exp Hepatol, 2012, 2:315-322, 8 pgs.
Nakamura, T., et al., "Advancing Intestinal Organoid Technology Toward Regenerative Medicine." Cell Mol Gastroenterol Henatol, 2018, 5:51-60, 10 pgs.
Navarro, V.J., et al., "Drug-Related Hepatotoxicity," N Engl J Med, 2006, 354:731-739, 9 pgs.
Negishi, T., et al., "Retinoic Acid Signaling Positively Regulates Liver Specification by Inducing wnt2bb Gene Expression in Medaka," Hepatology, 2010, 51:1037-1045, 9 pgs.
Nelson, al., et al., "Microrobots for Minimally Invasive Medicine," Annual Review of Biomedical Engineering, 2010, 12(12):55-85, 33 pgs.
Nelson, C.M., "On Buckling Morphogenesis," J Biomech Eng, 2016, 138:021005-1-021005-6, 6 pgs.
Ni, X., et al., "Functional human induced hepatocytes (hiHeps) with bile acid synthesis and transport capacities: A novel in vitro cholestatic model," Sci Rep, 2016, 6:38694, 16 pgs.
Nishida, T., et al., "Rat liver canalicular membrane vesicles contain an ATP-dependent bile acid transport system," Proc Natl Acad Sci USA, 1991, 88:6590-6594, 5 pgs.
Oorts, M., et al., "Drug-induced cholestasis risk assessment in sandwich-cultured human hepatocytes," Toxicol In Vitro, 2016, 34:179-186, 8 pgs.

(56) References Cited

OTHER PUBLICATIONS

Orso, G., et al., "Pediatric parenteral nutrition-associated liver disease and cholestasis: Novel advances in pathomechanisms-based prevention and treatment," Dig Liver Dis, 2016, 48:215-222, 8 pgs.
Ouchi, R., et al., "Modeling Steatohepatitis in Humans with Pluripotent Stem Cell-Derived Organoids." Cell Metabolism, Aug. 2019, 30:1-11, 17 pgs.
Pardal, M.L., et al., "Towards the Internet of Things: An Introduction to RFID technology," RFID Technology-Concepts, Applications, Challenges, Proceedings of the 4th International Workshop, IWRT 2010, In conjunction with ICEIS 2010, Funchal, Madeira, Portugal, Jun. 2010, pp. 69-78, 10 pgs.
Pastor, W.A., et al., "TFAP2C regulates transcription in human naïve pluripotency by opening enhancers," Nature Cell Biology, 2018, 20:553-564, 18 pgs.
Pereira, C.F., et al., "Heterokaryon-Based Reprograming of Human B Lymphocytes for Pluripotency Requires Oct4 but Not Sox2," PLoS Genet, 2008, 4(9):e1000170, 14 pgs.
Pessayre, D., et al., "Central role of mitochondria in drug-induced liver injury," Drug Metab Rev, 2012, 44(1):34-87, 54 pgs.
Pessayre, D., et al., "Mitochondrial involvement in drug-induced liver injury," in *Adverse Drug Reaction*, J. Uetrecht (ed.), Handb Exp Pharmacol 196, Springer-Verlag, Berlin, Germany, 2010, pp. 311-365, 55 pgs.
Poling, H.M., et al., "Mechanically induced development and maturation of human intestinal organoids in vivo." Nat Biomed Eng, 2018, 2(6):429-442, 31 pgs.
Polson, J., et al., "AASLD Position Paper: The Management of Acute Liver Failure," Hepatology, 2005, 41(5):1179-1197, 19 pgs.
Purton, L.E., et al., "All-trans retinoic acid enhances the long-term repopulating activity of cultured hematopoietic stem cells," Blood, 2000, 95:470-477, 8 pgs.
Rachek, L.I., et al., "Troglitazone, but not rosiglitazone, damages mitochondrial DNA and induces mitochondrial dysfunction and cell death in human hepatocytes," Toxicol Appl Pharmacol, 2009, 240(3):348-354, 17 pgs.
Ramirez-Weber, F-A., et al., "Cytonemes: Cellular Processes that Project to the Principal Signaling Center in *Drosophila* Imaginal Discs," Cell, 1999, 97:599-607, 9 pgs.
Rane, A., et al., "Drug Metabolism in the Human Fetus and Newborn Infant," Pediatr Clin North Am, 1972, 19(1):37-49, 11 pgs.
Rao, R.R., et al., "Gene Expression Profiling of Embryonic Stem Cells Leads to Greater Understanding of Pluripotency and Early Developmental Events," Biol Reprod, 2004, 71:1772-1778, 7 pgs.
Rector, R.S., et al., "Mitochondrial dysfunction precedes insulin resistance and hepatic steatosis and contributes to the natural history of non-alcoholic fatty liver disease in an obese rodent model," J Hepatol, 2010, 52(5):727-736, 20 pgs.
Reuben, A., et al. "Drug-Induced Acute Liver Failure: Results of a U.S. Multicenter, Prospective Study," Hepatology, 2010, 52:2065-2076, 12 pgs.
Riedinger, H-J, et al., "Reversible shutdown of replicon initiation by transient hypoxia in Ehrlich ascites cells: Dependence of initiation on short-lived protein," Eur J. Biochem, 1992, 210:389-398, 10 pgs.
Roberts, A., et al., "Identification of novel transcripts in annotated genomes using RNA-Seq," Bioinformatics, 2011, 27(17):2325-2329, 5 pgs.
Roberts, A., et al., "Improving RNA-Seq expression estimates by correcting for fragment bias," Genome Biol, 2011, 12:R22, 14 pgs.
Ronn, R.E., et al., "Retinoic Acid Regulates Hematopoietic Development from Human Pluripotent Stem Cells," Stem Cell Reports, 2015, 4:269-281, 13 pgs.
Rouch, J.D., et al., "Scalability of an endoluminal spring for distraction enterogenesis." Journal of Pediatric Surgery, 2016, 51:1988-1992, 5 pgs.
Roy, S., et al., "Cytoneme-Mediated Contact-Dependent Transport of the *Drosophila* Decapentaplegic Signaling Protein." Science, 2014, 343:1244624-1, 11 pgs.

Russo, M.W., et al., "Liver Transplantation for Acute Liver Failure From Drug Induced Liver Injury in the United States," Liver Transpl, 2004, 10:1018-1023, 6 pgs.
Sachs, N., et al., "A Living Biobank of Breast Cancer Organoids Captures Disease Heterogeneity," Cell, 2018, 172:373-386, 25 pgs.
Saini, A., "Cystic Fibrosis Patients Benefit from Mini Guts," Cell Stem Cell, 2016, 19:425-427, 3 pgs.
Salas-Vidal, E., et al., "Imaging filopodia dynamics in the mouse blastoeyst," Developmental Biology, 2004, 265:75-89, 15 pgs.
Sartori-Rupp, A., et al., "Correlative cryo-electron microscopy reveals the structure of TNTs in neuronal cells," Nature Communications, 2019, 10:342, 16 pgs.
Sasai, Y., "Cytosystems dynamics in self-organization of tissue architecture," Nature, 2013, 493:318-326, 9 pgs.
Sato, T., et al., "Snapshot: Growing Organoids from Stem Cells," Cell, 2015, 161:1700-1700e1, 2 pgs.
Serviddio, G., et al., "Ursodeoxycholic Acid Protects Against Secondary Biliary Cirrhosis in Rats by Preventing Mitochondrial Oxidative Stress," Hepatology, 2004, 39:711-720, 10 pgs.
Shahbazi, M.N., et al., "Self-organization of the human embryo in the absence of maternal tissues," Nature Cell Biology, 2016, 18(6):700-708, 20 pgs.
Shekherdimian, S., et al., "The feasibility of using an endoluminal device for intestinal lengthening," Journal of Pediatric Surgery, 2010, 45:1575-1580, 6 pgs.
Shi, X-L., et al., "Effects of Membrane Molecular Weight Cutoff on Performance of a Novel Bioartificial Liver," Artificial Organs, 2011, 35(3):E40-E46, 7 pgs.
Shi, X-L., et al., "Evaluation of a novel hybrid bioartificial liver based on a multi-layer flat-plate bioreactor," World J Gastroenterol, 2012, 18(28):3752-3760, 9 pgs.
Shyer, A.E., et al., "Villification: How the Gut Gets its Villi," Science, 2013, 342:212-218, 7 pgs.
Sim, Y-J., et al., "2i Maintains a Naive Ground State in ESCs through Two Distinct Epigenetic Mechanisms," Stem Cell Reports, 2017, 8:1312-1328, 17 pgs.
Sitti, M., et al., "Biomedical Applications of Untethered Mobile Milli/Microrobots," Proc IEEE Inst Electr Electron Eng, 2015, 103(2):205-224, 20 pgs.
Slaymaker, I.M., et al., "Rationally engineered Cas9 nucleases with improved specificity," Science, 2016, 351(6268):84-88, 10 pgs.
Sloan, C.A., et al., "Encode data at the Encode portal," Nucleic Acids Res, 2016, 44:D726-D732, 7 pgs.
Sneddon, I.N., "The Relation Between Load and Penetration in the Axisymmetric Boussinesq Problem for a Punch of Arbitrary Profile," Int. J. Engng. Sci, 1965, 3:47-57, 11 pgs.
Soffers, J.H.M., et al., "The growth pattern of the human intestine and its mesentery," BMC Dev Biol, 2015, 15:31, 16 pgs.
Song, W., et al., "Engraftment of human induced pluripotent stem cell-derived hepatocytes in immunocompetent mice Via 3D co-aggregation and encapsulation," Sci Rep, 2015, 5:16884, 13 pgs.
Song, Z., et al., "Efficient generation of hepatocyte-like cells from human induced pluripotent stem cells." Cell Res, 2009, 19:1233-1242, 10 pgs.
Spence, J.R., et al., "Vertebrate Intestinal Endodenn Development," Developmental Dynamics, 2011, 240:501-520, 20 pgs.
Stafford, D., et al., "A conserved role for retinoid signaling in vertebrate pancreas development," Dev Genes Evol, 2004, 214:432-441, 10 pgs.
Stender, S., et al., "Adiposity Amplifies the Genetic Risk of Fatty Liver Disease Conferred by Multiple Loci," Nat Genet, 2017, 49(6):842-847, 18 pgs.
Stevens, J.L., et al., "The future of drug safety testing: expanding the view and narrowing the focus," Drug Discov Today, 2009, 14(3/4):162-167, 6 pgs.
Stuart, T., et al., "Comprehensive Integration of Single-Cell Data," Cell, 2019, 177:1888-1902, 37 pgs.
Sugimoto, S., et al., "Reconstruction of the Human Colon Epithelium In Vivo," Cell Stem Cell, 2018, 22: 171-176, 16 pgs.
Suzuki, A., et al., "Clonal identification and characterization of self-renewing pluripotent stem cells in the developing liver," The Journal of Cell Biology, 2002, 156(1):173-184, 12 pgs.

(56) References Cited

OTHER PUBLICATIONS

Tada, M., et al., "Embryonic germ cells induce epigenetic reprogramming of somatic nucleus in hybrid cells," EMBO J, 1997, 16(21):6510-6520, 11 pgs.
Takahashi, S., et al., "Epigenetic differences between naïve and primed pluripotent stem cells," Cellular and Molecular Life Sciences, 2018, 75:1191-1203, 13 pgs.
Takashima, Y., et al., "Resetting Transcription Factor Control Circuitry toward Ground-State Pluripotency in Human," Cell, 2014, 158(6):1254-1269, 32 pgs.
Takebe, T., et al., "Human iPSC-Derived Miniature Organs: A Tool for Drug Studies," Clin Pharmacol Ther, 2014, 96(3):310-313, 4 pgs.
Takebe, T., et al., "Massive and Reproducible Production of Liver Buds Entirely from Human Pluripotent Stem Cells," Cell Reports, 2017, 21:2661-2670, 11 pgs.
Takebe, T., et al., "Vascularized and Complex Organ Buds from Diverse Tissues via Mesenchymal Cell-Driven Condensation," Cell Stem Cell, 2015, 16:556-565, 10 pgs.
Takebe, T., et al., "Vascularized and functional human liver from an iPSC-derived organ bud transplant," Nature, 2013, 499:481-484, 5 pgs.
Tamm, C., et al., "A Comparative Study of Protocols for Mouse Embryonic Stem Cell Culturing," PLoS ONE, 2013, 8(12):e81156, 10 pgs.
Tamminen, K., et al., "Intestinal Commitment and Maturation of Human Pluripotent Stem Cells Is Independent of Exogenous FGF4 and R-spondinl," PLOS One, Jul. 2015, 10(7):e0134551, 19 pgs.
Terry, B.S., et al., "Preliminary Mechanical Characterization of the Small Bowel for In Vivo Robotic Mobility." J. Biomech Eng, 2011, 133:091010-1-09101-7, 7 pgs.
The WNT homepage, "Small molecules in Wnt signalling," Nusse Lab, Jan. 2019, 2 pgs.
Theunissen, T.W., et al., "Systematic Identification of Culture Conditions for Induction and Maintenance of Naïve Human Pluripotency," Cell Stem Cell, 2014, 15:471-487, 47 pgs.
Tian, X., et al., "Modulation of Multidrug Resistance-Associated Protein 2 (Mrp2) and Mrp3 Expression and Function with Small Interfering RNA in Sandwich-Cultured Rat Hepatocytes," Mol Pharmacol, 2004, 66(4):1004-1010, 7 pgs.
Tran, K., et al. "Evaluation of regional and Whole gut motility using the wireless motility capsule: relevance in clinical practice," Therap Adv Gastroenterol, 2012, 5(4):249-260, 12 pgs.
Trapnell, C., et al., "Transcript assembly and quantification by RNA-Seq reveals unannotated transcripts and isoform switching during cell differentiation," Nat Biotechnol, 2010, 28(5):511-515, 8 pgs.
Troy, D.B. (ed.), Remington: The Science and Practice of Pharmacy, $21^{st}$ Ed., 2006, Lippincott, Williams & Wilkens, Baltimore, MD, 6 pgs., Table of Contents Only.
Tsedensodnom, O., et al., "ROS: Redux and Paradox in Fatty Liver Disease," Hepatology, 2013, 58(4):1210-1212, 3 pgs.
Tsukada, N., et al., "The Structure and Organization of the Bile Canalicular Cytoskeleton With Special Reference to Actin and Actin-Binding Proteins," Hepatology, 1995, 21(4):1106-1113, 8 pgs.
Tyml, K., et al., "Lipopolysaccharide reduces intercellular coupling in vitro and arteriolar conducted response in vivo," AJP-Heart Circ Physiol, 2001, 281:H1397-H1406, 10 pgs.
The United States Pharmacopeia: The National Fonnulary (USP 24 NF 19), United States Pharmacopeial Convention, Inc., Rockville, MD, 1999, 4 pgs., Table of Contents Only.
Valadi, H., et al., "Exosome-mediated transfer of mRNAs and microRNAs is a novel mechanism of genetic exchange between cells," Nat Cell Biol, 2007, 9(6):654-659, 17 pgs.
Van De Garde, M.D., et al., "Liver Monoeytes and Kupffer Cells Remain Transcriptionally Distinct during Chronic Viral Infection," PLoS One, 2016, 11(11):e0166094, 16 pgs.
Venick, R.S., et al., "Unique Technical and Patient Characteristics of Retransplantation: A Detailed Single Center Analysis of Intestinal Transplantation," International Small Bowel Symposium 2013; Abstract 5.203 (online: https://www.tts.org/component/%20tts/?view=presentation&id=13190), Accessed Jun. 12, 2017, 4 pgs.
Verma, S., et al., "Diagnosis, management and prevention of drug-induced liver injury," Gut, 2009, 58:1555-1564, 10 pgs.
Vosough, M., et al., "Generation of Functional Hepatocyte-Like Cells from Human Pluripotent Stem Cells in a Scalable Suspension Culture," Stem Cells Dev, 2013, 22(20):2693-2705, 13 pgs.
Wakayama, T., et al., "Full-term development of mice from enucleated oocytes injected with cumulus cell nuclei," Nature, 1998, 394:369-374, 6 pgs.
Wang, S., (Ed.), "The role of homologous genes in the development of appendages," in Basis of Developmental Biology, Press of East China University of Science and Technology, 2014, pp. 184-185, 4 pgs.
Wang, Y., et al., "Hepatic stellate cells, liver innate immunity, and hepatitis C Virus," J Gastroenterol Hepatol, 2013, 28(Suppl 1):112-115, 8 pgs.
Want, R., "An Introduction to RFID Technology," IEEE Pervas Comput, 2006, 5:25-33, 9 pgs.
Ware, C.B., "Concise Review: Lessons from Naïve Human Pluripotent Cells," Stem Cells, 2017, 35:35-41, 7 pgs.
Warren, C.R., et al., "Induced Pluripotent Stem Cell Differentiation Enables Functional Validation of GWAS Variants in Metabolic Disease," Cell Stem Cell, 2017, 20:547-557, 18 pgs.
Warren, C.R., et al., "The NextGen Genetic Association Studies Consortium: A Foray into In Vitro Population Genetics," Cell Stem Cell, 2017, 20:431-433, 3 pgs.
Wernig, M., et al., "In vitro reprogramming of fibroblasts into a pluripotent ES-cell-like state," Nature, 2007, 448:318-324, 8 pgs.
Wieck, M.M., et al., "Prolonged Absence of Mechanoluminal Stimulation in Human Intestine Alters the Transcriptome and Intestinal Stem Cell Niche," Cell Mol Gastroenterol Hepatol, 2017, 3(3):367-388el, 23 pgs.
Wiley, L.A., et al., "cGMP production of patient-specific iPSCs and photoreceptors precursor cells to treat retinal degenerative blindness," Scientific Reports, 2016, 6:30742, 16 pgs.
Wilmut, I., et al., "Viable offspring derived from fetal and adult mammalian cells," Nature, 1997, 385:810-813, 4 pgs.
Xu, R., et al., "Association Between Patatin-Like Phospholipase Domain Containing 3 Gene (PNPLA3) Polymorphisms and Non-alcoholic Fatty Liver Disease: A HuGE Review and Meta-Analysis," Sci Rep, 2015, 5:9284, 11 pgs.
Xu, R., et al. (Eds), "Retinoic acid receptor" in Basis and Clinic of Receptor, Shanghai Science and Technology Press, 1992, pp. 129-131, 2 pgs.
Yanagimachi, M.D., et al., "Robust and Highly-Efficient Differentiation of Functional Monocytic Cells from Human Pluripotent Stem Cells under Serum- and Feeder Cell-Free Conditions." PLoS One, 2013, 8(4):e59243, 9 pgs.
Yang, K., et al., "Systems Pharmacology Modeling Predicts Delayed Presentation and Species Differences in Bile Acid-Mediated Troglitazone Hepatotoxicity," Clin Pharmacol Ther, 2014, 96(5):589-598, 21 pgs.
Yoneda, M., et al., "Noninvasive assessment of liver fibrosis by measurement of stiffness in patients with nonalcoholic fatty liver disease (NAFLD)," Dig Liver Dis, 2008, 40:371-378, 8 pgs.
Yu, H., et al., "The Contributions of Human Mini-Intestines to the Study of Intestinal Physiology and Pathophysiology," Annu Rev Physiol, 2017, 79:291-312, 22 pgs.
Zain, S.M., et al., "A common variant in the glucokinase regulatory gene rs780094 and risk of nonalcoholic fatty liver disease: A meta-analysis," J Gastroenterol Hepatol, 2015, 30:21-27, 7 pgs.
Zambrano, E., et al., "Total parenteral Nutrition Induced Liver Pathology: An Autopsy Series of 24 Newborn Cases," Pediatr Dev Pathol, 2004, 7:425-432, 8 pgs.
Zborowski, J., et al., "Induction of swelling of liver mitochondria by fatty acids of various chain length," Biochim Biophys Acta, 1963, 70:596-598, 3 pgs.
Zhang, R-R., et al., "Human iPSC-Derived Posterior Gut Pro genitors Are Expandable and Capable of Forming Gut and Liver Organoids," Stem Cell Reports, 2018, 10(3):780-793, 14 pgs.

(56) References Cited

OTHER PUBLICATIONS

Zhao, Y., et al., "A XEN-like State Bridges Somatic Cells to Pluripotency duting Chemical Reprogramming," Cell, 2015, 163:1678-1691, 15 pgs.

Zhong, J ., et al., "Continuous-wave laser-assisted injection of single magnetic nanobeads into living cells," Sensors and Actuators B: Chemical, 2016, 230:298-305, 8 pgs.

Chinese Office Action, the Second Office Action, and Supplementary Search Report, dated Dec. 19, 2019 for Application No. CN 2015800349104, 11 pgs.

International Search Report and Written Opinion dated Jul. 9, 2018 for Application No. PCT/US2018/027585, 12 pgs.

International Search Report and Written Opinion dated May 7, 2019 for Application No. PCT/US2018/067057, 15 pgs.

International Search Report and Written Opinion dated Oct. 29, 2019 for Application No. PCT/US2019/041985, 13 pgs.

International Search Report and Written Opinion dated Dec. 5, 2019 for Application No. PCT/US2019/050846, 10 pgs.

International Search Report and Written Opinion dated Dec. 13, 2019 for Application No. PCT/US2019/053408, 10 pgs.

U.S. Appl. No. 16/346,190, filed Apr. 30, 2019, by Takebe et al., entitled: "Liver Organoid Disease Models and Methods of Making and Using Same."

U.S. Appl. No. 16/599,620, filed Oct. 11, 2019, by Wells et al., entitled: "Methods and Systms for Converting Precursor Cells Into Intestinal Tissues Through Directed Differentiation."

U.S. Appl. No. 16/603,609, filed Oct. 8, 2019, by Takebe et al., entitled: "Multi Donor Stem Cell Compositions and Methods of Making Same."

U.S. Appl. No. 16/603,611, filed Oct. 8, 2019, by Mahe et al., entitled: "Methods of Making Improved Human Intestinal Organoid Compositions Via Application of Strain and Human Intestinal Organoid Compositions Thereof."

U.S. Appl. No. 16/611,998, filed Nov. 8, 2019, by Takebe et al., entitled: "Liver Organoid Compositions and Methods of Making and Using Same."

Ahnfelt-Ronne, J., et al., "An improved method for three-dimensional reconstruction of protein expression patterns in intact mouse and chicken embryos and organs," J. Histochem. Cytochem., 2007, 55:925-930, 6 pgs.

Aronson, B.E., et al., "GATA4 represses an ileal program of gene expression in the proximal small intestine by inhibiting the acetylation of histone H3, lysine 27," Biochim, Biophys. Acta, 2014, 1839(11):1273-1282, 31 pgs.

Bartfeld, S., et al., "In Vitro Expansion of Human Gastric Epithelial Stem Cells and Their Responses to Bacterial Infection," Gastroenterology, Jan. 2015, 148(1):126-136, 22 pgs.

Battle, M.A., et al., "GATA4 is essential for jejunal function in mice," Gastroenterology, 2008, 135:1676-1686, 17 pgs.

Bernstein, B.E., et al., "The NIH Roadmap Epigenomics Mapping Consortium," Nat Biotechnol. 2010; 28(10):1045-1048, 9 pgs.

Beuling, E., et al., "Co-Localization of Gata4 and Hnf1α in the Gastrointestinal Tract is Restricted to the Distal Stomach and Proximal Small Intestine," Gastroenterology, AGA Abstracts, Abstract T1933, 2007a, 132:A586, 1 pg.

Beuling, E., et al., "Conditional Gata4 deletion in mice induces bile acid absorption in the proximal small intestine," Gut, 2010, 59(7):888-895, 19 pgs.

Beuling, E., et al., "Fog Cofactors Partially Mediate Gata4 Function in the Adult Mouse Small Intestine," Gastroenterology, AGA Abstracts, Abstract W1467, 2007b, 132:A692-A693, 2 pgs.

Beuling, E., et al., "GATA4 mediates gene repression in the mature mouse small intestine through interactions with Friend of GATA (FOG) eofaetors," Dev Biol, 2008a, 322(1):179-189, 23 pgs.

Beuling, E., et al., "The Absence of GATA4 in the Distal Small Intestine Defines the Ileal Phenotype," Gastroenterology, ABA Abstract, Abstract 602, 2008b, 134:A83-A84, 2 pgs.

Bonilla-Claudio, M., et al., "Bmp signaling regulates a dose-dependent transcriptional program to control facial skeletal development," Development, 2012, 139:709-719, 11 pgs.

Bosse, T., et al., "Gata4 and Hnf1α are partially required for the expression of specific intestinal genes during development," Am J Physiol Gastrointest Liver Physiol, 2007, 292:G1302-G1314, 13 pgs.

Bouchi, R., et al., "FOXO1 Inhibition Yields Functional Insulin-Producing Cells In Human Gut Organoid Cultures," Nat Commun, 2014, 5:4242, 24 pgs.

Broda, T.R., et al., "Generation of human antral and fundic gastric organoids from pluripotent stem cells," Nature Protocols, Nov. 2018, 14(1):28-50, 23 pgs., XP036660403.

Burnicka-Turek, O., et al., "INSL5-Deficient Mice Display an Alteration in Glucose Homeostasis and an Impaired Fertility," Endocrinology, Oct. 2012, 153(10):4655-4665, 11 pgs.

Choi, E., et al., "Cell lineage distribution atlas of the human stomach reveals heterogeneous gland populations in the gastric antrum," Gut, 2014, 63(11):1711-1720, 20 pgs.

Choi, E., et al., "Expression of Activated Ras in Gastric Chief Cells of Mice Leads to the Full Spectrum of Metaplastic Lineage Transitions," Gastroenterology, Apr. 2016, 150(4):918-930, 23 pgs.

De Santa Barbara, P., et al., "Bone Morphogenetie Protein Signaling Pathway Plays Multiple Roles During Gastrointestinal Tract Development," Developmental Dynamics, 2005, 234:312-322, 11 pgs.

Dobreva, G., et al., "SATB2 Is a Multifunctional Determinant of Craniofacial Patterning and Osteoblast Differentiation," Cell, 2006, 125:971-986, 16 pgs.

Driver, I., et al., "Specification of regional intestinal stem cell identity during *Drosophila* metamorphosis," Development, 2014, 141:1848-1856, 9 pgs.

Duluc, I., et al., "Fetal Endoderm Primarily Holds the Temporal and Positional Information Required for Mammalian Intestinal Development," The Journal of Cell Biology, 1994, 126(1):211-221, 11 pgs.

Fagerberg, L., et al., "Analysis of the Human Tissue-specific Expression by Genome-wide Integration of Transcriptomics and Antibody-based Proteomies," Mol Cell Proteomics, 2014, 13:397-406, 10 pgs.

Finkbeiner, S.R., et al., "Transcriptome-wide Analysis Reveals Hallmarks of Human Intestine Development and Maturation In Vitro and In Vivo," Stem Cell Reports, 2015, 4:1140-1155, 16 pgs.

Fitzpatrick, D.R., et al., "Identification of SATB2 as the cleft palate gene on 2q32-q33," Human Molecular Genetics, 2003, 12(19):2491-2501, 11 pgs.

Genthe, J.R., et al., "Ventromorphins: A new class of small molecule activators of the canonical BMP signaling pathan," ACS Chem Biol, 2017, 12(9):2436-2447, 21 pgs.

Georgas, K.M., et al., "An illustrated anatomical ontology of the developing mouse lower urogenital tract," Development, 2015, 142:1893-1908, 16 pgs.

Ginestet, C., Book Review in the Journal of the Royal Statistical Society. Series A (Statistics in Society) (2011), of ggplot2: Elegant Graphics for Data Analysis, by H. Wickham, 2009; 174(1):245, 2 pgs.

Goldenring, J.R., et al., "Differentiation of the Gastric Mucosa: III. Animal models of oxyntic atrophy and metaplasia," Am J Physiol Gastrointestinal and Liver Physiol, 2006, 291:G999-G1004, 6 pgs.

Goldenring, J.R., et al., "Overexpression of Transforming Growth Factor-α Alters Differentiation of Gastric Cell Lineages," Dig. Dis. Sci, 1996, 41(4):773-784, 12 pgs.

Guo, Z., et al., "Injury-induced BMP signaling negatively regulates *Drosophila* midgut homeostasis," J Cell Biol, 2013, 201(6):945-961, 17 pgs.

Gyorgy, A.B., et al., "SATB2 interacts with chromatin-remodeling molecules in differentiating cortical neurons" European Journal of Neuroscience, 2008, 27:865-873, 9 pgs.

Haramis, A-P.G., et al., "De Novo Crypt Formation and Juvenile Polyposis on BMP Inhibition in Mouse Intestine," Science, 2004, 303:1684-1686, 4 pgs.

Hardwick, J.C.H., et al., "Bone Morphogenetic Protein 2 Is Expressed by, and Acts Upon, Mature Epithelial Cells in the Colon," Gastroenterology, 2004, 126:111-121, 11 pgs.

He, X.C., et al., "BMP signaling inhibits intestinal stem cell self-renewal through suppression of Wnt-β-catenin signaling," Nature Genetics, 2004, 36(10):1117-1121, 5 pgs.

(56) References Cited

OTHER PUBLICATIONS

Higuchi, Y., et al., "Gastrointestinal Fibroblasts Have Specialized, Diverse Transcriptional Phenotypes: A Comprehensive Gene Expression Analysis of Human Fibroblasts," PloS One, Jun. 2015, 10(6):e0129241, 19 pgs.
Hoffmann, W., "Current Status on Stem Cells and Cancers of the Gastric Epithelium," Int. J. Mol. Sci, 2015, 16:19153-19169, 17 pgs.
Holland, P.W.H., et al., "Classification and nomenclature of all human homeobox genes," BMC Biology, 2007, 5:47, 29 pgs.
Huh, W.J., et al., "Ménétrier's Disease: Its Mimickers and Pathogenesis," Journal of Pathology and Translational Medicine, 2016; 50:10-16, 7 pgs.
Jeejeebhoy, K.N., "Shortbowel syndrome: a nutritional and medical approach," CMAJ, 2002, 166(10):1297-1302, 6 pgs.
Johnston, T.B., et al., "Extroversion of the Bladder, Complicated by the Presence of Intestinal Openings on the Surface of the Extroverted Area," J Anat Physiol, 1913, 48(Pt 1):89-106. 18 pgs.
Keeley, T.M., et al., "Cytodifferentiation of the postnatal mouse stomach in normal and Huntingtin-interacting protein 1-related-deficient mice," Am. J. Physiol. Gastrointest. Liver Physiol., 2010, 299:G1241-G1251, 11 pgs.
Kim, B-M., et al., "Regulation of mouse stomach development and Barx1 expression by specific microRNAs," Development, 2011, 138:1081-1086, 6 pgs.
Kim, B-M., et al., "The Stomach Mesenchymal Transcription Factor Barx1 Specifies Gastric Epithelial Identity through Inhibition of Transient Wnt Signaling," Developmental Cell, 2005, 8:611-622, 12 pgs.
Kohlnhofer, B.M., et al., "GATA4 Regulates Epithelial Cell Proliferation to Control Intestinal Growth and Development in Mice," Cellular and Molecular Gastroenterology and Hepatology, 2016, 2(2):2189-209, 21 pgs.
Kraus, M.R.C., et al., "Patterning and shaping the endoderm in vivo and in culture," Current Opinion Genetics & Development., 2012, 22:347-353, 7 pgs.
Lambrecht, N.W.G., et al., "Identification of the K efflux channel coupled to the gastric H-K-ATPase during acid secretion," Physiological Genomics, 2005, 21:81-91, 11 pgs.
Lameris, A.L., et al., "Expression profiling of claudins in the human gastrointestinal tract in health and during inflammatory bowel disease," Scandinavian Journal of Gastroenterology, 2013, 48:58-69, 12 pgs.
Langmead, G., et al., "Ultrafast and memory-efficient alignment of short DNA sequences to the human genome," Genome Biology, 2009, 10:R25, 10 pgs.
Lennerz, J.K.M., et al., "The Transcription Factor MIST1 Is a Novel Human Gastric Chief Cell Marker Whose Expression Is Lost in Metaplasia, Dysplasia, and Carcinoma," The American Journal of Pathology, 2010, 177(3):1514-1533, 20 pgs.
Li, H., et al., "TreeFam: a curated database of phylogenetic trees of animal gene families," Nucleic Acids Research, 2006, 34:D572-D580, 9 pgs.
Li, L., "BMP Signaling Inhibits Intestinal Stem Cell Self-Renewal Through Antagonizing Wnt Signaling," Gastroenterology, AASLD Abstracts, Abstract S1223, 2005, 128:A702, 1 pg.
McGovern, D.P.B., et al., "Genome-wide association identifies multiple ulcerative colitis susceptibility loci," Nature Genetics, 2010, 42(4):332-337, 8 pgs.
Molodecky, N.A., et al., "Increasing Incidence and Prevalence of the Inflammatory Bowel Diseases With Time, Based on Systematic Review," Gastroenterology, 2012, 142:46-54, 51 pgs.
Moser, A.R., et al., "A dominant mutation that predisposes to multiple intestinal neonlasia in the mouse," Science, 1990, 247(4940):322-324, 3 pgs.
Nielsen, C., et al., "Gizzard Formation and the Role of Bapx1," Developmental Biology, 2001, 231:164-174, 11 pgs.
Nomura, S., et al., "Evidence for Repatteming of the Gastric Fundic Epithelium Associated With Ménétrier's Disease and TGFα Overexpression," Gastroenterology, 2005, 128:1292-1305, 14 pgs.

Park, Y.H., et al., "Review of Atrophie Gastritis and Intestinal Metaplasia as a Premalignant Lesion of Gastric Cancer," Journal of Cancer Prevention, 2015, 20(1):25-40, 16 pgs.
Patankar, J.V., et al., "Intestinal Deficiency of Gata4 Protects from Diet-Induced Hepatic Steatosis by Suppressing De Novo Lipogenesis and Gluconeogenesis in Mice," Journal of Hepatology, Posters, Abstract 1253, 2012, 56:S496, 1 pg.
Patankar, J.V., et al., "Intestinal GATA4 deficiency protects from diet-induced hepatic steatosis," Journal of Hepatology, 2012, 57:1061-1068, 8 pgs.
Ramalingam, S., et al., "Distinct levels of Sox9 expression mark colon epithelial stem cells that form colonoids in culture," Am J Physiol Gastrointest Liver Physiol,, 2012, 302:G10-G20, 11 pgs.
Ramsey, V.G., et al., "The maturation of mucus-secreting gastric epithelial progenitors into digestive-enzyme secreting zymogenie cells requires Mist1," Development, 2007, 134:211-222, 12 pgs.
Rankin, S.A., et al., "A Molecular Atlas of Xenopus Respiratory System Development," Developmental Dvnamies, 2015, 244:69-85, 17 pgs.
Rankin, S.A., et al., "Suppression of Bmp4 signaling by the zinc-finger repressors Osr1 and Osr2 is required for Wnt/β-catenin-mediated lung specification in Xenopus," Development, 2012, 139:3010-3020, 11 pgs.
Ratineau, C., et al., "Endoderm- and mesenchyme-dependent commitment of the differentiated epithelial cell types in the developing intestine of rat," Differentiation, 2003, 71:163-169, 7 pgs.
Roberts, D.J., et al., "Sonic hedgehog is an endodermal signal inducing Bmp-4 and Hox genes during induction and regionalization of the chick hindgut," Development, 1995, 121:3163-3174, 12 pgs.
Rodríguez-Piñeiro, A.M., et al., "Studies of mucus in mouse stomach, small intestine, and colon. II. Gastrointestinal mucus proteome reveals Muc2 and Muc5ac accompanied by a set of core proteins," Am J Physiol Gastrointest Liver Physiol, 2013, 305:G348-G356, 9 pgs.
Rodriquez, P., et al., "BMP signaling in the development of the mouse esophagus and forestomach," Development, 2010, 137:4171-4176, 6 pgs.
Roth, R.B., et al., "Gene expression analyses reveal molecular relationships among 20 regions of the human CNS," Neurogenetics, 2006, 7:67-80, 14 pgs.
Savidge, T.C., et al., "Human intestinal development in a severe-combined immunodeficient xenograft model," Differentiation, 1995, 58:361-371, 11 pgs.
Savin, T., et al., "On The Growth and form of the gut," Nature, 2011, 476:57-62, 7 pgs.
Schumacher, M.A., et al., "The use of murine-derived fundic organoids in studies of gastric physiology," J. Physiol., 2015, 593(8): 1809-1827, 19 pgs.
Sheehan-Rooney, K., et al., "Bmp and Shh Signaling Mediate the Expression of satb2 in the Pharyngeal Arches," PLoS One, Mar. 2013, 8(3):e59533, 10 pgs.
Sherwood, R.I., et al., "Transcriptional dynamics of endodermal organ formation," Dev Dyn, 2009, 238(1):29-42, 23 pgs.
Sherwood, R.I., et al., "Wnt signaling specifies and patterns intestinal endoderm," Mechanisms of Development, 2011, 128:387-400, 14 pgs.
Shyer, A.E., et al., "Bending Gradients: How the Intestinal Stem Cell Gets Its Home," Cell, 2015, 161:569-580, 13 pgs.
Siegel, R., et al., "Colorectal Cancer Statistics, 2014," CA Cancer J Clin, 2014, 64:104-117, 14 pgs.
Sigalet, D.L., "The Role of the Enteric Neuronal System In Controlling Intestinal Function," Clinical Surgery Society Magazine, 2003, 64:214. (Reference unavailable).
Speer, A.L., et al., "Fibroblast Growth Factor 10-Fibroblast Growth Factor Receptor 2b Mediated Signaling Is Not Required for Adult Glandular Stomach Homeostasis," PLoS ONE, 2012, 7(11):e49127, 12 pgs.
Stange, D.E., et al., "Differentiated Troy+ chief cells act as 'reserve' stem cells to generate all lineages of the stomach epithelium," Cell, 2013, 155(2):357-368, 26 pgs.

(56) References Cited

OTHER PUBLICATIONS

Thanasupawat, T., et al., "INSL5 is a novel marker for human enteroendocrine cells of the large intestine and neuroendocrine tumours," Oncology Reports, 2013, 29:149-154, 6 pgs.
Trapnell, C., et al., "Differential gene and transcript expression analysis of RNA-seq experiments with TopHat and Cufflinks," Nat Protoc, 2013, 7(3):562-578, 39 pgs.
Uppal, K., et al., "Meckel's Diverticulum: A Review," Clinical Anatomy, 2011, 24: 416-422, 7 pgs.
Van Dop, W.A., et al., "Depletion of the Colonic Epithelial Precursor Cell Compartment Upon Conditional Activation of the Hedgehog Pathway," Gastroenterology, 2009, 136:2195-2203, 16 pgs.
Van Klinken, B.J-W., et al., "MUC5B is the prominent mucin in human gallbladder and is also expressed in a subset of colonic goblet cells," The American Journal of Physiology, 1998, 274:G871-G878, 8 pgs.
Walker, E.M., et al., "GATA4 and GATA6 regulate intestinal epithelial cytodifferentiation during development," Developmental Biology, 2014, 392:283-294, 12 pgs.
Walton, K.D., et al., "Epithelial Hedgehog signals direct mesenchymal villus patterning through BMP," Abstracts / Developmental Biology, Program/Abstract # 354, 2009, 331:489, 1 pg.
Walton, K.D., et al., "Hedgehog-responsive mesenchymal clusters direct patterning and emergence of intestinal villi," PNAS, 2012, 109(39):15817-15822, 6 pgs.
Walton, K.D., et al., "Villification in the mouse: Bmp signals control intestinal villus patterning," Development, 2016, 143:427-436, 10 pgs.
Wang, X., et al., "Cloning and variation of ground state intestinal stem cells," Nature, 2015, 522:173-178, 18 pgs.
Wehkamp, J., et al., "Paneth cell antimicrobial peptides: Topographical distribution and quantification in human gastrointestinal tissues," FEBS Letters, 2006, 580:5344-5350, 7 pgs.
Weis, V.G., et al., "Current understanding of SPEM and its standing in the preneoplastic process," Gastric Cancer, 2009, 12:189-197, 9 pgs.
Whissell, G., et al., "The transcription factor GATA6 enables self-renewal of colon adenoma stem cells by repressing BMP gene expression," Nature Cell Biology, 2014, 16(7):695-707, 24 pgs.
Wills, A., et al., "Bmp signaling is necessary and sufficient for ventrolateral endoderm specification in Xenopus," Dev Dyn., 2008, 237(8):2177-2186, 18 pgs.
Xue, X., et al., "Endothelial PAS Domain Protein 1 Activates the Inflammatory Response in the Intestinal Epithelium to Promote Colitis in Mice," Gastroenterology, 2013, 145:831-841, 11 pgs.
Yahagi, N., et al., "Position-specific expression of Hox genes along the gastrointestinal tract," Congenital Anomalies, 2004, 44: 18-26, 9 pgs.
Zbuk, K.M., et al., "Hamartomatous polyposis syndromes," Gastroenterology & Hepatology, 2007, 4(9):492-502, 12 pgs.
European Search Report and Written Opinion dated Oct. 31, 2019 for Application No. EP 177934510, 11 pgs.
Japanese Office Action, Notification of Reasons for Refusal, and First Search Report by Registered Search Organization, dated May 14, 2019 for Application JP 2017-520900, 65 pgs.
Japanese Office Action, Notice of Reasons for Refusal, and Search Report by Registered Search Organization, dated Apr. 2, 2019 for Application No. JP 2016-569618, 42 pgs.
Singaporean Office Action, Third Written Opinion, dated May 3, 2019 for Application No SG 11201609953X, 5 pgs.
An, W.F., et al., "Discovery of Potent and Highly Selective Inhibitors of GSK3b," Molecular Libraries, Probe Report, May 2014, 115 pgs.
Chang, H-M., et al., "BMP15 Suppresses Progesterone production by Down-Regulating StAR via ALK3 in Human Granulosa Cells," Molecular Endocrinology, 2013, 27:2093-2104, 12 pgs.
Deng, H., "Mechanisms of retinoic acid on the induction of differentiation of neural stem cells for newborn rat striatum," Chinese Doctoral and Master Dissertations Full-Text Database (Doctoral) Basic Science, Issue 4, Apr. 15, 2006, pp. 1-89. Reference unavailable.
Deng, H., et al., "Effects of all-trans retinoic acid on the differentiation of neural stem cells and the expression of c-myc gene," Chinese Journal of Tissue Engineering Research, Mar. 18, 2007, 11(11):2039-2042. Reference unavailable.
Krausova, M., et al., "Wnt signaling in adult intestinal stem cells and cancer," Cellular Signalling, 2014, 26:570-579, 10 pgs.
Lim, D.A., et al., "Noggin Antagonizes BMP Signaling to Create a Niche for Adult Neurogenesis," Neuron, Dec. 2000, 28:713-726 14 pgs.
McMahon, J.A., et al., "Noggin-mediated antagonism of BMP signaling is required for growth and patterning of the neural tube and somite," Genes & Development, May 1998 12:1438-1452, 15 pgs.
Ornitz, D.M., et al., "FGF signaling pathways in endochondral and intramembranous bone development and human genetic disease," Genes & Development, Jun. 2002, 16:1446-1465, 21 pgs.
Pan, Q., *Physiology*, University of Science and Technology of China Press, Jan. 31, 2014, pp. 149-150. Reference unavailable.
Que, J., et al., "Morphogenesis of the trachea and esophagus: current players and new roles for noggin and Bmps," Differentiation, 2006, 74:422-437, 16 pgs.
Raju, R., et al., "A Network Map of FGF-1/FGFR Signaling System," Journal of Signal Transduction, Apr. 2014, 2014:1-16, Article ID 962962, 16 pgs.
Su, N., et al., "Role of FGF/FGFR signaling in skeletal development and homeostasis: learning from mouse models," Bone Research, 2014, 2:14003, 24 pgs.
Wan, W., et al., "The Role of Wnt Signaling in the Development of Alzheimer's Disease: A Potential Therapeutic Target?", BioMed Research International, 2014, 2014:1-9, Article ID 301575, 9 pgs.
Yanagita, M., "Modulator of bone morphogenetic protein activity in the progression of kidney diseases," Kidney International, 2006, 70:989-993, 5 pgs.
Yu, Y., *Chinese Studies on Disease Signaling Pathway and Targeted Therapy*, Anhui Science and Technology Press, May 31, 2013, p. 363. Reference unavailable.
Chinese Office Action, and Preliminary Search Report, dated Jan. 30, 2019 for Application No. CN 201580034910.4, 11 pgs.
Israeli Office Action dated Nov. 29, 2018 for Application No. IL 249253, 8 pgs.
International Search Report and Written Opinion dated Sep. 28, 2018 for Application No. PCT/US2018/029083, 14 pgs.
Barlow, A.J., et al., "Critical numbers of neural crest cells are required in the pathways from the neural tube to the foregut to ensure complete enteric nervous system formation," Development, 2008, 135:1681-1691, 11 pgs.
Burns, A.J., et al., "In ovo transplantation of enteric nervous system precursors from vagal to sacral neural crest results in extensive hindgut colonisation," Development, 2002, 129:2785-2796, 12 pgs.
Kawaguchi, J., et al., "Isolation and propagation of enteric neural crest progenitor cells from mouse embryonic stem cells and embryos," Development, 2010, 137:693-704, 12 pgs.
Merker, S.R., et al., "Gastrointestinal organoids: How they gut it out," Developmental Biology, 2016, 420:239-250, 12 pgs.
Mosher, J.T., et al., "Intrinsic differences among spatially distinct neural crest stem cells in terms of migratory properties, fate-determination, and ability to colonize the enteric nervous svstem" Dev. Biol., Mar. 2007, 303(1):1-15, 29 pgs.
International Search Report dated Feb. 9, 2012 for Application No. PCT/US2011/035518, 7 pgs.
International Preliminary Report on Patentability and Written Opinion dated Nov. 6, 2012 for Application No. PCT/US2011/035518, 5 pgs.
International Search Report and Written Opinion dated Dec. 15, 2015 for Application No. PCT/US2015/032626, 18 pgs.
International Search Report and Written Opinion dated Jan. 25, 2016 for Application No. PCT/US2015/055956, 17 pgs.
Agopian, V.G., et al., "Intestinal Stem Cell Organoid Transplantation Generates Neomucosa in Dogs," Journal of Gastrointestinal Surgery, Jan. 23, 2009, 13(5):971-982, XP055241418, 12 pgs.

(56) References Cited

OTHER PUBLICATIONS

Alessi, D.R., et al., "LKB1-Dependent Signaling Pathways," Annu. Rev. Biochem., 2006, 75:137-63, 30 pgs.

Ameri, J., et al., "FGF2 Specifies hESC-Derived Definitive Endoderm into Foregut/Midgut Cell Lineages in a Concentration-Dependent Manner," Stem Cells, ePUB Nov. 3, 2009, 28(1):45-56, 12 pgs.

Andrews, P. et al., "Embryonic stem (ES) cells and embryonal carcinoma (EC) cells: opposite sides of the same coin," Biochem Soc Trans, 2005, 33:1526-1530, 5 pgs.

Ang., S.L. et al., "The formation and maintenance of the definitive endoderm lineage in the mouse: involvement of HNF3/forkhead proteins," Development, 1993, 119:1301-1315, 15 pgs.

Avansino, J.R., et al., "Orthotopic transplantation of intestinal mucosal organioids in rodents," Surgery, Sep. 2006, 140(3):423-434, XP005610494, 12 pgs.

Bansal, D. et al., "An ex-vivo Human Intestinal Model to Study *Entamoeba histolytica* Pathogenesis," PLoS Neglected Tropical Diseases, Nov. 2009, 3(11): e551, 11 pgs.

Barker, N., et al., "Lgr5+ve Stem Cells Drive Self-Renewal in the Stomach and Build Long-Lived Gastric Units In Vitro," Cell Stem Cell, Jan. 1, 2012, 6(1):25-36, XP055210573, 12 pgs.

Bastide, P., et al. "Sox9 regulates cell proliferation and is required for Paneth cell differentiation in the intestinal epithelium," JCB, 2007, 178(4), pp. 635-648, 14 pgs.

Beck, F., et al., "Expression of Cdx-2 in the Mouse Embryo and Placenta: Possible Role in Patterning of the Extra-Embryonic Membranes," Dev Dyn, 1995, 204:219-227, 9 pgs.

Brevini, T.A.L., et al., "No shortcuts to pig embryonic stem cells," Theriogenology, 2010, 74:544-550, 7 pgs.

Chen, C., et al., "Pdx1 inactivation restricted to the intestinal epithelium in mice alters duodenal gene expression in enterocytes and enteroendocrine cells," Am. J. Physiol. Gastrointest. Liver Pyshiol., 2009, 297:G1126-G1137, 12 pgs.

Coghlan, M. et al., "Selective small molecule inhibitors of glycogen synthase kinase-3 modulate glycogen metabolism and gene transcription," Chem Biol, 2000, 7(10):793-803, 11 pgs.

Couzin, J., "Small RNAs make big splash," Science, 2002, 298:2296-2297, 2 pgs.

D'Amour, K.A. et al., "Efficient differentiation of human embryonic stem cells to definitive endoderm," Nature Biotechnology, Dec. 2005, 23(12):1534-1541, 8 pgs.

D'Amour, K.A. et al., "Production of pancreatic hormone-expressing endocrine cells from human embryonic stem cells," Nat Biotechnol, 2006, 24:1392-1401, 10 pgs.

De Santa Barbara, P. et al., "Development and differentiation of the intestinal epithelium," Cell Mol Life Sci, 2003, 60(7): 1322-1332, 38 pgs.

Dessimoz, J. et al., "FGF signaling is necessary for establishing gut tube domains along the anterior-posterior axis in vivo," Mech Dev, 2006, 123:42-55, 14 pgs.

Elbashir, S.M. et al., "Functional anatomy of siRNAs for mediating efficient RNAi in *Drosophila melanogaster* embryo lysate," EMBO J., 2001, 20:6877-6888, 12 pgs.

Evans, M.J. et al., "Establishment in culture of pluripotent cells from mouse embryos," Nature, 1981, 292(5819):154-156, 3 pgs.

Gracz, A.D. et al. "Sox9 Expression Marks a Subset of CD24-expressing Small Intestine Epithelial Stem Cells that Form Organoids in vitro," Am J Physiol Gastrointest Liver Physiol, 2010, 298:G590-600, 11 pgs.

Gregorieff, A., et al., "Wnt signaling in the intestinal epithelium: from endoderm to cancer," Genes & Dev., 2005, 19:877-890, 14 pgs.

Hannon, G.J., "RNA interference," Nature, 2002, 418:244-251, 8 pgs.

Haveri, H., et al., "Transcription factors GATA-4 and GATA-6 in normal and neoplastic human gastrointestinal mucosa," BMC Gastroenterology, 2008, 8:9, 13 pgs.

Hutvágner, G. et al., "A microRNA in a Multiple-Turnover RNAi Enzyme Complex," Science 2002, 297:2056-2060, 5 pgs.

Jenny, M., et al., "Neurogenin3 is differentially required for endocrine cell fate specification in the intestinal and gastric epithelium," EMBO J, 2002, 21:6338-6347, 10 pgs.

Johannesson, M., et al., "FGF4 and Retinoic Acid Direct Differentiation of hESCs into PDX1-Expressing Foregut Endoderm in a Time- and Concentration-Dependent Manlier," PLoS One, Mar. 2009, 4(3):1-13, 13 pgs.

Kaji, K. et al., 2009, "Virus free induction of pluripotency and subsequent excision of reprogranimming factors," Nature, 2009, 458:771-775, 12 pgs.

Klimanskaya, I. et al., "Human embryonic stem cells derived without feeder cells," Lancet, 2005, 365(9471):1636-1641, 6 pgs.

Koo, B-K., et al., "Controlled gene expression in primary Lgr5 organoid cultures," Nature Methods, Jan. 1, 2012, 9(1):83-83, XP055225429, 4 pgs.

Kroon, E., et al., "Pancreatic endoderm derived from human embryonic stem cells generates glucose-responsive insulin-secreting cells in vivo," Nat Biotechnol, 2008, 26(4):443-52, 10 pgs.

Kubo, A. et al., "Development of definitive endoderm from embryonic stem cells in culture," Development, 2004, 131(7):1651-1662, 12 pgs.

Lambert, P.F. et al., "Using an Immortalized Cell Line to Study the HPV Life Cycle in Organotypic 'Raft' Cultures," Methods in Molecular Medicine, 2005, 119:141-155, 15 pgs.

Lavial, F., et al., "Chicken embryonic stem cells as a non-mammalian embryonic stem cell model," Develop. Growth Diff., 2010, 52:101-114, 14 pgs.

Lee, C.S. et al., "Neurogenin 3 is essential for the proper specification of gastric enteroendocrine cells and the maintenance of gastric epithelial cell identity," Genes Dev, 2002, 16:1488-1497, 10 pgs.

Lindley, R.M., et al., "Human and Mouse Enteric Nervous System Neurosphere Transplants Regulate the Function of Aganglionic Embryonic Distal Colon," Gastroenterology, Jul. 2008, 135(1):205-216, XP022823118, 18 pgs.

Liu, J., et al., "A Small-Molecule Agonist of the Wnt Signaling Pathway," Angew Chem Int Ed Engl., 2005, 44(13):1987-1990, 4 pgs.

Logan, C.Y., et al., "The Wnt Signaling Pathway in Development and Disease," Annual Review of Cell and Developmental Biology, 2004, 20:781-810, 30 pgs.

López-Díaz, L. et al., "Intestinal Neurogenin 3 directs differentiation of a bipotential secretory progenitor to endocrine cell rather than goblet cell fate," Dev Biol, 2007, 309:298-305, 8 pgs.

Ludwig, T.E., et al, "Derivation of human embryonic stem cells in defined conditions," Nat Biotechnol, 2006, 24:185-187, 3 pgs.

Ludwig, T.E., et al., "Feeder-independent culture of human embryonic stem cells," Nat Methods, 2006, 3:637-646, 10 pgs.

Mahe, M.M., et al., "Establishment of Gastrointestinal Epithelial Organoids," Current Protocols in Mouse Biology 2013, 2013, 3(4):217-240, XP002750112, 24 pgs.

Martin, G.R., "Teratocarcinomas and Mammalian Embryogenesis," Science, 1980, 209(4458):768-776, 9 pgs.

McCracken, K.W., et al., "Generating human intestinal tissue from pluripotent stem cells in vitro," Nature Protocols, Nov. 10, 2011, 6(12):1920-1928, XP055210541, 9 pgs.

McCracken, K.W., et al., "Modelling human development and disease in pluripotent stem-cell-derived gastric organoids," Nature, Oct. 29, 2014, 516(7531):400-404, XP055210509, 19 pgs.

McLin, V.A. et al., "Repression of Wnt/β-catenin signaling in the anterior endoderm is essential for liver and pancreas development," Development, 2007, 134:2207-2217, 11 pgs.

McLin, V.A. et al., "The Role of the Visceral Mesoderm in the Development of the Gastrointestinal Tract," Gastroenterology, 2009, 136:2074-2091, 18 pgs.

McManus, T., et al., "Gene Silencing in Mammals by Small Interfering RNAs," Nat. Rev. Genet, 2002, 3:737-747, 12 pgs.

Miyabayashi, T. et al., "Wnt/β-catenin/CBP signaling maintains long-term murine embryonic stem cell pluripotency," Proc Natl Acad Sci USA, 2007, 104(13):5668-5673, 6 pgs.

Muñoz, M., et al., "Conventional pluripotency markers are unspecific for bovine embryonic-derived-cell-lines," Theriogenology, 2008, 69:1159-1164, 6 pgs.

(56) References Cited

OTHER PUBLICATIONS

Neiiendam, J .L., et al., "An NCAM-derived FGF-receptor agonist, the FGL-peptide, induces neurite outgrowth and neuronal survival in primary rat neurons," J Neurochem, 2004, 91(4):920-935, 16 pgs.
Noguchi, T-A.K., et al., "Generation of stomach tissue from mouse embryonic stem cells," Nature Cell Biology, Jul. 20, 2015, 17(8):984-993, XP055225165, 19 pgs.
Okita, K., et al., "Generation of Mouse Induced Pluripotent Stem Cells Without Viral Vectors," Science, 2008, 322(5903):949-953, 5 pgs.
Ootani, A. et al., "Sustained in vitro intestinal epithelial culture within a Wnt-dependent stem cell niche," Nat Med, 2009, 15:701-706, 14 pgs.
Paddison, P. et al., "RNA interference: the new somatic cell genetics?" Cancer Cell, 2002, 2:17-23, 7 pgs.
Pai, R., et al "Deoxycholic acid activates β-catenin signaling pathway and increases colon cell cancer omwth and invasiveness," Mol Biol Cell, 2004, 15(5):2156-2163, 8 pgs.
Paris, D.B.B.P., et al., "Equine embryos and embryonic stem cells: Defining reliable markers of pluripotency" Theriogenology, 2010, 74:516-524, 9 pgs.
Petitte, J.N., et al., "Avian pluripotent stem cells," Mech. of Develop., 2004, 121:1159-1168, 10 pgs.
Richards, M., et al., "The Transcriptome Profile of Human Embryonic Stem Cells as Defined by SAGE," Stem Cells, 2004, 22:51-64, 14 pgs.
Rohrschneider, M.R., et al., "Polarity and cell fate specification in the control of C. elegans gatsru;ation," Dev. Dyn., 2009, 238(4):789-796, 15 pgs.
Sancho, E., et al., "Signaling Pathways in Intestinal Development and Cancer," Annual Review of Cell and Developmental Biology, 2004, 20:695-723, 29 pgs.
Sato, T., et al., "Single Lgr5 stem cells build crypt-villus structures in vitro without a mesenchymal niche," Nature, 2009, 459:262-265, 5 pgs.
Shan, J., et al., "Identification of a Specific Inhibitor of the Dishevelled PDZ Domain," Biochemistry, 2005, 44(47):15495-15503, 9 pgs.
Simon-Assmann, P., et al., "In vitro models of intestinal epithelial cell differentiation," Cell Biol. Toxicol., 2007, 23:241-256, 16 pgs.
Speer, A.L., et al., "Murine Tissue-Engineered Stomach Demonstrates Epithelial Differentiation," Journal of Surgical Research, Mar. 22, 2011, 171(1):6-14, XP028317226, 9 pgs.
Spence, J.R., et al., "Directed differentiation of human pluripotent stem cells into intestinal tissue in vitro," Nature, Feb. 2011, 470:105-109, 6 pgs.
Spence, J.R., et al., "Translational Embryology: Using Embryonic Principles to Generate Pancreatic Endocrine Cells From Embryonic Stem Cells," Developmental Dynamic, 2007, 236:3218-3227, 10 pgs.
Stadtfeld, M., et al., "Induced Pluripotent Stem Cells Generated without Viral Integration," Science, 2008, 322(5903):945-949, 5 pgs.
Taipale, J., et al., "The Hedgehog and Wnt signalling pathways in cancer," Nature, 2001, 411:349-354, 6 pgs.
Takahashi, K. et al., "Induction of Pluripotent Stem Cells from Adult Human Fibroblasts by Defined Factors," Cell, 2007, 131:861-872, 12 pgs.
Takahashi, K., et al., "Induction of Pluripotent Stem Cells from Mouse Embryonic and Adult Fibroblast Cultures by Defined Factors," Cell, 2006, 126:663-676, 14 pgs.
Takaki, M., et al., "In Vitro Formation of Enteric Neural Network Structure in a Gut-Like Organ Differentiated from Mouse Embryonic Stem Cells," Stem Cells, Jun. 9, 2006, 24(6):1414-1422, XP55241404, 9 pgs.
Thomson, J.A. et al., "Embryonic Stem Cell Lines Derived from Human Blastocysts," Science, 1998, 282(5391):1145-1147, 3 pgs.
Tuschl, T. et al., "Targeted mRNA degradation by double-stranded RNA in vitro," Genes Dev., 1999, 13:3191-3197, 7 pgs.
Van Breemen, R.B., et al., "Caco-2 cell permeability assays to measure drug bsorption," Expert Opin. Drug Metab. Toxicol, Aug. 2005, 1(2):175-185, 11 pgs.
Wang, J., et al., "Mutant Neurogenin-3 in Congenital Malabsorptive Diarrhea," New England Journal of Medicine, 2006, 355:270-280, 11 pgs.
Watson, C.L., et al., "An in vivo model of human small intestine using pluripotent stem cells," Nature Medicine, Oct. 19, 2014, 20(11):1310-1314, XP055241417, 7 pgs.
Wells, J.M., et al., "Early mouse endoderm is patterned by soluble factors from adjacent germ layers," Development, 2000, 127:1563-1572, 10 pgs.
Wells, J.M., et al., "How to Make an intestine," Development, Feb. 15, 2014, 141(4):752-760, XP055241409, 9 pgs.
Woltjen, K. et al., "piggyBac transposition reprograms fibroblasts to induced pluripotent stem cells," Nature, 2009, 458:766-770, 5 pgs.
Yamada, S., et al. "Differentiation of immature enterocytes into enteroendocrine cells by Pdx1 overexpression," Am. J. Physiol. Gastrointest. Liver Pyshiol., 2001, 281:G229-G236, 8 pgs.
Zhang, Q. et al., "Small-molecule synergist of the Wnt/β-catenin signaling pathway," Proc Natl Acad Sci USA, 2007, 104(18):7444-7448, 6 pgs.
Zhou, H. et al., "Generation of Induced Pluripotent Stem Cells Using Recombinant Proteins," Cell Stem Cell, 2009, 4(5):381-384, 4 pgs.
Zhou, Q., et al., "In vivo reprogramming of adult pancreatic exocrine cells to β-cells," Nature, 2008, 455: 627-632, 6 pgs.
Zorn, A.M. et al., "Vertebrate Endoderm Development and Organ Formation," Annu Rev Cell Dev Biol, 2009, 25:221-251, 36 pgs.
Keung, A.J., et al., "Presentation Counts: Microenvironmental Regulation of Stem Cells by Biophysical and Material Cues," Annu. Rev. Cell Dev. Biol., 2010, 26:533-556, 26 pgs.

\* cited by examiner

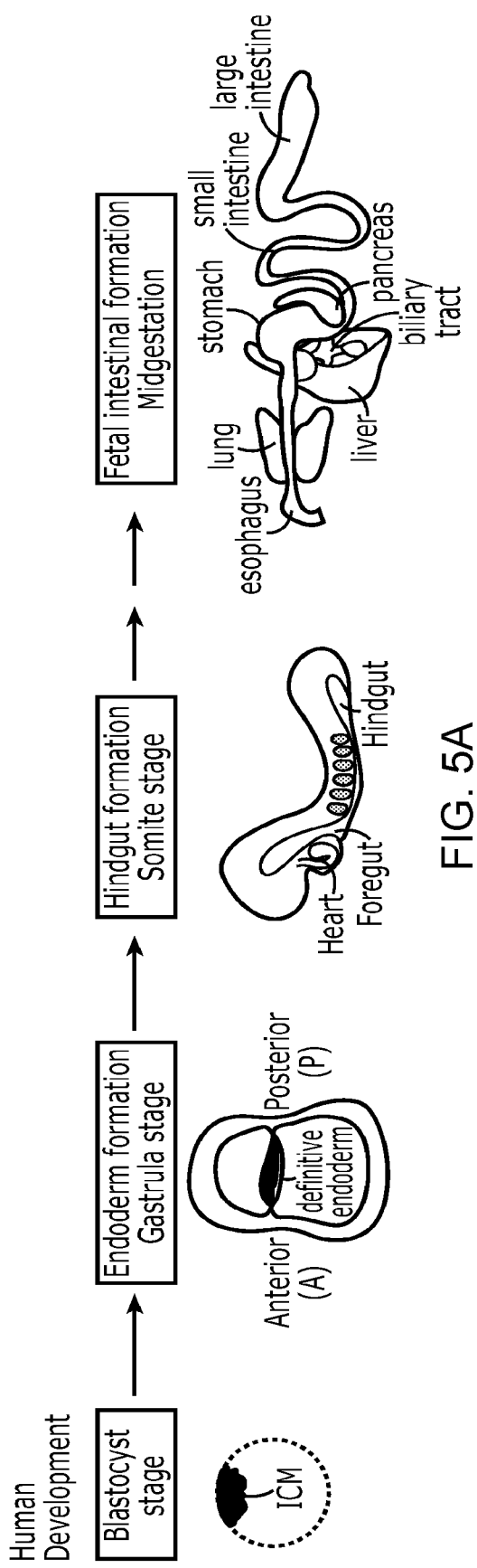
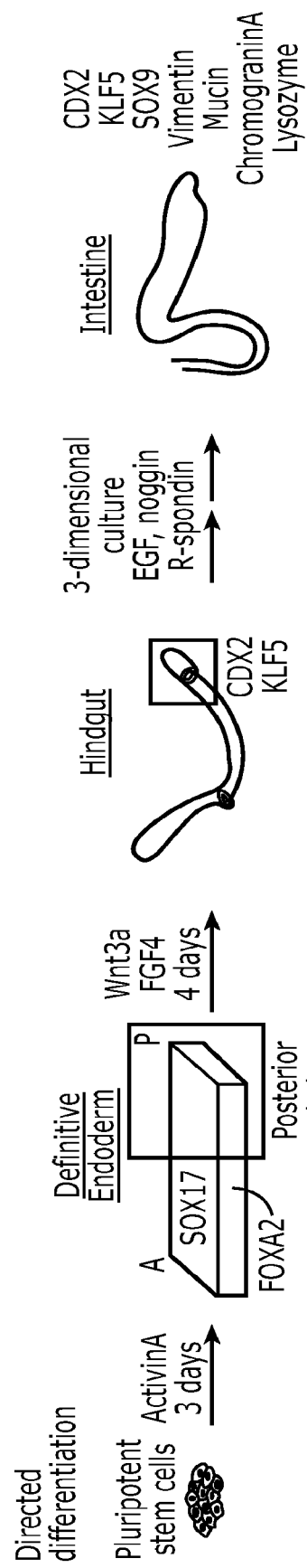
FIG. 5A
FIG. 5B

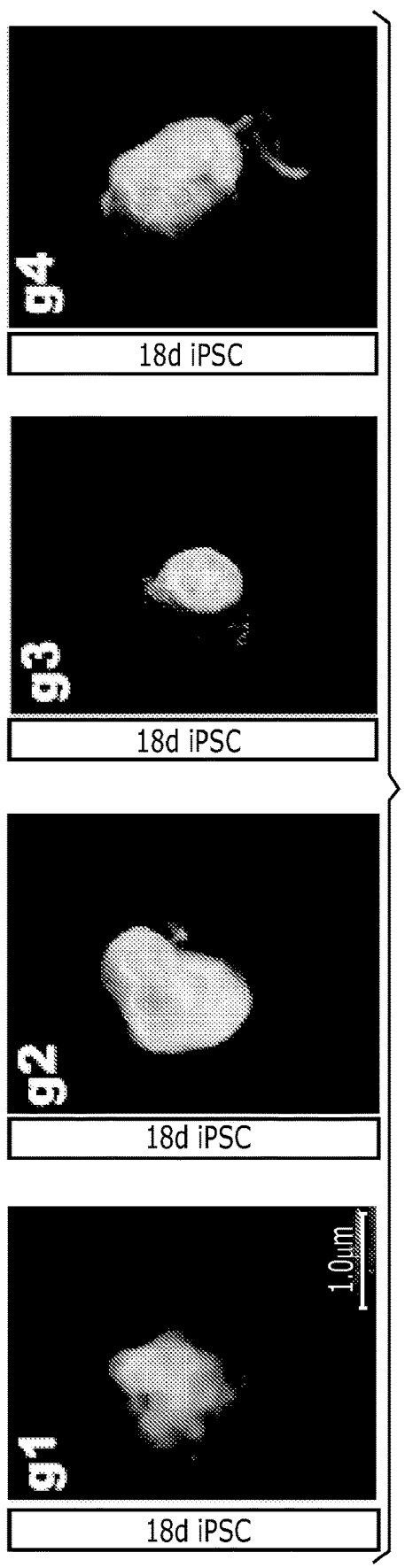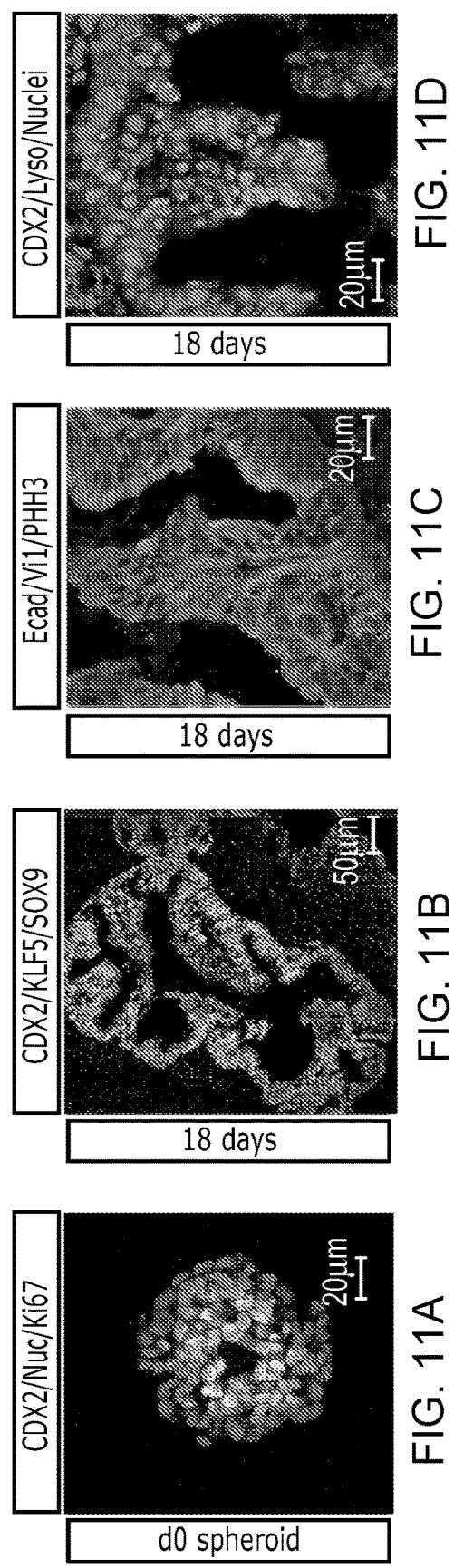

FIG. 11E VIL/MUC2/Ecad 28 days

FIG. 11F CDX2/KLF5/SOX9 28 days

FIG. 11I Villin

FIG. 11H Sox9

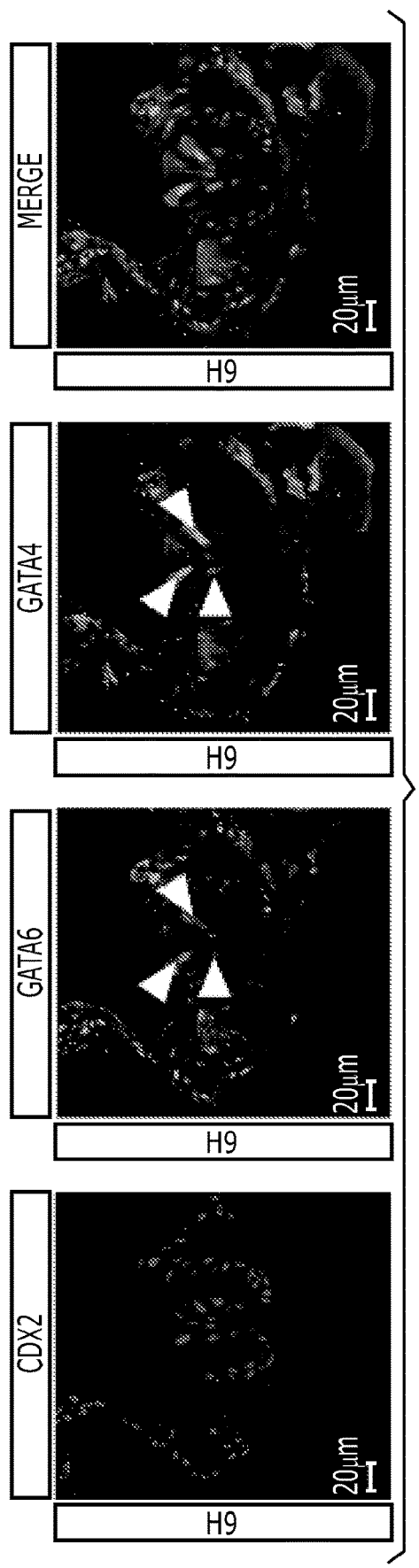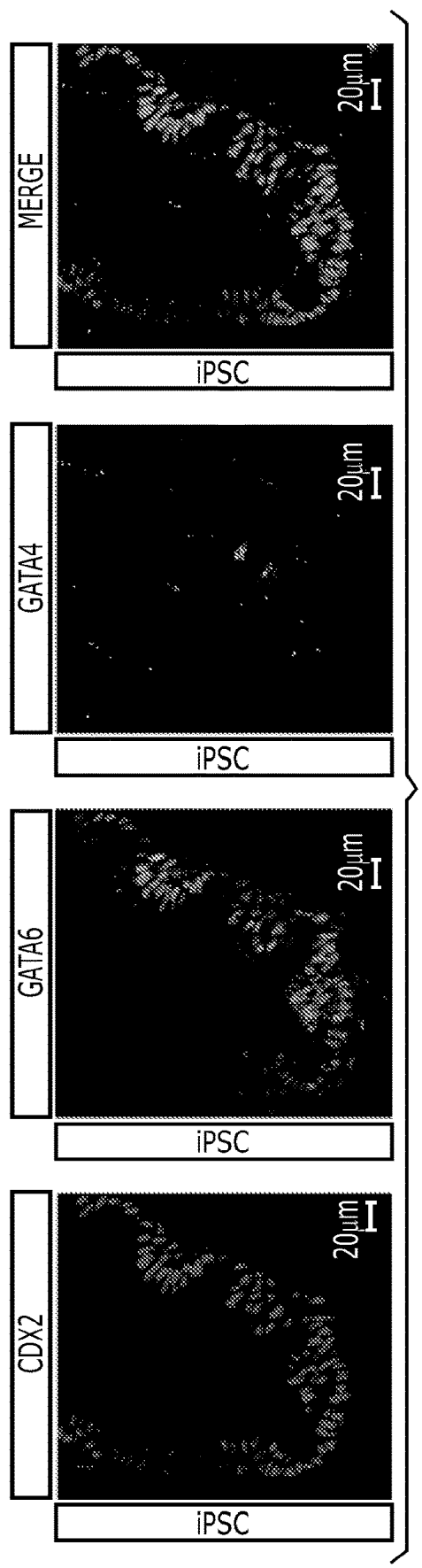
FIG. 12A
FIG. 12B

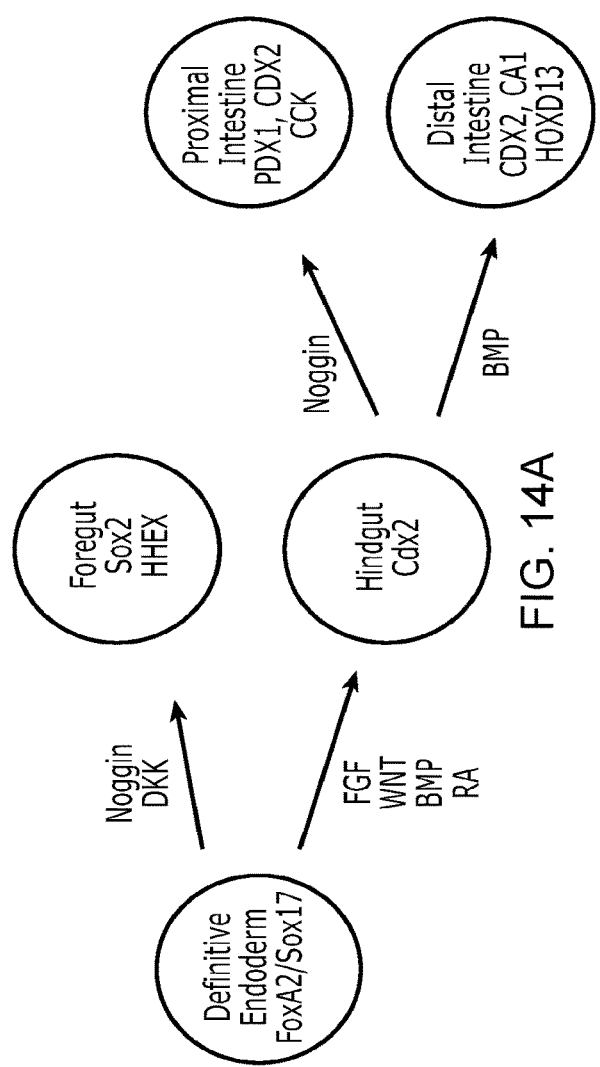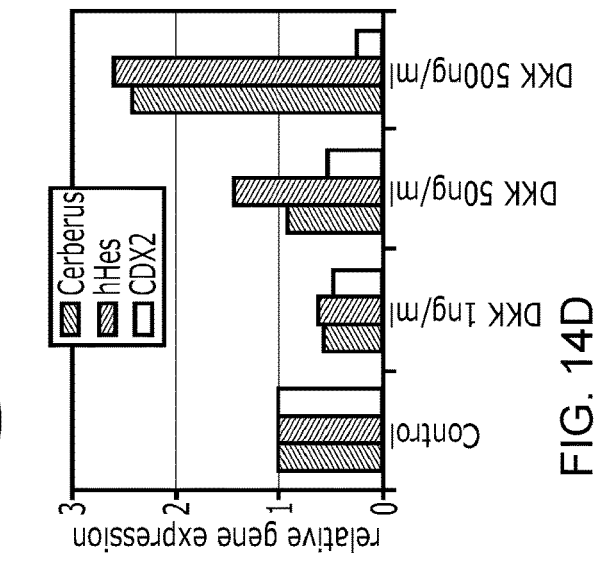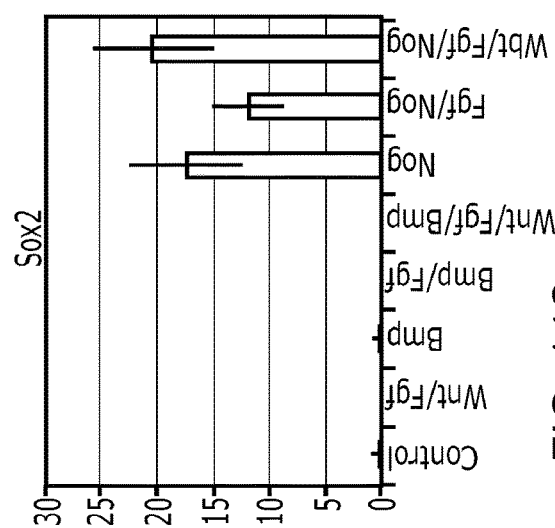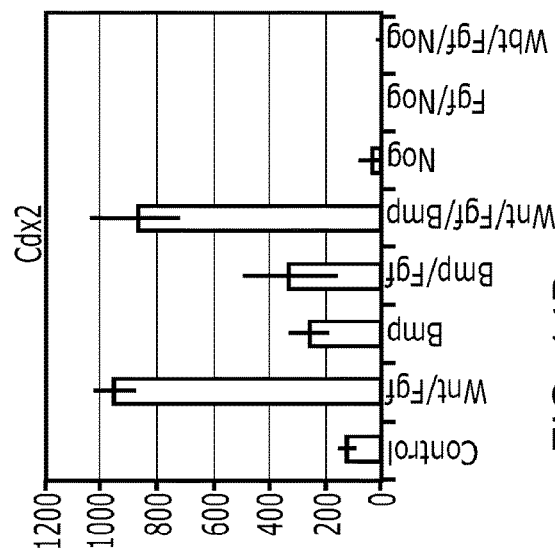
FIG. 14A
FIG. 14B
FIG. 14C
FIG. 14D

CDX2/CCK
Day 138
Organoids

Nog/EGF/Rsp1

CDX2/CCK
Day 138
Organoids

Nog/EGF/Rsp1

METHODS AND SYSTEMS FOR CONVERTING PRECURSOR CELLS INTO INTESTINAL TISSUES THROUGH DIRECTED DIFFERENTIATION

CROSS-REFERENCE TO RELATED APPLICATIONS

This application is a continuation of U.S. patent application Ser. No. 13/695,887, filed Nov. 2, 2012, which is a U.S. National Stage Entry of PCT/US11/35518, filed May 6, 2011, which is based on and claims priority from U.S. Provisional Patent Application Ser. No. 61/332,178, filed May 6, 2010, the contents of which are incorporated by reference in their entirety for all purposes.

STATEMENT REGARDING FEDERALLY-SPONSORED RESEARCH

This invention was made with government support under GM072915, DK080823, DK084167, CA142826, DK083202, and HD007463 awarded by the National Institutes of Health. The government has certain rights in the invention.

FIELD OF THE INVENTION

The invention disclosed herein generally relates to methods and systems for converting stem cells into specific tissue(s) or organ(s) through directed differentiation. In particular, the invention disclosed herein relates to methods and systems for promoting definitive endoderm formation from pluripotent stem cells. The invention disclosed herein further relates to methods and systems for promoting intestinal organoids or tissue formations from differentiated definitive endoderm.

BACKGROUND

Stem cells are found in all multi cellular organisms. They are characterized by the ability to renew themselves through mitotic cell division and differentiate into a diverse range of specialized cell types. The two broad types of mammalian stem cells are: embryonic stem cells that are isolated from the inner cell mass of blastocysts, and adult stem cells that are found in adult tissues. In a developing embryo, stem cells can differentiate into all of the specialized embryonic tissues. In adult organisms, stem cells and progenitor cells act as a repair system for the body, replenishing specialized cells, but also maintain the normal turnover of regenerative organs, such as blood, skin, or intestinal tissues.

Stem cells can now be grown and transformed into specialized cells with characteristics consistent with cells of various tissues such as muscles or nerves through cell culture. Highly plastic adult stem cells from a variety of sources, including umbilical cord blood and bone marrow, are routinely used in medical therapies. Embryonic cell lines and autologous embryonic stem cells generated through therapeutic cloning have also been proposed as promising candidates for future therapies.

The classical definition of a stem cell is typically indicative of two properties: self-renewal, the ability to go through numerous cycles of cell division while maintaining the undifferentiated state, and potency, the capacity to differentiate into specialized cell types. In some embodiments, stem cells are either totipotent or pluripotent, i.e. they are able to give rise to any mature cell type, although multipotent or unipotent progenitor cells are sometimes referred to as stem cells.

Potency specifies the differentiation potential (the potential to differentiate into different cell types) of the stem cell:

Totipotent stem cells (also known as omnipotent stem cells) can differentiate into embryonic and extraembryonic cell types. These cells can construct a complete, viable, organism. The cells are produced from the fusion of an egg and sperm cell. Cells produced by the first few divisions of the fertilized egg are also totipotent.

Pluripotent stem cells (PSCs) are the descendants of totipotent cells and can differentiate into nearly all cells, i.e., cells derived from any of the three germ layers, including endoderm (interior stomach lining, gastrointestinal tract, the lungs), mesoderm (muscle, bone, blood, urogenital), and ectoderm (epidermal tissues and nervous system).

Multipotent stem cells can differentiate into a number of cells, but only those of a closely related family of cells.

Oligopotent stem cells can differentiate into only a few cells, such as lymphoid or myeloid stem cells.

Unipotent cells can produce only one cell type, their own, but have the property of self-renewal which distinguishes them from non-stem cells (e.g., muscle stem cells).

Embryonic and induced pluripotent stem cells have had an unprecedented impact on our ability to study human diseases and to generate replacement tissues that are therapeutically effective in animal models.

In developmental biology, cellular differentiation is the process by which a less specialized cell becomes a more specialized cell type. Most successful efforts to direct the differentiation of human PSCs into therapeutic cell types have been based on studies of embryonic organ development. Examples include the generation of liver hepatocytes and pancreatic endocrine cells, which have shown functional potential in animal models of liver disease and diabetes. Similarly, differentiation of PSCs into intestine may provide therapeutic benefit for diseases such as necrotizing enterocolitis, inflammatory bowel diseases and short gut syndromes.

As discussed above, a pluripotent stem cell has the potential to differentiate into any of the three germ layers: endoderm (interior stomach lining, gastrointestinal tract, the lungs), mesoderm (muscle, bone, blood, urogenital), and ectoderm (epidermal tissues and nervous system). As such, pluripotent stem cells can give rise to any fetal or adult cell type. However, the fate of the particular pluripotent stem cells is controlled by numerous cellular signaling pathway and numerous factors. Further, the pluripotent stem cells alone cannot develop into a fetal or adult animal because they lack the potential to contribute to extraembryonic tissue, such as the placenta.

What is needed in the art are methods and systems for accurately controlling the destination of the pluripotent stem cells in order to create the specific type of tissue or organism of desire.

SUMMARY OF THE INVENTION

In some embodiments, a method of inducing formation of an intestinal tissue is provided, comprising: activating one or more signaling pathways within a precursor cell.

In some embodiments, the one or more signaling pathways are selected from the group consisting of the Wnt signaling pathway, Wnt/APC signaling pathway, FGF signaling pathway, TGF-beta signaling pathway, shh signaling pathway, BMP signaling pathway, Notch signaling pathway, Hedgehog signaling pathway, LKB signaling pathway, and Par polarity signaling pathway; and obtaining an intestinal tissue descended from said precursor cell.

In some embodiments, the method further comprises: providing said precursor cell. In some embodiments, the method further comprises: culturing, after said activating step, said activated precursor cell in vitro to form a 3-dimensional tissue structure.

In some embodiments, the activating and obtaining steps are conducted in vitro.

In some embodiments, the one or more signaling pathways comprise the Wnt signaling pathway and FGF signaling pathway.

In some embodiments, the Wnt signaling pathway is activated by contacting the precursor cell with one or more molecules selected from the group consisting of Wnt1, Wnt2, Wnt2b, Wnt3, Wnt3a, Wnt4, Wnt5a, Wnt5b, Wnt6, Wnt7a, Wnt7b, Wnt8a, Wnt8b, Wnt9a, Wnt9b, Wnt10a, Wnt10b, Wnt11, and Wnt16.

In some embodiments, the FGF signaling pathway is activated by contacting the precursor cell with one or more molecules selected from the group consisting of FGF1, FGF2, FGF3, FGF4, FGF10, FGF11, FGF12, FGF13, FGF14, FGF15, FGF16, FGF17, FGF18, FGF19, FGF20, FGF21, FGF22, and FGF23.

In some embodiments, the activating step comprises contacting said precursor cell with both Wnt3a and FGF4 over a specified activation period.

In some embodiments, the precursor cell is contacted by Wnt3a during a first activation period and by FGF4 during a second activation period. In some embodiments, the first activation period and the second activation period overlap. In some embodiments, the first activation period and said second activation period do not overlap.

In some embodiments, the specified activation period is between 24 and 120 hours.

In some embodiments, the precursor cell is contacted with Wnt3a at a concentration between 50-1500 ng/ml.

In some embodiments, the said precursor cell is elected from the group consisting of an embryonic stem cell, an embryonic germ cell, an induced pluripotent stem cell, a mesoderm cell, a definitive endoderm cell, a posterior endoderm cell, and a hindgut cell.

In some embodiments, the definitive endoderm cell is derived from a pluripotent stem cell.

In some embodiments, the pluripotent stem cell is an embryonic stem cell, an embryonic stem cell, an adult stem cell, or an induced pluripotent stem cell.

In some embodiments, the definitive endoderm cell is derived by contacting the pluripotent stem cell with one or more molecules selected from the group consisting of Activin, the BMP subgroups of the TGF-beta superfamily of growth factors; Nodal, Activin A, Activin B, BMP4, Wnt3a, and a combinations thereof.

In some embodiments, the pluripotent stem cell is a mammalian pluripotent stem cell, including but not limited to human pluripotent stem cell or a mouse pluripotent stem cell.

In some embodiments, the human pluripotent stem cell is selected from the group consisting of a human embryonic stem cell, a human embryonic germ cell, and an induced human pluripotent stem cell.

In some embodiments, an intestinal tissue produced in vitro from one or more precursor cells is provided.

In some embodiments, the one or more precursor cells are selected from the group consisting of an embryonic stem cell, an embryonic germ cell, an induced pluripotent stem cell, a mesoderm cell, a definitive endoderm cell, a posterior endoderm cell, and a hindgut cell.

In some embodiments, a kit comprising an intestinal tissue produced in vitro from one or more precursor cells is provided.

In some embodiments, a method for identifying the absorption effect of intestinal cells or tissues is provided, comprising: contacting intestinal cells or tissues with a compound, wherein said intestinal cells or tissues are produced in vitro from one or more precursor cells; and detecting a level of absorption of said compound by said intestinal cells or tissues.

BRIEF DESCRIPTION OF THE DRAWINGS

Those of skill in the art will understand that the drawings, described below, are for illustrative purposes only. The drawings are not intended to limit the scope of the present teachings in any way.

FIG. 1A includes bar charts that illustrate that FGF4 and Wnt3a act synergistically in a temporal and dose-dependent manner to specify stable posterior endoderm fate. FIGS. 1B-1D illustrate immunofluorescence images showing the same.

FIG. 2A includes bright field images of definitive endoderm (DE) treated with FGF4 and Wnt3a. FIG. 2B shows immunofluorescent images of the same DE cultures illustrated in FIG. 2A. FIG. 2C includes bright field images of hindgut-like spheroids. FIGS. 2D-2F show immunofluorescent images of CDX2, basal-lateral lamina ("laminin") and E-Cadherin expression in hindgut-like spheroids. FIG. 2G is an immunofluorescent image of CDX2 expression in an e8.5 mouse embryo (sagittal section). FIG. 2H includes bar charts that illustrate RT-qPCR analysis of hindgut-like spheroids for Pdx1, Albumin and CDX2 expression.

FIG. 3A includes images that illustrate the time course of organoid growth for 13 days. FIGS. 3B-3E are immunofluorescent images of characteristic intestinal transcription factor expression and cell proliferation in organoids after 14 and 28 days of culture. FIGS. 3F and 3G are immunofluorescent images of KLF5, CDX2 and SOX9 expression in mouse fetal intestine at e14.5. FIGS. 3H and 3I are whole mount immunofluorescent z-stack images of two different organoids for BrdU, CDX3 and SOX9 expression. FIG. 3J is an immunofluorescent image of human induced pluripotent stem cells ("iPSCs") in which KLF5, CDX2 and localized SOX9 expression is detected.

FIGS. 4A-4C are immunofluorescent images of 28 day iPSC-derived and 38 day H9 HES-derived organoids analyzed for villin (VIL), mucin (MUC2), lysozyme (LYSO) and chromogranin A (CGA). FIG. 4D is an electron micrograph image showing an enterocyte cell with a characteristic brush border with microvilli. FIGS. 4E and 4F are immunofluorescent images of endocrine cell ineage development through adenoviral-mediated expression of Neurogenin 3 (NEUROG3).

FIGS. 5A-5C illustrate exemplary embodiments in accordance with the present invention. FIGS. 5A and 5B are schematic illustrations of human intestinal development and directed differentiation of PSCs into intestinal tissue, respectively. FIG. 5C includes microscopic and immunofluorescent images of mouse embryonic intestinal development (top) and human intestinal organoid development (bottom) in a side-by-side comparison.

FIG. 6A includes immunofluorescent images depicting characterization of DE formation from hESC and iPSC lines. FIG. 6B is a microarray analysis of the transcriptional profile of DE induction in hESC-H9 and iPSC lines before and after DE formation.

FIGS. 7A and 7B include bar charts illustrating exemplary embodiments in accordance with the present invention. The bar charts depict time and concentration dependent induction of CDX2 by FGF4 and Wnt3a.

FIG. 9A includes both bright field and immunofluorescent images which illustrate the characterization of induced pluripotent stem cell lines. FIG. 9B includes examples of karyotypic analysis of iPSC lines 3.5, 3.6 and 16.5.

FIGS. 10A-10G illustrate exemplary embodiments in accordance with the present invention. FIGS. 10A-10G are microscopic images showing the morphologic comparison of hESC and iPSC organoid formation.

FIGS. 11A-11M illustrate exemplary embodiments in accordance with the present invention. FIGS. 11A-11F are immunofluorescent images showing the molecular analysis of stages of epithelial growth, maturation and cytodifferentiation. FIGS. 11G-11M are bar charts of RT-qPCR results illustrating quantitative analysis of intestinal markers SOX9, Villin (enterocytes), Lysozyme (Paneth cells), HOXA13, IFABP (enterocytes) and MMPI (Paneth cells) during intestinal organoid development by RT-qPCR.

FIGS. 12A and 12B illustrate exemplary embodiments in accordance with the present invention. FIGS. 12A and 12B are immunofluorescent images showing GATA factor expression in H9 hESC derived organoids and human iPSC derived organoids, respectively.

FIGS. 13A-13F are immunofluorescent images showing mesenchymal development, in particular expression of the pan-mesenchymal markers Collagen IV (ColIV, red) and Vimentin (Vim, green) and the mesenchymal differentiation marker smooth muscle actin (SMA) during organoid development.

FIGS. 14A-14D illustrate exemplary embodiments in accordance with the present invention. FIG. 14A is a schematic illustration depicting the signaling network that regulates hindgut and intestinal development. FIGS. 14B-14D are bar charts depicting the effects of FGF, WNT, and BMP signaling on differentiation of definitive endoderm into foregut and hindgut.

FIGS. 15A, 15C and 15D are bar charts that illustrate hindgut differentiation in a BMP dependent manner as a result of retinoic acid administration. FIG. 15B is an immunofluorescent image illustrating the effects of Retinoic Acid and inhibition of BMP on differentiation of definitive endoderm into foregut and hindgut.

FIGS. 16A and 16B are bar charts that depict BMP signaling in regulating formation of proximal and distal intestine formation from human embryonic and induced pluripotent stem cells. FIG. 16C includes immunofluorescent images of Noggin/EGF/Rspondid1-treated organoids that express CCK in the epithelium, thus indicating a proximal small bowel fate.

DETAILED DESCRIPTION OF THE INVENTION

Definitions

Figure 1A:
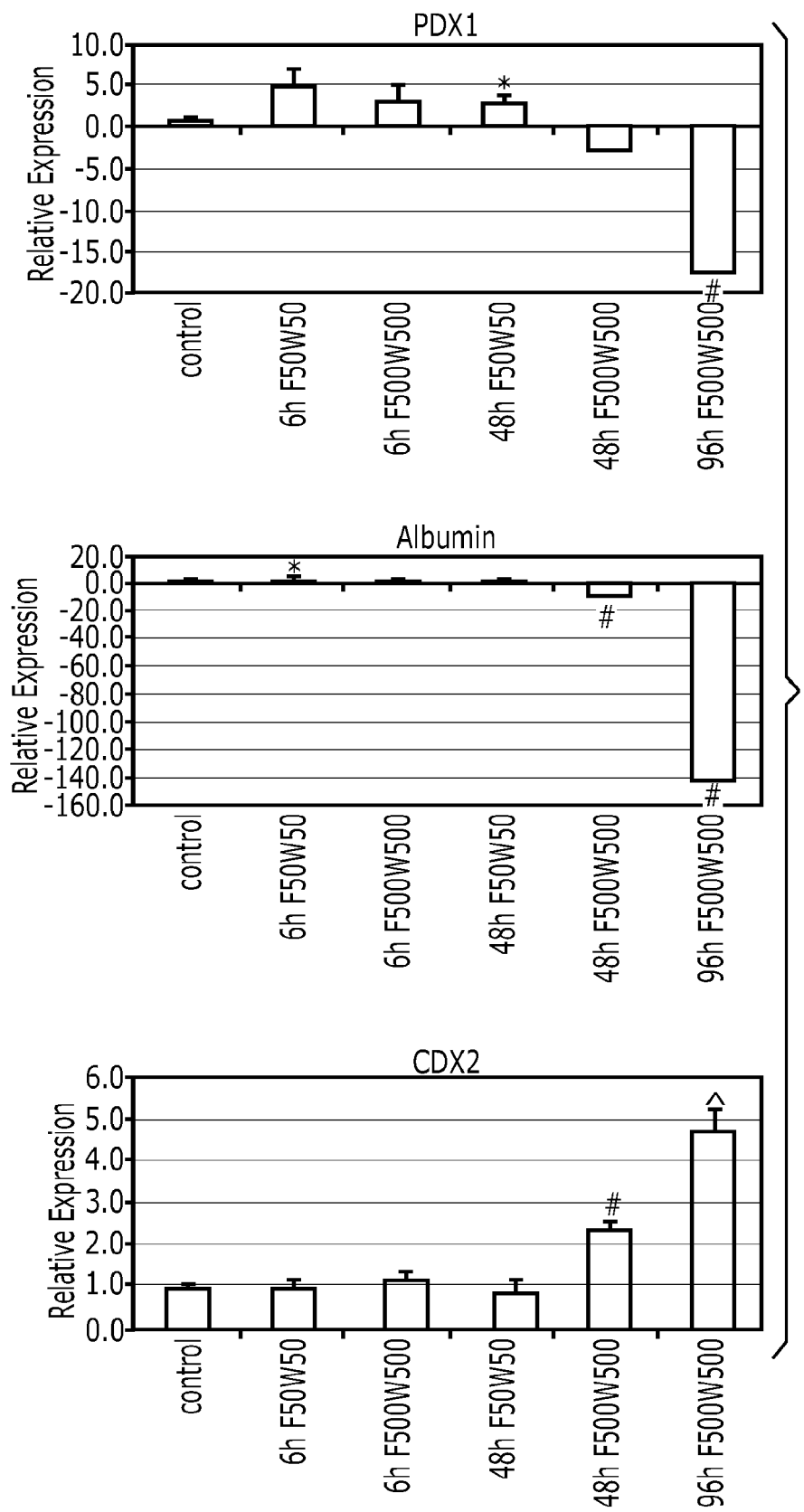
FIGS. 1A-1D illustrate exemplary embodiments of the present invention.

Unless otherwise noted, terms are to be understood according to conventional usage by those of ordinary skill in the relevant art.

As used herein, the term "totipotent stem cells" (also known as omnipotent stem cells) are stem cells that can differentiate into embryonic and extra-embryonic cell types. Such cells can construct a complete, viable, organism. These cells are produced from the fusion of an egg and sperm cell. Cells produced by the first few divisions of the fertilized egg are also totipotent.

As used herein, the term "pluripotent stem cells (PSCs)," also commonly known as PS cells, encompasses any cells that can differentiate into nearly all cells, i.e., cells derived from any of the three germ layers (germinal epithelium), including endoderm (interior stomach lining, gastrointestinal tract, the lungs), mesoderm (muscle, bone, blood, urogenital), and ectoderm (epidermal tissues and nervous system). PSCs can be the descendants of totipotent cells, derived from embryonic stem cells (including embryonic germ cells) or obtained through induction of a non-pluripotent cell, such as an adult somatic cell, by forcing the expression of certain genes.

As used herein, the term "induced pluripotent stem cells (iPSCs)," also commonly abbreviated as iPS cells, refers to a type of pluripotent stem cells artificially derived from a normally non-pluripotent cell, such as an adult somatic cell, by inducing a "forced" expression of certain genes.

As used herein, the term "embryonic stem cells (ESCs)," also commonly abbreviated as ES cells, refers to cells that are pluripotent and derived from the inner cell mass of the blastocyst, an early-stage embryo. For purpose of the present invention, the term "ESCs" is used broadly sometimes to encompass the embryonic germ cells as well.

As used herein, the term "precursor cell" encompasses any cells that can be used in methods described herein, through which one or more precursor cells acquire the ability to renew itself or differentiate into one or more specialized cell types. In some embodiments, a precursor cell is pluripotent or has the capacity to becoming pluripotent. In some embodiments, the precursor cells are subjected to the treatment of external factors (e.g., growth factors) to acquire pluripotency. In some embodiments, a precursor cell can be a totipotent (or omnipotent) stem cell; a pluripotent stem cell (induced or non-induced); a multipotent stem cell; an oligopotent stem cells and a unipotent stem cell. In some embodiments, a precursor cell can be from an embryo, an infant, a child, or an adult. In some embodiments, a precursor cell can be a somatic cell subject to treatment such that pluripotency is conferred via genetic manipulation or protein/peptide treatment.

In developmental biology, cellular differentiation is the process by which a less specialized cell becomes a more specialized cell type. As used herein, the term "directed differentiation" describes a process through which a less specialized cell becomes a particular specialized target cell type. The particularity of the specialized target cell type can be determined by any applicable methods that can be used to define or alter the destiny of the initial cell. Exemplary methods include but are not limited to genetic manipulation, chemical treatment, protein treatment, and nucleic acid treatment.

As used herein, the term "cellular constituents" are individual genes, proteins, mRNA expressing genes, and/or any other variable cellular component or protein activities such as the degree of protein modification (e.g., phosphorylation), for example, that is typically measured in biological experiments (e.g., by microarray or immunohistochemistry) by those skilled in the art. Significant discoveries relating to the complex networks of biochemical processes underlying living systems, common human diseases, and gene discovery and structure determination can now be attributed to the application of cellular constituent abundance data as part of the research process. Cellular constituent abundance data can help to identify biomarkers, discriminate disease subtypes and identify mechanisms of toxicity.

As described herein, methods and systems are established using a temporal series of growth factor manipulations to mimic embryonic intestinal development in culture. In particular, methods and systems are established to direct in vitro the differentiation of PSCs, both human embryonic stem cells (hESC) and induced pluripotent stem cells (iPSC), into intestinal tissue (for example, as depicted in FIGS. 5a and 5b). These factors directed human intestinal development in vitro in stages that approximate fetal gut development: activin-induced definitive endoderm (DE) formation; FGF/Wnt induced posterior endoderm pattering, hindgut specification and morphogenesis; and finally a pro-intestinal culture system that promoted intestinal growth, morphogenesis and cytodifferentiation into functional intestinal cell types including enterocytes, goblet, Paneth and enteroendocrine cells.

Pluripotent Stem Cells Derived from Embryonic Cells

In some embodiments, an important step is to obtain stem cells that are pluripotent or can be induced to become pluripotent. In some embodiments, pluripotent stem sells are derived from embryonic stem cells, which are in turn derived from totipotent cells of the early mammalian embryo and are capable of unlimited, undifferentiated proliferation in vitro. Embryonic stem cells are pluripotent stem cells derived from the inner cell mass of the blastocyst, an early-stage embryo. Methods for deriving embryonic stem cells from blastocytes are well known in the art. For example, three cell lines (H1, H13, and H14) had a normal XY karyotype, and two cell lines (H7 and H9) had a normal XX karyotype. Human embryonic stem cells H9 (H9-hESCs) are used in the exemplary embodiments described in the present application, but it would be understood by one of skill in the art that the methods and systems described herein are applicable to any stem cells.

Additional stem cells that can be used in embodiments in accordance with the present invention include but are not limited to those provided by or described in the database hosted by the National Stem Cell Bank (NSCB), Human Embryonic Stem Cell Research Center at the University of California, San Francisco (UCSF); WISC cell Bank at the Wi Cell Research Institute; the University of Wisconsin Stem Cell and Regenerative Medicine Center (UW-SCRMC); Novocell, Inc. (San Diego, Calif.); Cellartis AB (Göteborg, Sweden); ES Cell International Pte Ltd (Singapore); Technion at the Israel Institute of Technology (Haifa, Israel); and the Stem Cell Database hosted by Princeton University and the University of Pennsylvania. Exemplary embryonic stem cells that can be used in embodiments in accordance with the present invention include but are not limited to SA01 (SA001); SA02 (SA002); ES01 (HES-1); ES02 (HES-2); ES03 (HES-3); ES04 (HES-4); ES05 (HES-5); ES06 (HES-6); BG01 (BGN-01); BG02 (BGN-02); BG03 (BGN-03); TE03 (13); TE04 (I4); TE06 (I6); UC01 (HSF1); UC06 (HSF6); WA01 (H1); WA07 (H7); WA09 (H9); WA13 (H13); WA14 (H14).

In some embodiments, the stem cells are further modified to incorporate additional properties. Exemplary modified cell lines include but not limited to H1 OCT4-EGFP; H9 Cre-LoxP; H9 hNanog-pGZ; H9 hOct4-pGZ; H9 inGF-PhES; and H9 Syn-GFP.

More details on embryonic stem cells can be found in, for example, Thomson et al., 1998, "Embryonic Stem Cell Lines Derived from Human Blastocysts," *Science* 282 (5391):1145-1147; Andrews et al., 2005, "Embryonic stem (ES) cells and embryonal carcinoma (EC) cells: opposite sides of the same coin," *Biochem Soc Trans* 33:1526-1530; Martin 1980, "Teratocarcinomas and mammalian embryogenesis,". *Science* 209 (4458):768-776; Evans and Kaufman, 1981, "Establishment in culture of pluripotent cells from mouse embryos," *Nature* 292(5819): 154-156; Klimanskaya et al., 2005, "Human embryonic stem cells derived without feeder cells," *Lancet* 365 (9471): 1636-1641; each of which is hereby incorporated herein in its entirety.

Alternative, pluripotent stem cells can be derived from embryonic germ cells (EGCs), which are the cells that give rise to the gametes of organisms that reproduce sexually. EGCs are derived from primordial germ cells found in the gonadal ridge of a late embryo, have many of the properties of embryonic stem cells. The primordial germ cells in an embryo develop into stem cells that in an adult generate the reproductive gametes (sperm or eggs). In mice and humans it is possible to grow embryonic germ cells in tissue culture under appropriate conditions. Both EGCs and ESCs are pluripotent. For purpose of the present invention, the term "ESCs" is used broadly sometimes to encompass EGCs.

Induced Pluripotent Stem Cells (iPSCs)

In some embodiments, iPSCs are derived by transfection of certain stem cell-associated genes into non-pluripotent cells, such as adult fibroblasts. Transfection is typically achieved through viral vectors, such as retroviruses. Transfected genes include the master transcriptional regulators Oct-3/4 (Pouf51) and Sox2, although it is suggested that other genes enhance the efficiency of induction. After 3-4 weeks, small numbers of transfected cells begin to become morphologically and biochemically similar to pluripotent stem cells, and are typically isolated through morphological selection, doubling time, or through a reporter gene and antibiotic selection. As used herein, iPSCs include but are not limited to first generation iPSCs, second generation iPSCs in mice, and human induced pluripotent stem cells. In some embodiments, a retroviral system is used to transform human fibroblasts into pluripotent stem cells using four pivotal genes: Oct3/4, Sox2, Klf4, and c-Myc. In alternative embodiments, a lentiviral system is used to transform somatic cells with OCT4, SOX2, NANOG, and LIN28. Genes whose expression are induced in iPSCs include but are not limited to Oct-3/4 (e.g., Pou5f1); certain members of the Sox gene family (e.g., Sox1, Sox2, Sox3, and Sox15); certain members of the Klf family (e.g., Klf1, Klf2, Klf4, and Klf5), certain members of the Myc family (e.g., C-myc, L-myc, and N-myc), Nanog, and LIN28.

In some embodiments, non-viral based technologies are employed to generate iPSCs. In some embodiments, an adenovirus can be used to transport the requisite four genes into the DNA of skin and liver cells of mice, resulting in cells identical to embryonic stem cells. Since the adenovirus does not combine any of its own genes with the targeted host, the danger of creating tumors is eliminated. In some embodiments, reprogramming can be accomplished via plasmid without any virus transfection system at all, although at very low efficiencies. In other embodiments, direct delivery of proteins is used to generate iPSCs, thus eliminating the need for viruses or genetic modification. In some embodiment, generation of mouse iPSCs is possible using a similar methodology: a repeated treatment of the cells with certain proteins channeled into the cells via poly-arginine anchors was sufficient to induce pluripotency. In some embodiments, the expression of pluripotency induction genes can also be increased by treating somatic cells with FGF2 under low oxygen conditions.

More details on embryonic stem cells can be found in, for example, Kaji et al., 2009, "Virus free induction of pluripotency and subsequent excision of reprogramming factors," *Nature* 458:771-775; Woltjen et al., 2009, "piggyBac transposition reprograms fibroblasts to induced pluripotent stem cells," *Nature* 458:766-770; Okita et al., 2008, "Generation of Mouse Induced Pluripotent Stem Cells Without Viral Vectors," *Science* 322(5903):949-953; Stadtfeld et al., 2008, "Induced Pluripotent Stem Cells Generated without Viral Integration," *Science* 322(5903):945-949; and Zhou et al., 2009, "Generation of Induced Pluripotent Stem Cells Using Recombinant Proteins," *Cell Stem Cell* 4(5):381-384; each of which is hereby incorporated herein in its entirety.

In some embodiments, exemplary iPS cell lines include but not limited to iPS-DF19-9; iPS-DF19-9; iPS-DF4-3; iPS-DF6-9; iPS(Foreskin); iPS(IMR90); and iPS(IMR90).

It has been shown that iPSCs were capable of differentiation in a fashion similar to ESCs into fully differentiated tissues. For example, iPSCs were differentiated into neurons, expressing βIII-tubulin, tyrosine hydroxylase, AADC, DAT, ChAT, LMX1B, and MAP2. The presence of catecholamine-associated enzymes may indicate that iPSCs, like hESCs, may be differentiable into dopaminergic neurons. Stem cell-associated genes were shown to be down-regulated after differentiation. It was also shown that iPSCs were differentiated into cardiomyocytes that spontaneously began beating. Cardiomyocytes expressed TnTc, MEF2C, MYL2A, MYHCβ, and NKX2.5. Stem cell-associated genes were down-regulated after differentiation.

Intestinal Organ and Development

No systems were available prior to the present invention for converting embryonic stem cells and/or iPSCs into intestinal tissues. In anatomy, the intestine (or bowel) is the segment of the alimentary canal extending from the stomach to the anus and, in humans and other mammals, consists of two segments, the small intestine and the large intestine. In humans, the small intestine is further subdivided into the duodenum, jejunum and ileum while the large intestine is subdivided into the cecum and colon. The structure of an intestinal organ is described herein using the human organ as an example. It will be understood by one of ordinary skill in the art that the methods and systems described herein are applicable to the intestinal systems of all mammals.

The intestinal tract can be broadly divided into two different parts, the small and large intestine. Grayish-purple in color and about 35 millimeters (1.5 inches) in diameter, the small intestine is the first and longer, measuring 6 to 7 meters (20-23 feet) long average in an adult man. Shorter and relatively stockier, the large intestine is a dark reddish color, measuring roughly 1.5 meters (5 feet) long on average.

The lumen is the cavity where digested food passes through and from where nutrients are absorbed. Both intestines share a general structure with the whole gut, and are composed of several layers.

Going from inside the lumen radially outwards, one passes the mucosa (glandular epithelium and muscularis mucosa), submucosa, muscularis externa (made up of inner circular and outer longitudinal), and lastly serosa. Along the whole length of the gut in the glandular epithelium are goblet cells. These secrete mucus which lubricates the passage of food and protects the gut from digestive enzymes. Villi are vaginations of the mucosa and increase the overall surface area of the intestine while also containing a lacteal, which is connected to the lymph system and aids in the removal of lipids and tissue fluid from the blood supply. Microvilli are present on the epithelium of a villus and further increase the surface area over which absorption can take place. The muscularis mucosa is a layer of smooth muscle that aids in the action of continued peristalsis and catastalsis along the gut. The submucosa contains nerves (e.g., Meissner's plexus), blood vessels and elastic fibre with collagen that stretches with increased capacity but maintains the shape of the intestine. The muscularis externa comprises longitudinal and smooth muscle that again helps with continued peristalsis and the movement of digested material out of and along the gut. In between the two layers of muscle lies Auerbach's plexus. The serosa is made up of loose connective tissue and coated in mucus so as to prevent friction damage from the intestine rubbing against other tissue. Holding all this in place are the mesenteries which suspend the intestine in the abdominal cavity and stop it from being disturbed when a person is physically active.

In some embodiments, PSCs, such as ESCs and iPSCs, undergo directed differentiation in a step-wise manner first into definitive endoderm (DE) then into posterior/hindgut epithelium (e.g., hindgut spheroids), and then into intestinal tissue.

In some embodiments, PSCs, such as ESCs and iPSCs, undergo directed differentiation in a non step-wise manner where molecules (e.g., growth factors, ligands) for promoting DE formation and those for subsequent tissue formation are added at the same time.

Definitive Endoderm

The epithelium of the intestine is derived from a simple sheet of cells called the definitive endoderm (DE). The anterior DE forms the foregut and its associated organs including the liver and pancreas and the posterior DE forms the midgut and hindgut, which forms the small and large intestines and parts of the genitourinary system. Studies using mouse, chick and frog embryos suggest that establishing the anterior-posterior pattern in DE at the gastrula stage is a prerequisite for subsequent foregut and hindgut development. The Wnt and FGF signaling pathways are critical for this process and act to promote posterior endoderm and hindgut fate and suppress anterior endoderm and foregut fate. The simple cuboidal epithelium of the hindgut first develops into a pseudostratified columnar epithelium, then into villi containing a polarized columnar epithelium and a proliferative zone at the base of the villi, which corresponds with the presumptive progenitor domain.

A robust and efficient process is established to direct the differentiation of DE into intestinal tissue in vitro. In some embodiments, directed differentiation is achieved by selectively activating certain signaling pathways in the iPSCs and/or DE cells. In some embodiments, the signaling pathways are those active in intestinal development, including but not limited to the Wnt signaling pathway; Wnt/APC signaling pathway; FGF signaling pathway; TGF-beta signaling pathway; BMP signaling pathway; Notch signaling pathway; Hedgehog signaling pathway; LKB signaling pathway; and Par polarity signaling pathway.

Additional details of pathways relating to intestinal development in general are found in, for example, Sancho et al., 2004, "Signaling Pathways in Intestinal Development and Cancer," *Annual Review of Cell and Developmental Biology* 20:695-723; Logan and Nusse, 2004, "The Wnt Signaling Pathway in Development and Disease," *Annual Review of Cell and Developmental Biology* 20:781-810; Taipalel and Beachyl, 2001, "The Hedgehog and Wnt signalling pathways in cancer," *Nature* 411:349-354; Gregorieff and Clevers, 2005, "Wnt signaling in the intestinal epithelium: from endoderm to cancer," *Genes & Dev.* 19: 877-890; each of which is hereby incorporated by reference herein in its entirety.

More details on the functions of signaling pathways relating to DE development can be found in, for example, Zorn and Wells, 2009, "Vertebrate endoderm development and organ formation," *Annu Rev Cell Dev Biol* 25:221-251; Dessimoz et al., 2006, "FGF signaling is necessary for establishing gut tube domains along the anterior-posterior axis in vivo," *Mech Dev* 123:42-55; McLin et al., 2007, "Repression of Wnt/{beta}-catenin signaling in the anterior endoderm is essential for liver and pancreas development. Development," 134:2207-2217; Wells and Melton, 2000, *Development* 127:1563-1572; de Santa Barbara et al., 2003, "Development and differentiation of the intestinal epithelium," *Cell Mol Life Sci* 60(7): 1322-1332; each of which is hereby incorporated herein in its entirety.

Any methods for producing definitive endoderm from pluripotent cells (e.g., iPSCs or ESCs) are applicable to the methods described herein. In some embodiments, pluripotent cells are derived from a morula. In some embodiments, pluripotent stem cells are stem cells. Stem cells used in these methods can include, but are not limited to, embryonic stem cells. Embryonic stem cells can be derived from the embryonic inner cell mass or from the embryonic gonadal ridges. Embryonic stem cells or germ cells can originate from a variety of animal species including, but not limited to, various mammalian species including humans. In some embodiments, human embryonic stem cells are used to produce definitive endoderm. In some embodiments, human embryonic germ cells are used to produce definitive endoderm. In some embodiments, iPSCs are used to produce definitive endoderm.

In some embodiments, one or more growth factors are used in the differentiation process from pluripotent stem cells to DE cells. The one or more growth factors used in the differentiation process can include growth factors from the TGF-beta superfamily. In such embodiments, the one or more growth factors comprise the Nodal/Activin and/or the BMP subgroups of the TGF-beta superfamily of growth factors. In some embodiments, the one or more growth factors are selected from the group consisting of Nodal, Activin A, Activin B, BMP4, Wnt3a or combinations of any of these growth factors.

In some embodiments, the embryonic stem cells or germ cells and iPSCs are treated with the one or more growth factors for 6 or more hours; 12 or more hours; 18 or more hours; 24 or more hours; 36 or more hours; 48 or more hours; 60 or more hours; 72 or more hours; 84 or more hours; 96 or more hours; 120 or more hours; 150 or more hours; 180 or more hours; or 240 or more hours.

In some embodiments, the embryonic stem cells or germ cells and iPSCs are treated with the one or more growth factors at a concentration of 10 ng/ml or higher; 20 ng/ml or higher; 50 ng/ml or higher; 75 ng/ml or higher; 100 ng/ml or higher; 120 ng/ml or higher; 150 ng/ml or higher; 200 ng/ml or higher; 500 ng/ml or higher; 1,000 ng/ml or higher; 1,200 ng/ml or higher; 1,500 ng/ml or higher; 2,000 ng/ml or higher; 5,000 ng/ml or higher; 7,000 ng/ml or higher; 10,000 ng/ml or higher; or 15,000 ng/ml or higher. In some embodiments, concentration of the growth factor is maintained at a constant level throughout the treatment. In other embodiments, concentration of the growth factor is varied during the course of the treatment. In some embodiments, the growth factor is suspended in media that include fetal bovine serine (FBS) with varying HyClone concentrations. One of skill in the art would understand that the regimen described herein is applicable to any known growth factors, alone or in combination. When two or more growth factors are used, the concentration of each growth factor may be varied independently.

In some embodiments, populations of cells enriched in definitive endoderm cells are used. In some embodiments, the definitive endoderm cells are isolated or substantially purified. In some embodiments, the isolated or substantially purified definitive endoderm cells express the SOX17, FOXA2, and/or the CXRC4 marker to a greater extent than the OCT4, AFP, TM, SPARC and/or SOX7 markers.

Methods for enriching a cell population with definitive endoderm are also contemplated. In some embodiments, definitive endoderm cells can be isolated or substantially purified from a mixed cell population by contacting the cells with a reagent that binds to a molecule that is present on the surface of definitive endoderm cells but which is not present on the surface of other cells in the mixed cell population, and then isolating the cells bound to the reagent. In certain embodiments, the cellular constituent that is present on the surface of definitive endoderm cells is CXCR4.

Still other embodiments of the present invention relate to CXCR4 antibodies, SDF-1 ligands or other ligands for CXCR4 can be used to obtain definitive endoderm cells in an enriched, isolated or substantially purified form. For example, a CXCR4 antibody, an SDF-1 ligand or another ligand for CXCR4 can be used as a reagent in a method, such as affinity-based separation or magnetic-based separation, to enrich, isolate or substantially purify preparations of definitive endoderm cells that bind to the reagent.

In some embodiments of the present invention, definitive endoderm cells and hESCs are treated with one or more growth factors. Such growth factors can include growth factors from the TGF-beta superfamily. In such embodiments, the one or more growth factors comprise the Nodal/Activin and/or the BMP subgroups of the TGF-beta superfamily of growth factors. In some embodiments, the one or more growth factors are selected from the group consisting of Nodal, Activin A, Activin B, BMP4, Wnt3a or combinations of any of these growth factors.

Additional methods for obtaining or creating DE cells that can be used in the present invention include but are not limited to those described in U.S. Pat. No. 7,510,876 to D'Amour et al.; U.S. Pat. No. 7,326,572 to Fisk et al.; Kubol et al., 2004, "Development of definitive endoderm from embryonic stem cells in culture," Development 131:1651-1662; D'Amour et al., 2005, "Efficient differentiation of human embryonic stem cells to definitive endoderm," Nature Biotechnology 23:1534-1541; and Ang et al., 1993, "The formation and maintenance of the definitive endoderm lineage in the mouse: involvement of HNF3/forkhead proteins," *Development* 119:1301-1315; each of which is hereby incorporated by reference herein in its entirety.

Directed Differentiation of Posteriorized DE

In some embodiments, activin-induced definitive endoderm (DE) can further undergo FGF/Wnt induced posterior endoderm pattering, hindgut specification and morphogenesis, and finally a pro-intestinal culture system that promoted intestinal growth, morphogenesis and cytodifferentiation into functional intestinal cell types including enterocytes, goblet, Paneth and enteroendocrine cells. In some embodiments, human PSCs are efficiently directed to differentiate in vitro into intestinal epithelium that includes secretory, endocrine and absorptive cell types. It will be understood that molecules such as growth factors can be added to any stage of the development to promote a particular type of intestinal tissue formation.

In some embodiments, posteriorized endoderm cells of the DE are further developed into one or more specialized cell types.

In some embodiments, soluble FGF and Wnt ligands are used to mimic early hindgut specification in culture to convert, through directed differentiation, DE developed from iPSCs or ESCs into hindgut epithelium that efficiently gives rise to all the major intestinal cell types. In human, directed differentiation of DE is achieved through selective activating certain signaling pathways that are important to intestinal development.

Human intestinal development in vitro occurs in stages that approximate fetal gut development; endoderm formation, posterior endoderm patterning, hindgut morphogenesis, fetal gut development, epithelial morphogenesis, formation of a presumptive progenitor domain, and differentiation into functional cell types of the intestine. For example, in human, genes that encode Wnt signaling proteins include but are not limited to Wnt1, Wnt2, Wnt2b, Wnt3, Wnt3a, Wnt4, Wnt5a, Wnt5b, Wnt6, Wnt7a, Wnt7b, Wnt8a, Wnt8b, Wnt9a, Wnt9b, Wnt10a, Wnt10b, Wnt11, and Wnt16.

It will be understood by one of skill in the art that altering the expression of any Wnt signaling protein in combination with any FGF ligand can give rise to directed differentiation in accordance of the present invention. In some embodiments, the alteration is over-expression of Wnt3, in particular Wnt3a. In some embodiments, the alternation is over-expression of Wnt1.

It will be understood by one of skill in the art that altering the signaling activity of the Wnt signaling pathway in combination with altering the signaling activity of the FGF signaling pathway can give rise to directed differentiation in accordance of the present invention. In some embodiments, the alteration is through the use of small molecule modulators that activate the aforementioned pathways. For example, Small molecule modulators of the Wnt pathway included, but is not limited to Lithium Chloride; 2-amino-4,6-disubstituted pyrimidine (hetero) arylpyrimidines; IQ1; QS11; NSC668036; DCA beta-catenin; 2-amino-4-[3,4-(methylenedioxy)-benzyl-amino]-6-(3-methoxyphenyl) pyrimidine.

In alternative embodiments, cellular constituents associated with the Wnt and/or FGF signaling pathways, for example, natural inhibitors or antagonist of the pathways can be inhibited to result in activation of the Wnt and/or FGF signaling pathways.

In some embodiment, the cellular constituents are inhibited by other cellular constituents or extrinsic molecules. Exemplary natural inhibitors of Wnt signaling include but are not limited to Dkk1, SFRP proteins and FrzB. In some embodiments, the extrinsic molecules includes but are not limited to small molecules such as WAY-316606; SB-216763; or BIO (6-bromoindirubin-3'-oxime).

More details are found, for example, in Liu et al., "A small-molecule agonist of the Wnt signaling pathway," *Angew Chem Int Ed Engl.* 44(13):1987-1990 (2005); Miyabayashi et al., "Wnt/beta-catenin/CBP signaling maintains long-term murine embryonic stem cell pluripotency," *Proc Natl Acad Sci USA.* 104(13):5668-5673 (2007); Zhang et al., "Small-molecule synergist of the Wnt/beta-catenin signaling pathway," *Proc Natl Acad Sci USA.* 104(18):7444-7448 (2007); Neiiendam et al., "An NCAM-derived FGF-receptor agonist, the FGL-peptide, induces neurite outgrowth and neuronal survival in primary rat neurons," *J Neurochem.* 91(4):920-935 (2004); Shan et al., "Identification of a specific inhibitor of the dishevelled PDZ domain," *Biochemistry* 44(47):15495-15503 (2005); Coghlan et al., "Selective small molecule inhibitors of glycogen synthase kinase-3 modulate glycogen metabolism and gene transcription," *Chem Biol.* 7(10):793-803 (2000); Coghlan et al., "Selective small molecule inhibitors of glycogen synthase kinase-3 modulate glycogen metabolism and gene transcription," Chemistry & Biology 7(10):793-803; and Pai et al., "Deoxycholic acid activates beta-catenin signaling pathway and increases colon cell cancer growth and invasiveness," *Mol Biol Cell.* 15(5):2156-2163 (2004); each of which is hereby incorporated by reference in its entirety.

In some embodiments, siRNA and/or shRNA targeting cellular constituents associated with the Wnt and/or FGF signaling pathways are used to activate these pathways. It would be understood by one of skill in the art that the target cellular constituents include but are not limited to SFRP proteins; GSK3, Dkk1, and FrzB.

More details about RNAi based technologies can be found, for example, inCouzin, 2002, *Science* 298:2296-2297; McManus et al., 2002, *Nat. Rev. Genet.* 3, 737-747; Hannon, G. J., 2002, *Nature* 418, 244-251; Paddison et al., 2002, *Cancer Cell* 2, 17-23; Elbashir et al., 2001. *EMBO J.* 20:6877-6888; Tuschl et al., 1999, *Genes Dev.* 13:3191-3197; Hutvagner et al., *Sciencexpress* 297:2056-2060; each of which is hereby incorporated by reference in its entirety.

Fibroblast growth factors (FGFs) are a family of growth factors involved in angiogenesis, wound healing, and embryonic development. The FGFs are heparin-binding proteins and interactions with cell-surface associated heparan sulfate proteoglycans have been shown to be essential for FGF signal transduction. FGFs are key players in the processes of proliferation and differentiation of wide variety of cells and tissues. In humans, 22 members of the FGF family have been identified, all of which are structurally related signaling molecules. Members FGF1 through FGF10 all bind fibroblast growth factor receptors (FGFRs). FGF1 is also known as acidic, and FGF2 is also known as basic fibroblast growth factor. Members FGF11, FGF12, FGF13, and FGF14, also known as FGF homologous factors 1-4 (FHF1-FHF4), have been shown to have distinct functional differences compared to the FGFs. Although these factors possess remarkably similar sequence homology, they do not bind FGFRs and are involved in intracellular processes unrelated to the FGFs. This group is also known as "iFGF." Members FGF16 through FGF23 are newer and not as well characterized. FGF15 is the mouse ortholog of human FGF19 (hence there is no human FGF15). Human FGF20 was identified based on its homology to Xenopus FGF-20 (XFGF-20). In contrast to the local activity of the other FGFs, FGF15/FGF19, FGF21 and FGF23 have more systemic effects.

In some embodiments, it will be understood by one of skill in the art that any of the FGFs can be used in conjunction with a protein from the Wnt signaling pathway. In some embodiments, soluble FGFs include and but are not limited to FGF4, FGF2, and FGF3.

In some embodiment, the cellular constituents of the FGF signaling pathway are inhibited by other cellular constituents or extrinsic molecules. Exemplary natural inhibitors of FGF signaling include but are not limited to the Sprouty family of proteins and the Spred family of proteins. As discussed above, proteins, small molecules, nucleic acids can be used to activating the FGF signaling pathway.

It will be understood by one of skill in the art that the methods and compositions described herein in connection with the Wnt and FGF signaling pathways are provided by way of examples. Similar methods and compositions are applicable to other signaling pathways disclosed herein.

In some embodiments, DE culture is treated with the one or more molecules of a signaling pathway described herein for 6 or more hours; 12 or more hours; 18 or more hours; 24 or more hours; 36 or more hours; 48 or more hours; 60 or more hours; 72 or more hours; 84 or more hours; 96 or more hours; 120 or more hours; 150 or more hours; 180 or more hours; 200 or more hours, 240 or more hours; 270 or more hours; 300 or more hours; 350 or more hours; 400 or more hours; 500 or more hours; 600 or more hours; 700 or more hours; 800 or more hours; 900 or more hours; 1,000 or more hours; 1,200 or more hours; or 1,500 or more hours.

In some embodiments, DE culture is treated with the one or more molecules of a signaling pathway described herein at a concentration of 10 ng/ml or higher; 20 ng/ml or higher; 50 ng/ml or higher; 75 ng/ml or higher; 100 ng/ml or higher; 120 ng/ml or higher; 150 ng/ml or higher; 200 ng/ml or higher; 500 ng/ml or higher; 1,000 ng/ml or higher; 1,200 ng/ml or higher; 1,500 ng/ml or higher; 2,000 ng/ml or higher; 5,000 ng/ml or higher; 7,000 ng/ml or higher; 10,000 ng/ml or higher; or 15,000 ng/ml or higher. In some embodiments, concentration of signaling molecule is maintained at a constant throughout the treatment. In other embodiments, concentration of the molecules of a signaling pathway is varied during the course of the treatment. In some embodiments, a signaling molecule in accordance with the present invention is suspended in media comprising DMEM and fetal bovine serine (FBS). The FBS can be at a concentration of 2% and more; 5% and more; 10% or more; 15% or more; 20% or more; 30% or more; or 50% or more. One of skill in the art would understand that the regiment described herein is applicable to any known molecules of the signaling pathways described herein, alone or in combination, including but not limited to any molecules in the Wnt and FGF signaling pathways.

In embodiments where two or more signaling molecules are used to treat the DE culture, the signaling molecules can be added simultaneously or separately. When two or more molecules are use, the concentration of each may be varied independently.

Differentiation of PSCs into DE culture and subsequently into various intermediate mature intestinal cell types can be determined by the presence of stage-specific cell markers. In some embodiments, expression of representative cellular constituents is used to determine DE formation. The representative cellular constituents include but are not limited to CMKOR1, CXCR4, GPR37, RTN4RL1, SLC5A9, SLC40A1, TRPA1, AGPAT3, APOA2, C20orf56, C21orf129, CALCR, CCL2, CER1, CMKOR1, CRIP1, CXCR4, CXorf1, DIO3, DIO3OS, EB-1, EHHADH, ELOVL2, EPSTI1, FGF17, FLJ10970, FLJ21195, FLJ22471, FLJ23514, FOXA2, FOXQ1, GATA4, GPR37, GSC, LOC283537, MYL7, NPPB, NTN4, PRSS2, RTN4RL1, SEMA3E, SIAT8D, SLC5A9, SLC40A1, SOX17, SPOCK3, TMOD1, TRPA1, TTN, AW166727, AI821586, BF941609, AI916532, BC034407, N63706 and AW772192.

Additional cellular constituents suitable for detecting DE formation can be found in, for example, in U.S. patent application Ser. No. 11/165,305, filed Jun. 23, 2005; U.S. patent application Ser. No. 11/317,387, filed Dec. 22, 2005; U.S. patent Ser. No. 11/021,618, filed Dec. 23, 2004; U.S. patent application Ser. Nos. 11/021,618, 11/115,868 filed on Apr. 26, 2005; U.S. patent application Ser. No. 11/317,387, filed on Dec. 22, 2005; U.S. patent application Ser. No. 11/474,211, filed on Jun. 23, 2006; U.S. patent application Ser. No. 11/165,305, filed on Jun. 23, 2005; U.S. patent application Ser. No. 11/587,735 filed on Aug. 29, 2008; U.S. patent application Ser. No. 12/039,701, filed on Feb. 28, 2008; U.S. patent application Ser. No. 12/414,482, filed on Mar. 30, 2009; U.S. patent application Ser. No. 12/476,570, filed on Jun. 2, 2009; U.S. patent application Ser. No. 12/093,590 filed on Jul. 21, 2008; U.S. patent application Ser. No. 12/582,600 filed on Oct. 20, 2009; each of which is hereby incorporated by reference herein in its entirety.

In some embodiments, expression of CDX2 is used to reveal tendency of hindgut formation after DE have been incubated with FGF4 and Wnt3a for a period of time, for example, for 12 hours or longer; 18 hours or longer; 24 hours or longer; 36 hours or longer; 48 hours or longer; 60 hours or longer; or 90 hours or longer. In some embodiments, longer periods of incubation are needed to achieve a stable posterior endoderm phenotype as measured by prolonged expressed of CDX2. In such embodiments, the periods of incubation can be for 60 hours or longer; 72 hours or longer; 84 hours or longer; 96 hours or longer; 108 hours or longer; 120 hours or longer; 140 hours or longer; 160 hours or longer; 180 hours or longer; 200 hours or longer; 240 hours or longer; or 300 hours or longer.

Alternatively, in some embodiments, the absence of cellular constituents, such as foregut markers Pdx1 and Albumin, can be used to reveal directed hindgut formation. In some embodiments, intestinal transcription factors CDX2, KLF5 and SOX9 can be used to represent intestinal development. In some embodiments, GATA4 and/or GATA6 protein expression can be used to represent intestinal development. In these embodiments, the periods of incubation can be for 12 hours or longer; 18 hours or longer; 24 hours or longer; 36 hours or longer; 48 hours or longer; 60 hours or longer; or 90 hours or longer. Alternatively, the periods of incubation can be for 60 hours or longer; 72 hours or longer; 84 hours or longer; 96 hours or longer; 108 hours or longer; 120 hours or longer; 140 hours or longer; 160 hours or longer; 180 hours or longer; 200 hours or longer; 240 hours or longer; or 300 hours or longer.

In some embodiments, abundance data of cellular constituents, for example, protein and/or gene expression levels, are determined by immunohistochemistry using primary and/or secondary antibodies targeting molecules in the relevant signaling pathways. In other embodiments, abundance data of cellular constituents, for example, protein and/or gene expression levels, are determined by microarray analyses.

Still alternatively, morphological changes can be used to represent the progress of directed differentiation. In some embodiments, hindgut spheroids are further subject to 3-dimensional culture conditions for further maturation. In other embodiments, a highly convoluted epithelium surrounded by mesenchymal cells can be observed following hindgut spheroids formation. Additionally, intestinal organoids; polarized columnar epithelium; goblet cells; or smooth muscle cells can be observed in 6 days or longer; 7 days or longer; 9 days or longer; 10 days or longer; 12 days or longer; 15 days or longer; 20 days or longer; 25 days or longer; 28 days or longer; 32 days or longer; 36 days or longer; 40 days or longer; 45 days or longer; 50 days or longer; or 60 days or longer.

Directed Differentiation of Pluripotent Stem Cells

In some embodiments, pluripotent stem cells are converted into intestinal cell types via a "one step" process. For example, one or more molecules that can differentiate pluripotent stem cells into DE culture (e.g., ActivinA) are combined with additional molecules that can promote directed differentiation of DE culture (e.g., Wnt3a and FGF4) to directly treat pluripotent stem cells.

Utilities and Kits Embodiments

In some embodiments, intestinal tissue or related cell types described herein can be used to screen drugs for intestinal uptake and mechanisms of transport. For example, this can be done in a high throughput manner to screen for the most readily absorbed drugs, and can augment Phase 1 clinical trials that are done to study drug intestinal uptake and intestinal toxicity. This includes pericellular and intracellular transport mechanisms of small molecules, peptides, metabolites, salts.

In some embodiments, intestinal tissue or related cell types described herein can be used to identify the molecular basis of normal human intestinal development.

In some embodiments, intestinal tissue or related cell types described herein can be used to identify the molecular basis of congenital defects affecting human intestinal development.

In some embodiments, intestinal tissue or related cell types described herein can be used to correct intestinal congenital defects caused by genetic mutations. In particular, mutation affecting human intestinal development can be corrected using iPSC technology and genetically normal Intestinal tissue or related cell types described herein. In some embodiments, intestinal tissue or related cell types described herein can be used to generate replacement tissue. Examples of genetic diseases include but are not limited to Neurog3 mutations and Enteric anendocrinosis, PTF1a mutations and neonatal diabetes, PDX1 mutations that effect enteroendocrine cells of the intestine.

In some embodiments, intestinal tissue or related cell types described herein can be used to generate replacement intestinal tissue for Inflamatory Bowel Disease (IBD), Crohn's Disease, Short Gut syndrome, intestinal cancer patients.

In some embodiments, intestinal tissue or related cell types described herein can be used to study microbiotic interactions with the human host epithelium and host immunity.

In some embodiments, intestinal tissue or related cell types described herein, in particular the enteroendocrine cells can be used to study hormonal regulation of feeding behavior, metabolism, mediated by intestinal endocrine hormones, for example the incretin response.

In some embodiments, intestinal tissue or related cell types described herein, in particular the enteroendocrine cells that produce the hormone GLP-1 can be used to study and improve pancreatic beta-cell mass and function and for treatment of diabetes.

In some embodiments, intestinal tissue or related cell types described herein can be used to replace any damaged or removed intestinal tissue such as that removed from colon cancer.

In some embodiments, intestinal tissue or related cell types described herein can be used to screen for toxicity and efficacy of any drug that acts on the intestine, for example, for diarrhea drugs, drugs that regulate secretion and absorption of the intestinal epithelium.

In some embodiments where intestinal tissue or related cell types described herein are used to determine the absorption level of a compound, the compound will be contacted with the intestinal cells or tissues with a compound; and a level of absorption of the compound by the intestinal cells or tissues detecting can be quantified. In some embodiments, the compound is labeled with a radio-isotope, a fluorescent label and or a primary or secondary visible marker.

In some embodiments, a diagnostic kit or package is developed to include the intestinal tissue or related cell types described herein and based on one or more of the aforementioned utilities.

Additional Embodiments Based on Microarray Analysis

In some embodiments, a reverse-engineering type of approach is taken to achieve directed differentiation of pluripotent stem cells. For example, microarray analyses of human ESCs, iPSCs and DE cultures, in both differentiated and undifferentiated states, are performed to identify cellular constituents that are differentially expressed in these different cell types. In some embodiments, only cellular constituents that are differentially expressed above a pre-determined level are identified as target cellular constituents. In particular, genes that are significantly differentially expressed are identified as targets. In some embodiments, significant differential expression occurs when a cellular constituent in a differentiated state in a particular cell type (e.g., as ESCs, iPSCs and DE) is expressed more than n folds than the expression level of the same cellular constituent in an undifferentiated state in the same cell type. In some embodiments, n is equal or greater than 2; equal or greater than 3; equal or greater than 5; equal or greater than 7; equal or greater than 10; equal or greater than 15; equal or greater than 18; equal or greater than 20; equal or greater than 23; or equal or greater than 28.

In some embodiments, selected cellular constituents from Table 2 are used as the target cellular constituents. For example, one or more cellular constituents that are differentially expressed above a pre-determined level are identified as target cellular constituents. In some embodiments, molecules capable of modulating the abundance levels of the target cellular constituents are used to treat cells at a certain development stage in order to achieve the desired directed differentiation results. In some embodiments, the target cellular constituents comprise 3 or more cellular constituents from Table 2; 5 or more cellular constituents from Table 2; 6 or more cellular constituents from Table 2; 8 or more cellular constituents from Table 2; 10 or more cellular constituents from Table 2; 12 or more cellular constituents from Table 2; 15 or more cellular constituents from Table 2; 18 or more cellular constituents from Table 2; 20 or more cellular constituents from Table 2; or 25 or more cellular constituents from Table 2.

Having described the invention in detail, it will be apparent that modifications, variations, and equivalent embodiments are possible without departing the scope of the invention defined in the appended claims. Furthermore, it should be appreciated that all examples in the present disclosure are provided as non-limiting examples.

EXAMPLES

The following non-limiting examples are provided to further illustrate embodiments of the invention disclosed herein. It should be appreciated by those of skill in the art that the techniques disclosed in the examples that follow represent approaches that have been found to function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

Example 1

Directing Hindgut Development of PSCs

Maintenance of PSCs.

Human embryonic stem cells and induced pluripotent stem cells were maintained on Matrigel (BD Biosciences) in mTesR1 media. Cells were passaged approximately every 5 days, depending on colony density. To passage PSCs, they were washed with DMEM/F12 media (no serum)(Invitrogen) and incubated in DMEM/F12 with 1 mg/mL dispase (Invitrogen) until colony edges started to detach from the dish. The dish was then washed 3 times with DMEM/F12 media. After the final wash, DMEM/F12 was replaced with mTesR1. Colonies were scraped off of the dish with a cell scraper and gently triturated into small clumps and passaged onto fresh Matrigel-coated plates.

Differentiation of PSCs into Definitive Endoderm (DE).

Differentiation into Definitive Endoderm was Carried Out as Previously Described.

Briefly, a 3 day ActivinA (R&D systems) differentiation protocol was used. Cells were treated with ActivinA (100 ng/ml) for three consecutive days in RPMI 1640 media (Invitrogen) with increasing concentrations of 0%, 0.2%, 2% HyClone defined FBS (dFBS) (Thermo Scientific).

Differentiation of DE in Permissive Media (Differentiation Protocol for FIG. 1).

After differentiation into definitive endoderm, cells were incubated in DMEM/F12 plus 2% defined fetal bovine serum (dFBS) with either 0, 50, or 500 ng/ml of FGF4 and/or 0, 50, or 500 ng/ml of Wnt3a (R&D Systems) for 6, 48, or 96 hours. Cultures were then grown in permissive media consisting of DMEM plus 10% fetal bovine serum (FBS) for an additional 7 days.

Directing Hindgut Development of PSCs.

Figure 1B:
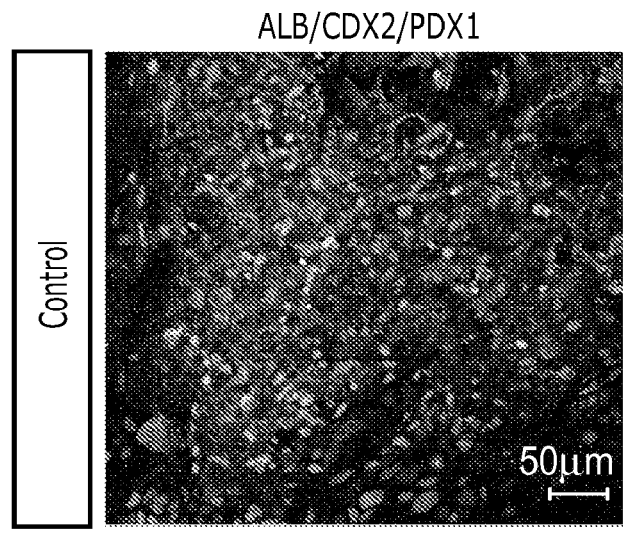
Figure 1C:
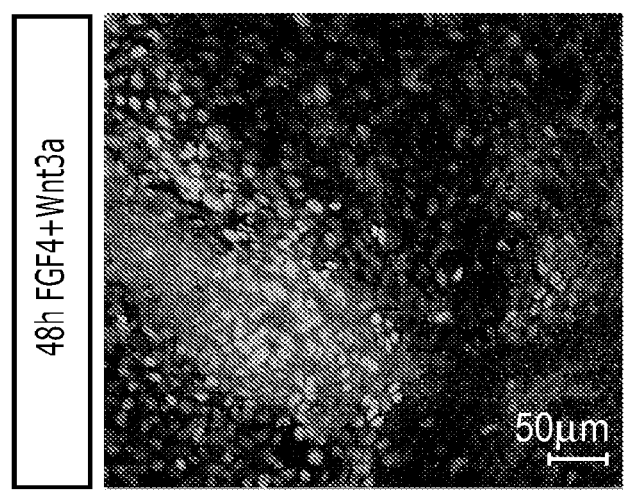
Figure 1D:
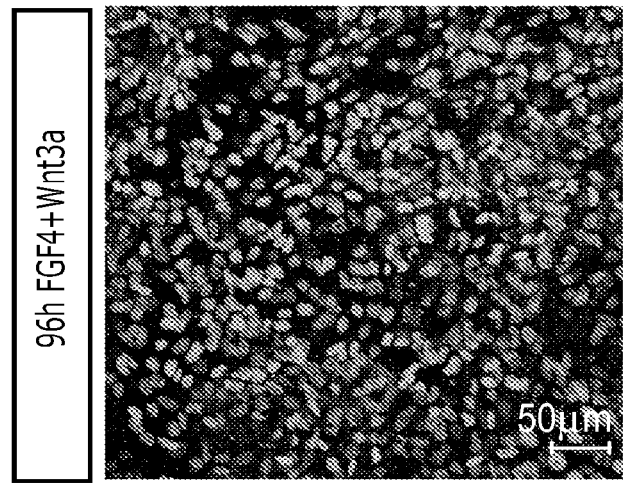
Figure 6A:
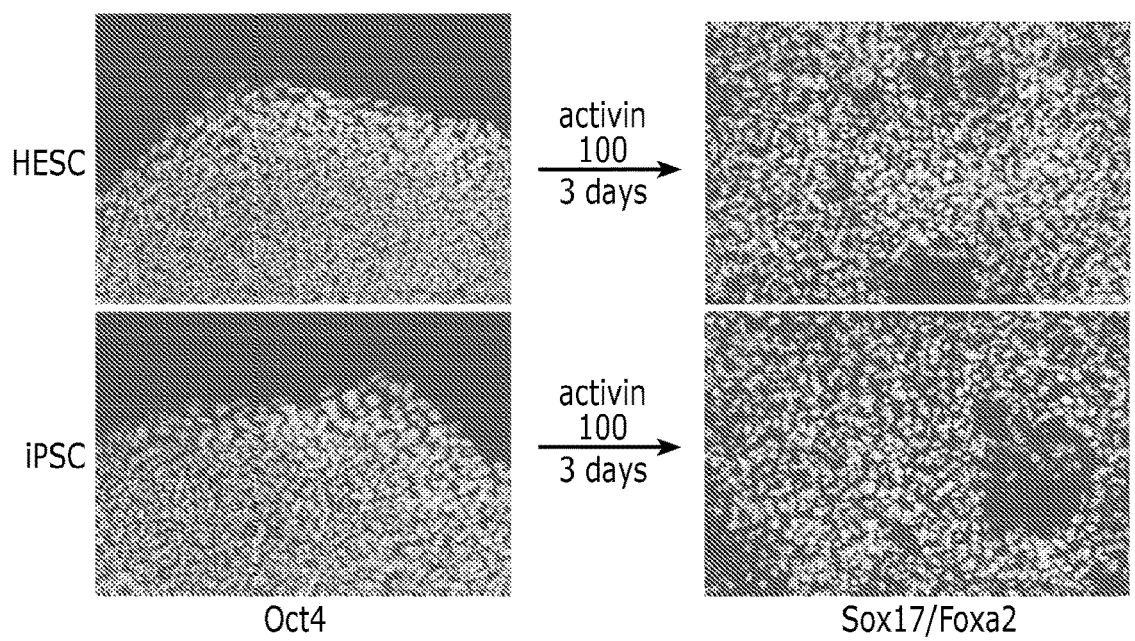
FIGS. 6A and 6B illustrate exemplary embodiments in accordance with the present invention.

As a first step to generating intestinal tissue, nodal-related TGFβ molecule activinA was used to promote differentiation of PSCs into DE as previously published. Activin-mediated differentiation routinely resulted in up to 90% of the cells co-expressing the DE markers SOX17 and FOXA2 (FIG. 6a). A robust activation of the DE transcriptional program (FIG. 6b and Table 2) was observed by using microarray analysis. It was also observed that cultures treated with activinA for only 3-days were competent to develop into both foregut (Albumin+ and Pdx1+) and hindgut (Cdx2) lineages when cultured for seven days in permissive conditions (FIG. 1b, control). In contrast, prolonged activin treatment for 4-5 days (common in many protocols) resulted in DE cultures that were intrinsically anterior in character and not as competent to form posterior lineages.

After the window of time when DE fate was plastic was identified, growth factors that are known to posteriorize endoderm, Wnt3a and FGF4, were used to direct the DE into a hindgut lineage. While neither factor alone was sufficient to robustly promote a posterior fate we determined that high concentrations of both FGF4+Wnt3a (500 ng/ml each) were able to induce robust expression of the hindgut marker CDX2 in the DE after 24-48 hours (FIG. 7). However 48 hours of FGF4+Wnt3a treatment was not sufficient to induce stable posterior, hindgut identity since CDX2 expression was not maintained and anterior fates, as measured by Pdx1 and Albumin expression, persisted following growth factor removal (FIGS. 1a, c). In contrast, 96 hours of exposure to FGF4+Wnt3a conferred a stable posterior endoderm phenotype following growth factor removal with maintained CDX2 expression and complete absence of anterior markers (FIGS. 1a and d). Thus prolonged activity of FGF4 and Wnt3a resulted in a robust posteriorization of DE into CDX2+hindgut endoderm.

Figure 2A:
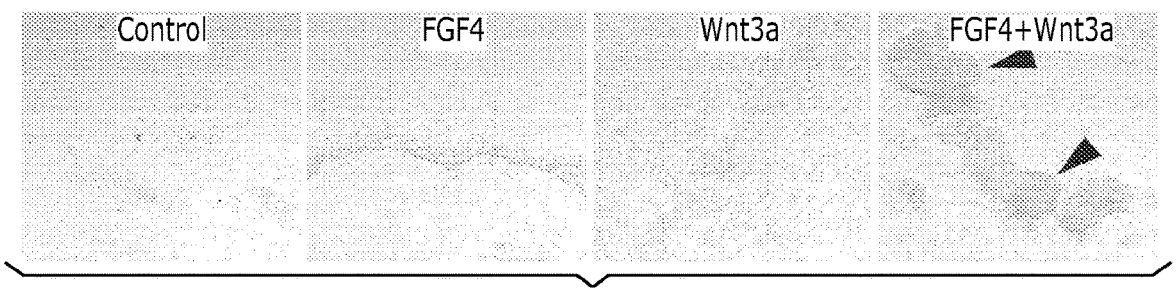
FIGS. 2A-2H illustrate exemplary embodiments in accordance with the present invention.
Figure 2B:
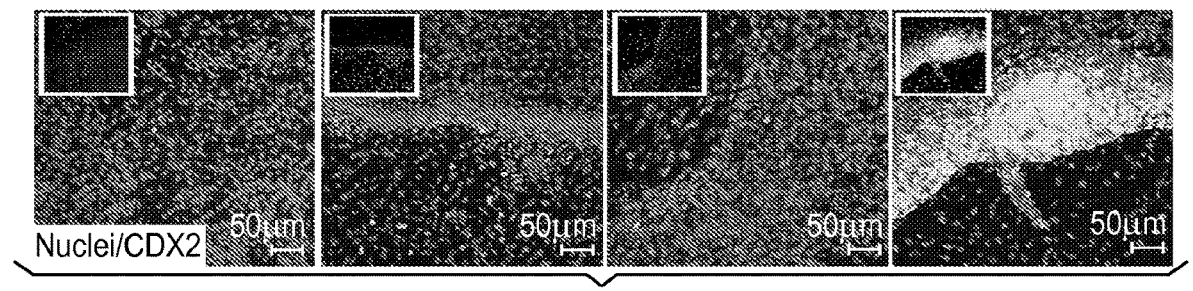
Figure 2C:
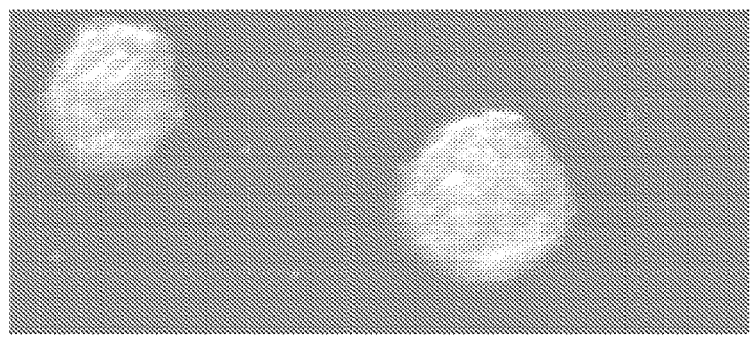
Figure 2D:
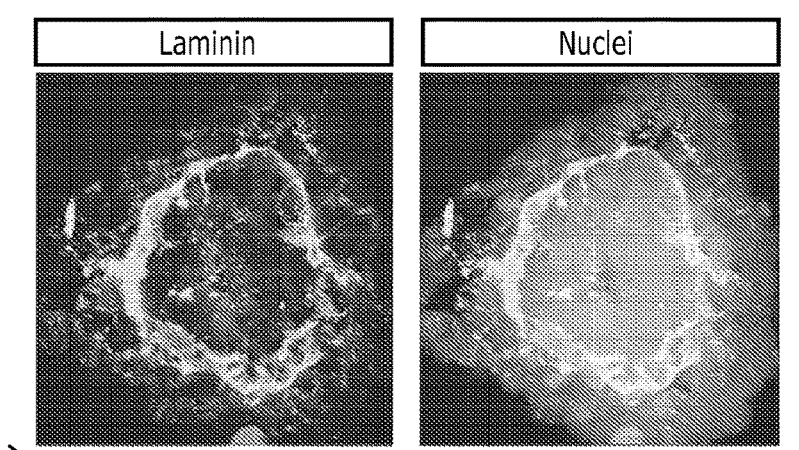
Figure 2E:
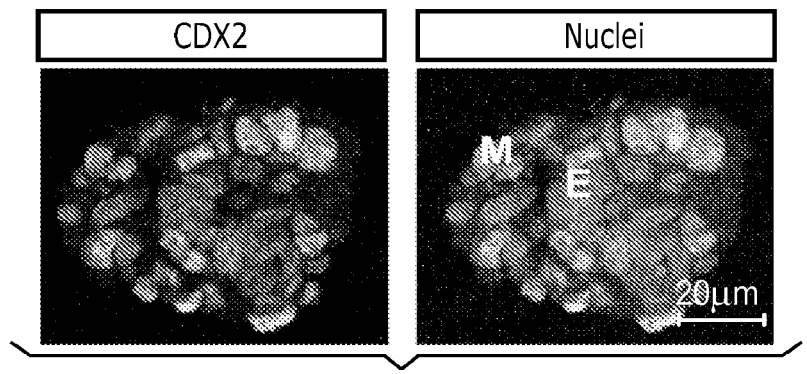
Figure 2F:
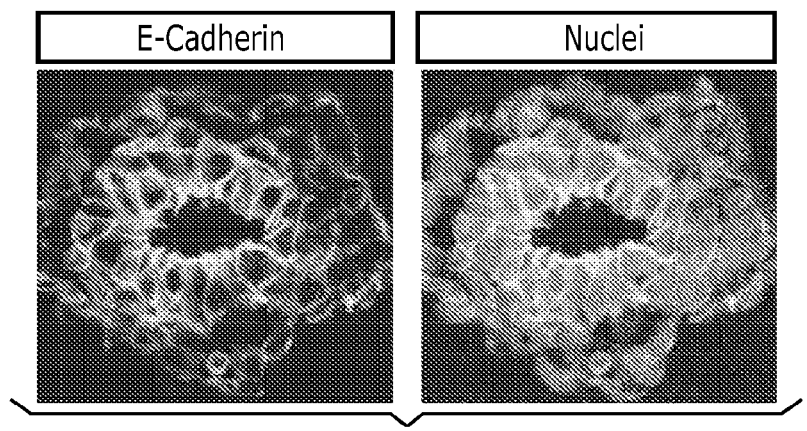
Figure 2G:
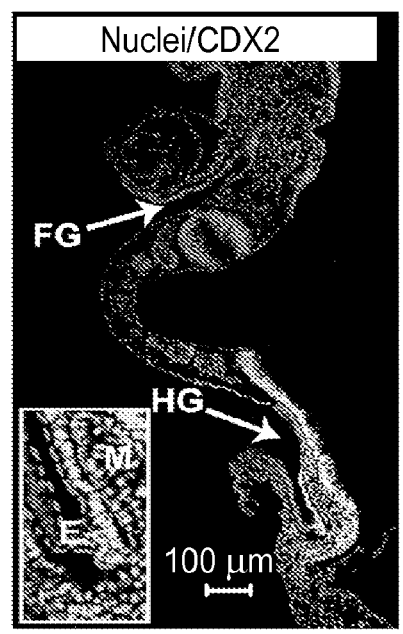
Figure 2H:
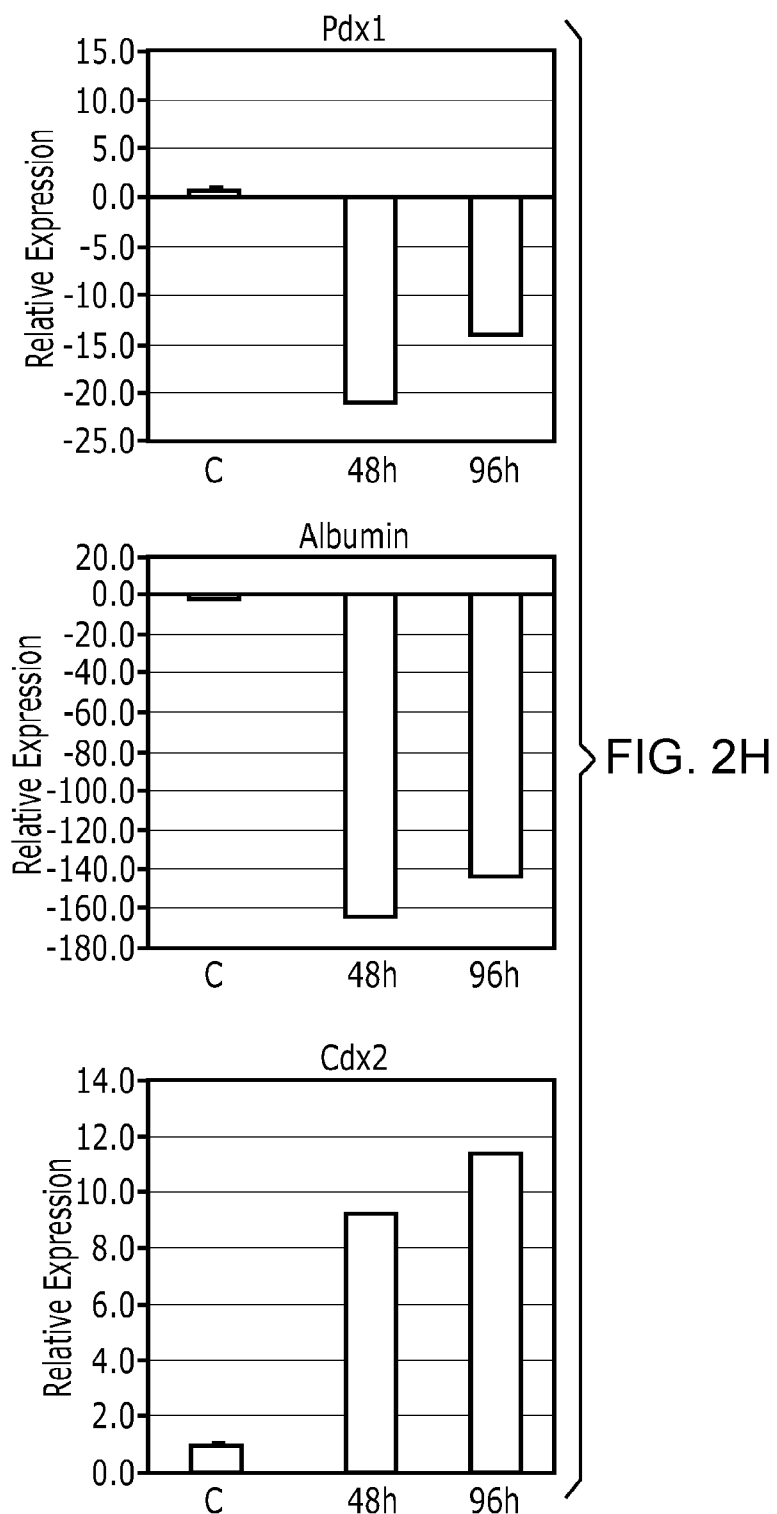

Not only were the molecular features of hindgut formation in vitro similar to hindgut development in vivo, FGF4+Wnt3a treated cultures underwent a morphogenesis similar to embryonic gut tube formation. Between 2 and 5 days of FGF4+Wnt3a treatment, flat cell sheets condensed into CDX2+ epithelial tubes, many of which budded off to form floating hindgut spheroids (FIG. 2a-c, FIG. 10a-10f) (Table 2a). Spheroids (FIG. 2c-f) were similar to e8.5 mouse hindgut (FIG. 2g) containing CDX2+ polarized epithelium (E) surrounded by CDX2+ mesenchyme (M). Spheroids were completely devoid of Alb- and Pdx1-expressing foregut cells (FIG. 2h). This in vitro gut-tube morphogenesis was never observed in control or Wnt3a-only treated cultures and FGF4 treated cultures generated 4-10 fold fewer spheroids (Table 1A), which were weakly CDX2+ and did not undergo further expansion. The similarity of the hindgut spheroids to mouse embryonic hindgut suggests that the morphological differentiation induced by FGF4+Wnt3 is a key event in the specification of the intestinal lineage.

The following tables illustrate the effects of growth factor treatment of hESCs and iPSCs. Generation of hindgut spheroids was tracked for (Table 1A) days 2-5 following growth factor treatment for H9 hESCs or (Table 1B) days 2-4 of growth factor treatment for iPSCs. Definitive endoderm was treated with either 500 ng/ml of FGF4 alone or 500 ng/ml of FGF4+Wnt3a. For both HESCs and iPSCs, hindgut spheroids formed much more robustly under FGF4+Wnt3a conditions. Control cultures or ones treated with Wnt3a alone never formed spheroids. Over the course of 4 days, FGF4+Wnt3a treated H9 endoderm generated an average of 4.5 fold more spheroids than that treated with FGF4 alone. Similarly, FGF4+Wnt3a treated iPSC endoderm generated an average of 7.25 fold more spheroids than that treated with FGF4 alone.

TABLE 1A

Growth factor treatment of hESCs: frequency of spheroid formation from hESC-H9.

| Days of GF treatment (H9 hESCs) | Total # organoids FGF4 treated (# organoids/ wells counted) | Average # organoids per well FGF4 treated | Total # organoids FGF4 + Wnt3a treated (# organoids/wells counted) | Average # organoids per well FGF4 + Wnt3a treated |
|---|---|---|---|---|
| 2 days (48 h) | 0/5 | 0 | 10/10 | 1 |
| 3 days (72 h) | 0/5 | 0 | 150/10 | 15 |
| 4 days (96 h) | 44/5 | 8.8 | 322/10 | 32.2 |
| 5 days (120 h) | 19/4 | 4.75 | 100/8 | 12.5 |

TABLE 1B

Growth factor treatment of iPSCs: frequency of spheroid formation from iPSC-3.5.

| Days of GF treatment (iPSCs) | Total # organoids FGF4 treated (# organoids/ wells counted) | Average # organoids per well FGF4 treated | Total # organoids FGF4 + Wnt3a treated (# organoids/wells counted) | Average # organoids per well FGF4 + Wnt3a treated |
|---|---|---|---|---|
| 2 days (48 h) | 0/4 | 0 | 0/10 | 0 |
| 3 days (72 h) | 10/4 | 2.5 | 229/10 | 22.9 |
| 4 days (96 h) | 14/4 | 3.5 | 206/10 | 20.6 |

Frequencies of spheroid formation in response to FGF4 and Wnt3a were studied, as shown in Tables 1A and 1B. Generation of hindgut spheroids was tracked for days 2-5 of growth factor treatment (H9 hESCs, Table 1A) or days 2-4 of growth factor treatment (iPSCs, Table 1B) for endoderm being given either 500 ng/ml FGF4 alone or 500 ng/ml FGF4+Wnt3a. In both cell lines, hindgut spheroids were much more robustly generated in FGF4+Wnt3a conditions. Over the course of 4 days, FGF4+Wnt3a treated H9 endoderm generated an average of 4.5 fold more spheroids than FGF4 treated alone. Similarly, FGF4+Wnt3a treated iPSC endoderm generated an average of 7.25 fold more spheroids than FGF4 treated alone.

Not only were the molecular features of hindgut formation in vitro similar to hindgut development in vivo, FGF4+Wnt3a treated cultures underwent a morphogenesis similar to embryonic gut tube formation. Between 2 and 5 days of FGF4+Wnt3a treatment, flat cell sheets condensed into CDX2+ epithelial tubes, many of which budded off to form floating hindgut spheroids (FIG. 2a-c, FIG. 10a-f) (table 1A). Spheroids (FIG. 2c-f) were similar to e8.5 mouse hindgut (FIG. 2g) containing CDX2+ polarized epithelium (E) surrounded by CDX2+ mesenchyme (M). Spheroids were completely devoid of Alb- and Pdx1-expressing foregut cells (FIG. 2h). This in vitro gut-tube morphogenesis was not observed in control or Wnt3a-only treated cultures and FGF4 treated cultures generated 4-10 fold fewer spheroids (Table 1A), which were weakly CDX2+ and did not undergo further expansion (not shown). The similarity of the hindgut spheroids to mouse embryonic hindgut suggests that the morphological differentiation induced by FGF4+Wnt3 is a key event in the specification of the intestinal lineage.

More details can be found in, for example, D'Amour, K. A., et al. Efficient differentiation of human embryonic stem cells to definitive endoderm. *Nat Biotechnol* 23, 1534-1541 (2005); Beck, F., Erler, T., Russell, A. & James, R. Expression of Cdx-2 in the mouse embryo and placenta: possible role in patterning of the extra-embryonic membranes. *Dev Dyn* 204, 219-227 (1995); Dessimoz, J., Opoka, R., Kordich, J. J., Grapin-Botton, A. & Wells, J. M. FGF signaling is necessary for establishing gut tube domains along the anterior-posterior axis in vivo. *Mech Dev* 123, 42-55 (2006); McLin, V. A., Rankin, S. A. & Zorn, A. M. Repression of Wnt/{beta}-catenin signaling in the anterior endoderm is essential for liver and pancreas development. *Development* 134, 2207-2217 (2007); Wells, J. M. & Melton, D. A. Early mouse endoderm is patterned by soluble factors from adjacent germ layers. *Development* 127, 1563-1572. (2000); each of which is incorporated herein in its entirety.

FIGS. 1a through 1d illustrate exemplary embodiments of the present invention. FGF4 and Wnt3a act synergistically in a temporal and dose-dependent manner to specify stable posterior endoderm fate. ActivinA (100 ng/ml) was used to differentiate H9-HES cells into definitive endoderm (DE). DE was treated with the posteriorizing factors FGF4 (50, 500 ng), Wnt3a (50, 500 ng) or both for 6, 48 or 96 hours. Cells were then cultured in a permissive medium without growth factors for an additional seven days and analyzed for expression of foregut markers (ALB, PDX1) and the hindgut marker (CDX2) by RT-qPCR (a) and immunofluorescence (b-d). FGF4/Wnt-mediated changes in marker expression in (a) is relative to 3-day activin treated DE cultures that were grown for identical lengths of time in the absence of FGF4 or Wnt3a (control). Only high levels of FGF4+Wnt3a for 96 hours gave cultures with stable CDX2 expression that lack foregut marker expression. Error bars denote standard deviation of triplicates. Significance is shown by; * ($p<0.05$), ^ ($p<0.001$), # ($p<0.0001$).

FIGS. 2a through 2h illustrate exemplary embodiments in accordance with the present invention in which posterior endoderm is shown developing into 3-dimensional, hindgut-like organoids. Morphogenesis of posterior endoderm into three-dimensional, hindgut-like organoids is depicted. (a) Bright field images of DE that was treated with FGF4+Wnt3a 96 hours formed numerous 3D epithelial structures including tubes and free-floating spheres (black arrows) relative to control DE, Wnt3a or FGF4 cultures (see Table 1A and 1B). (b) CDX2 immunostaining (Green) and nuclear stain (Drags—blue) on cultures shown in (a). 3D structures in FGF4+Wnt3a treated cultures were largely CDX2 positive. Insets—green channel only showing CDX2 staining. (c) Bright field image of hindgut-like spheroids. (d-f) Analysis of CDX2, basal-lateral lamina and E-Cadherin expression demonstrate that spheroids contain an inner layer of polarized, cuboidal, CDX2 positive epithelium surrounded by non-polarized mesenchyme-like CDX2 cells. (g) CDX2 expression in an e8.5 mouse embryo (sagittal section) shows that both hindgut endoderm (E) and adjacent mesenchyme (M) are CDX2 positive (green), similar to hindgut spheroids (Inset shows a magnified view of CDX2 staining in the hindgut endoderm and mesoderm; FIG—foregut, HG—hindgut. (h) RT-qPCR analysis of hindgut-like spheroids did not detect foregut markers (PDX1, Albumin) but detected robust expression of hindgut markers (CDX2). Expression levels shown in (h) is relative to 3-day activin treated DE cultures that were grown for identical lengths of time in the absence of FGF4 or Wnt3a (C=control; 48h=spheroids generated after 48 hours; 96h=spheroids generated after 96 hours). Error bars denote standard deviation of triplicates.

Figure 7A:
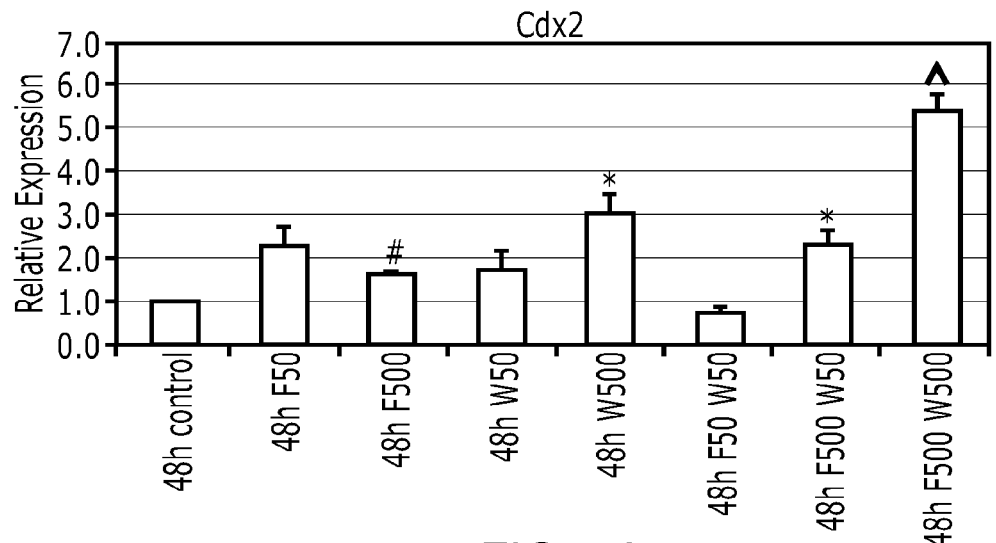
Figure 7B:
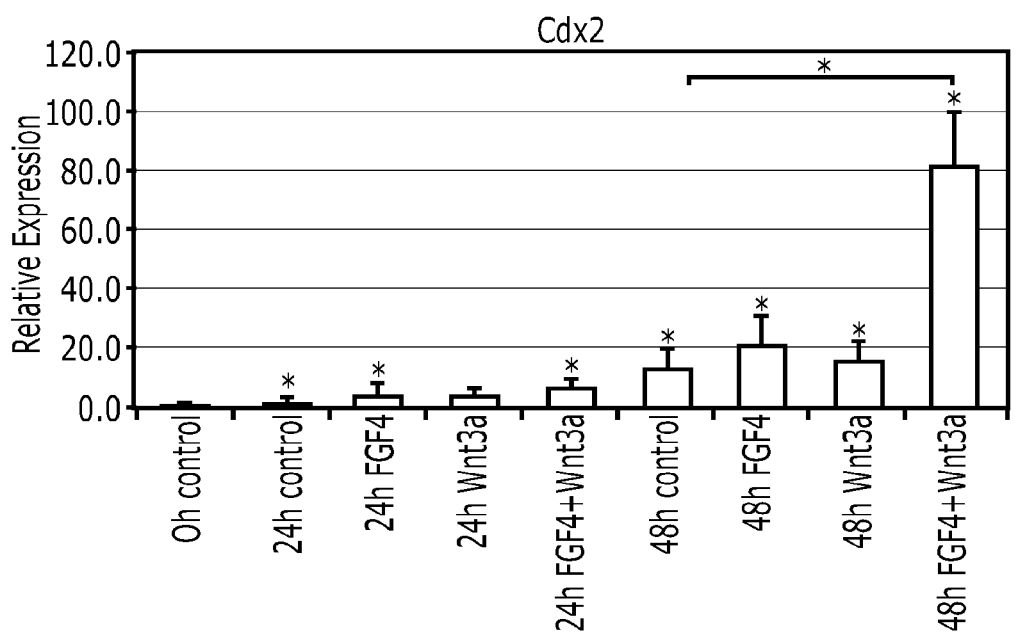

FIGS. 7a and 7b illustrate exemplary embodiments in accordance with the present invention, depicting time and concentration dependent induction of CDX2 by FGF4 and Wnt3a. (a) FGF4 and Wnt3a up-regulate CDX2 in a concentration dependant manner. 3-day ActivinA treated hESCs were treated for 48 hours with Wnt3a at 50 ng/ml or 500 ng/ml or FGF4 at 50 ng/ml or 500 ng/ml, or increasing concentrations of FGF4+Wnt3a. Cells were analyzed after 48 hours of treatment. FGF4 or Wnt3a alone caused modest changes in CDX2 expression at different doses. FGF4+Wnt3a at the highest dose (500 ng/ml each) induced robust CDX2 expression. CDX2 expression was normalized to the internal control beta-tubulin, and is shown relative to a 48 hour control cultured in the absence of growth factors. (b) FGF4 and Wnt3a up-regulate CDX2 in a time dependant manner. 48 hours of exposure to FGF4+Wnt3a was required for the most robust induction of CDX2. All time points shown are set relative to a 0 hour no growth factor control. 500 ng/ml of FGF4, Wnt3a or FGF4+Wnt3a was used for all time points. Note that 24 hour and 48 controls, in the absence of growth factors, show a significant and spontaneous up-regulation of CDX2. Error bars denote standard deviation of triplicates. Significance is shown by; * ($p<0.05$)

Example 2

Directing Hindgut Spheroids into Intestinal Tissue In Vitro

Directed Differentiation into Hindgut and Intestinal Organoids.

After differentiation into definitive endoderm, cells were incubated in 2% dFBS-DMEM/F12 with either 50 or 500 ng/ml FGF4 and/or 50 or 500 ng/ml Wnt3a (R&D Systems) for 2-4 days. After 2 days with treatment of growth factors, 3-dimensional floating spheroids were present in the culture. 3-dimensional spheroids were transferred into an in vitro system previously described to support intestinal growth and differentiation. Briefly, spheroids were embedded in Matrigel (BD Bioscience #356237) containing 500 ng/ml R-Spondin1 (R&D Systems), 100 ng/ml Noggin (R&D Systems) and 50 ng/ml EGF (R&D Systems). After the Matrigel solidified, media (Advanced DMEM/F12 (Invitrogen) supplemented with L-Glutamine, 10 µM Hepes, N2 supplement (R&D Systems), B27 supplement (Invitrogen), and Pen/Strep containing growth factors was overlaid and replaced every 4 days.

Directing Hindgut Spheroids into Intestinal Tissue In Vitro.

Figure 3A:
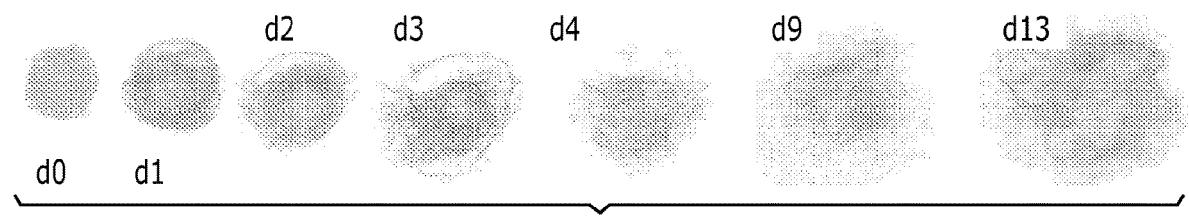
FIGS. 3A-3J illustrate exemplary embodiments in accordance with the present invention.
Figure 3B:
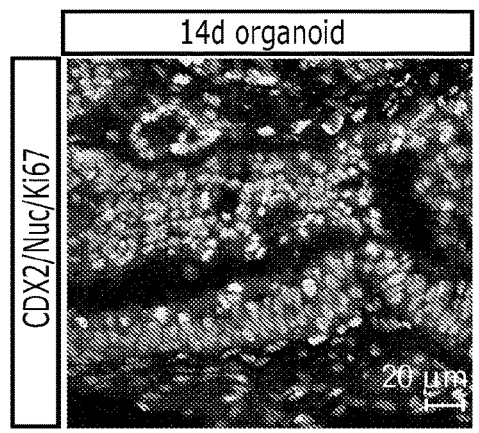
Figure 3C:
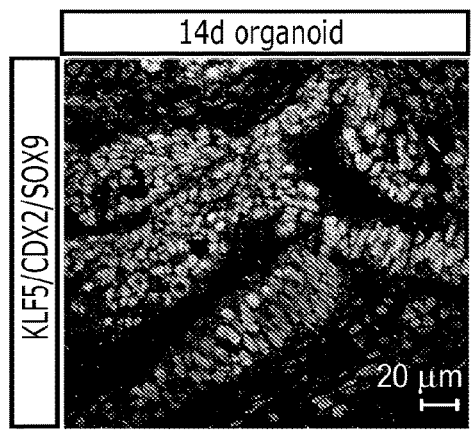
Figure 3D:
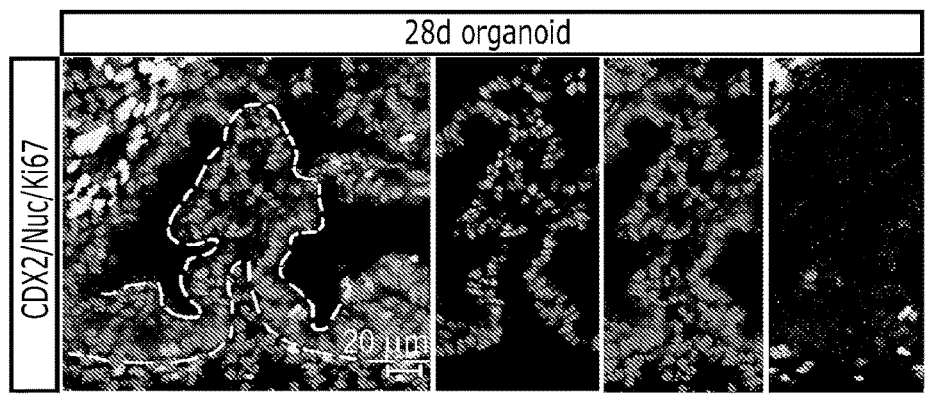
Figure 3E:
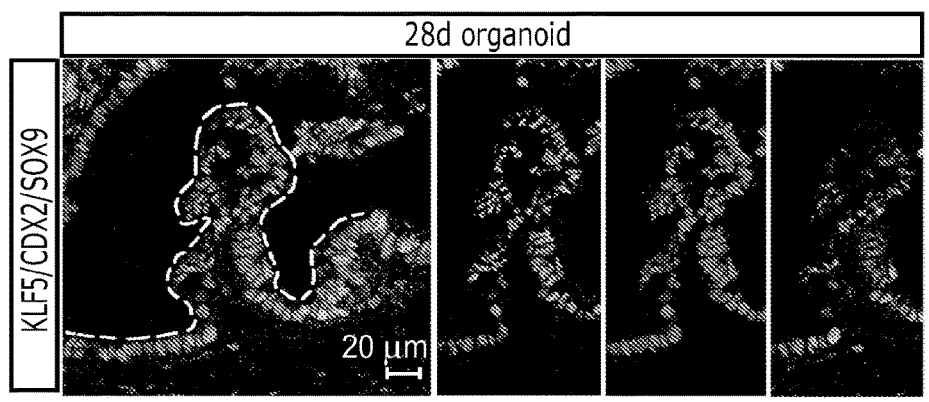
Figure 3F:
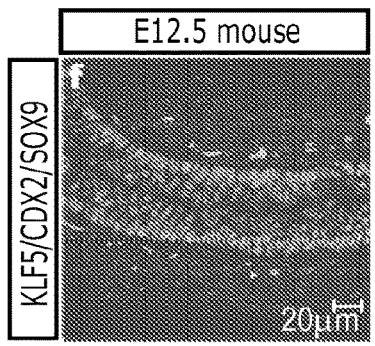
Figure 3G:
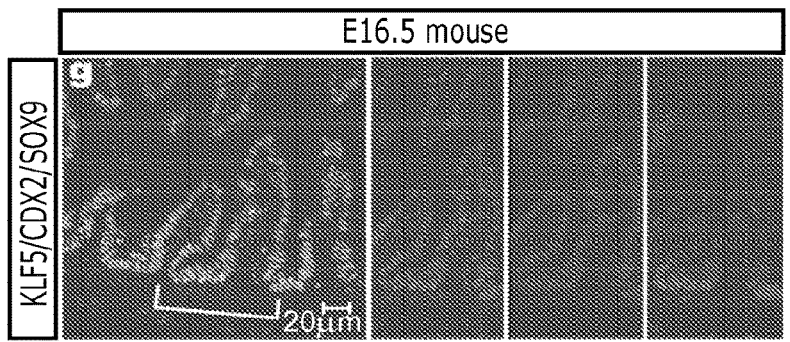
Figure 3H:
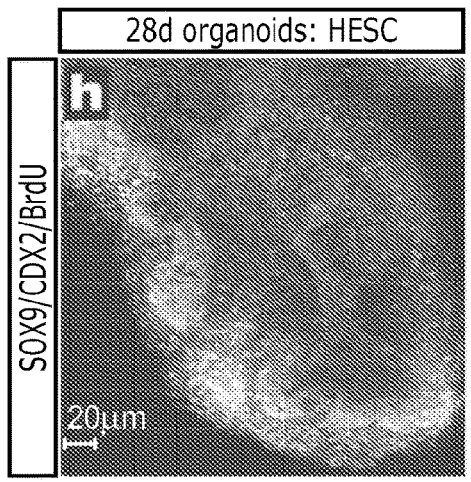
Figure 8:
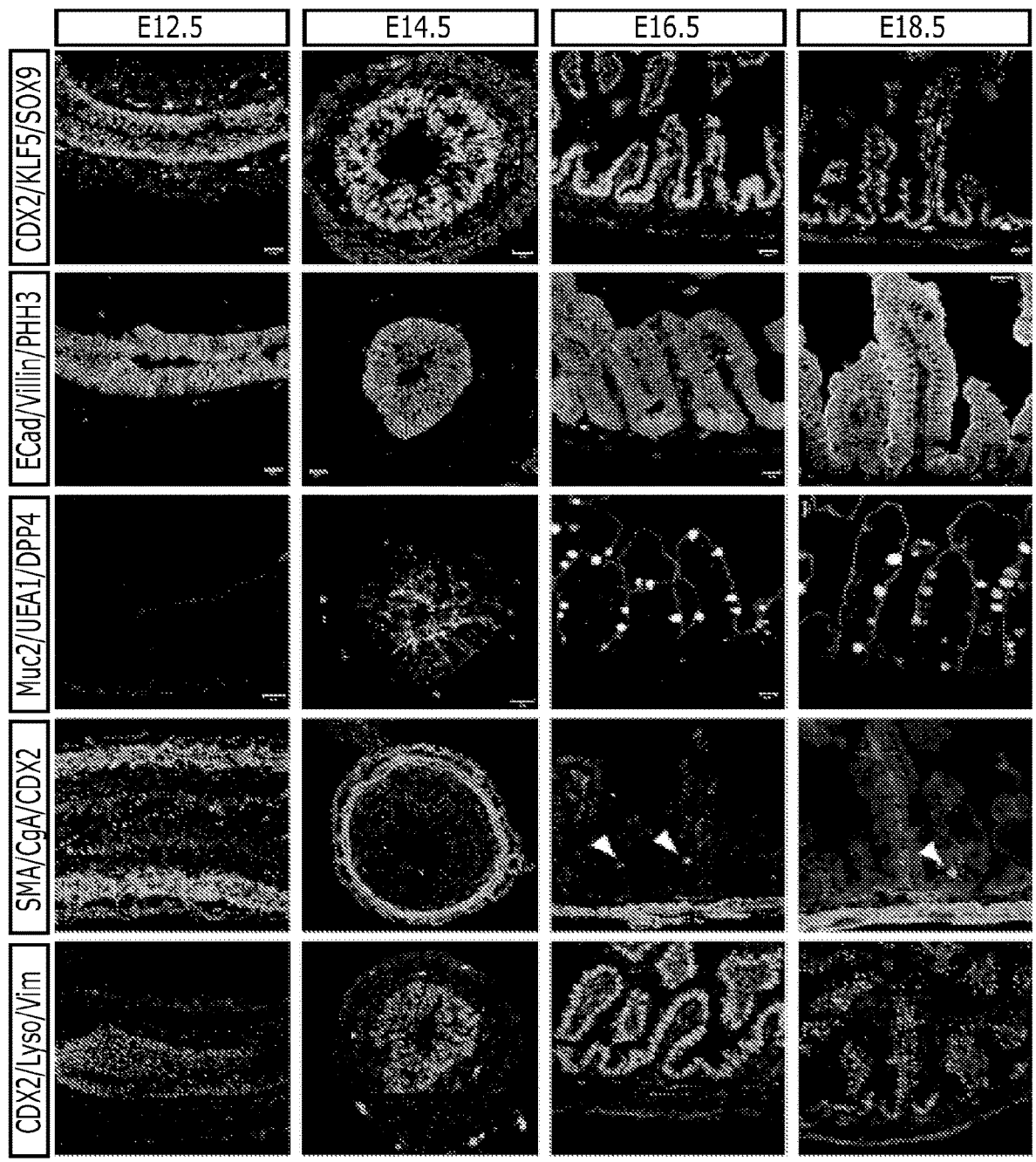
FIG. 8 includes immunofluorescent images illustrating exemplary embodiments in accordance with the present invention. The images depict molecular marker expression during mouse intestinal development at embryonic stages include e12.5, e14.5, e16.5 and e18.5.

While in vivo engraftment of PSC-derived cell types, such as pancreatic endocrine cells, has been used to promote maturation, maturation in vivo is a poorly defined process and is experimentally intractable. Primitive hindgut spheroids were sjpwm matured into intestine in vitro using the recently described 3-dimensional culture conditions that support growth and renewal of the adult intestinal epithelia. When placed into this culture system, hindgut spheroids developed into intestinal organoids in a staged manner that was strikingly similar to fetal gut development (FIG. 3 and FIG. 8). In the first 14 days the simple cuboidal epithelium of the spheroid expanded and formed a highly convoluted pseudostratified epithelium surrounded by mesenchymal cells (FIG. 3a-c). After 28 days, the epithelium matured into a columnar epithelium with villus-like involutions that protrude into the lumen of the organoid (FIG. 3d, e). Comparable transitions were observed during mouse fetal intestinal development (FIG. 3f, g and FIG. 8). The spheroids expanded up to 40 fold in mass as they formed organoids (data not shown). Moreover, 28-day organoids were split and passaged up to 5 additional times and cultured for over 100 days. The cellular gain during that time was up to 1,000 fold (data not shown), resulting in a total cellular expansion of 40,000 fold per hindgut spheroid.

Figure 3I:
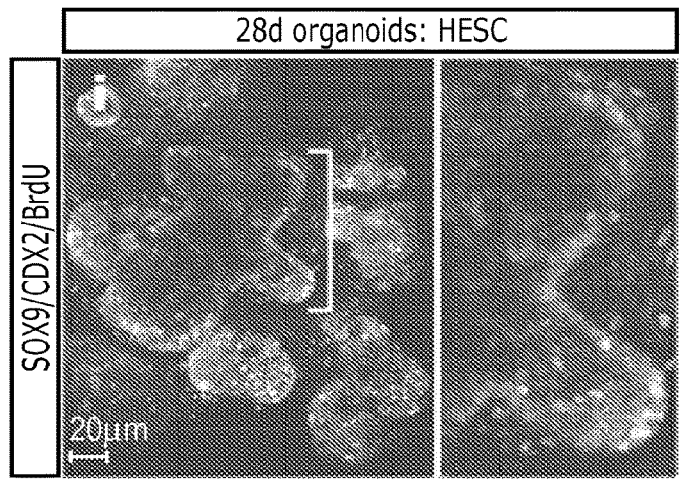
Figure 3J:
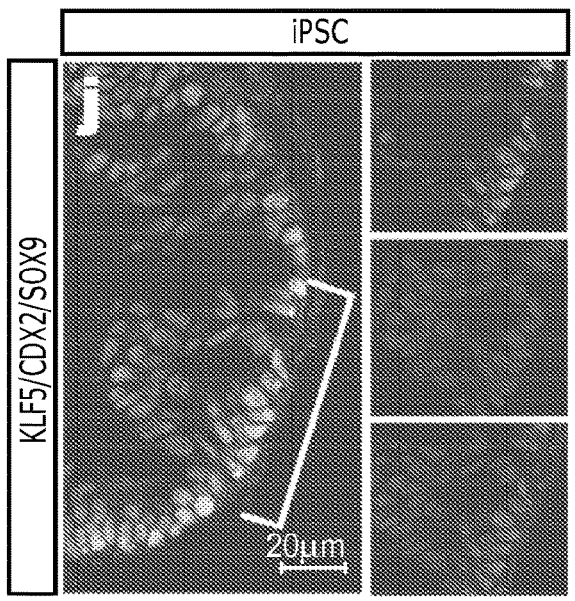
Figure 4A:
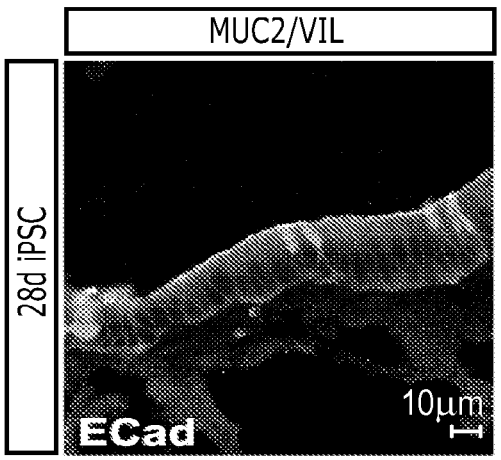
FIGS. 4A-4F illustrate exemplary embodiments in accordance with the present invention.
Figure 4A:
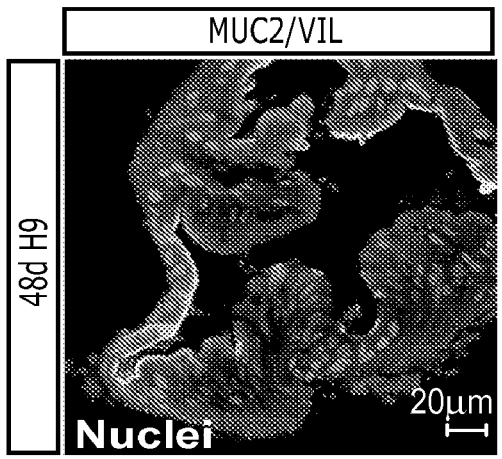
Figure 4B:
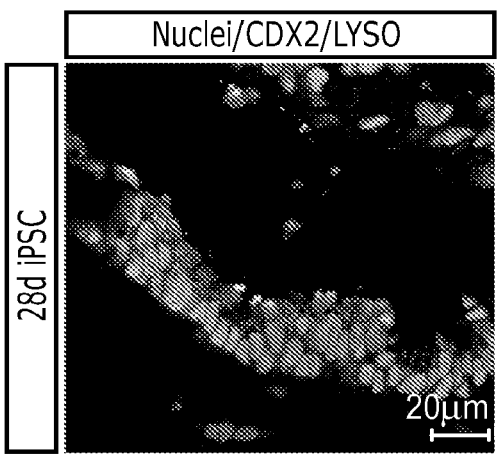
Figure 4B:
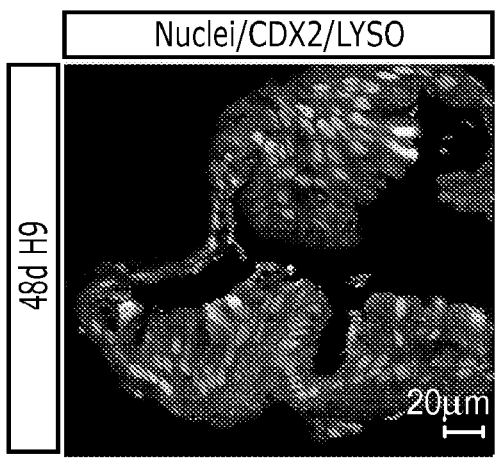
Figure 4C:
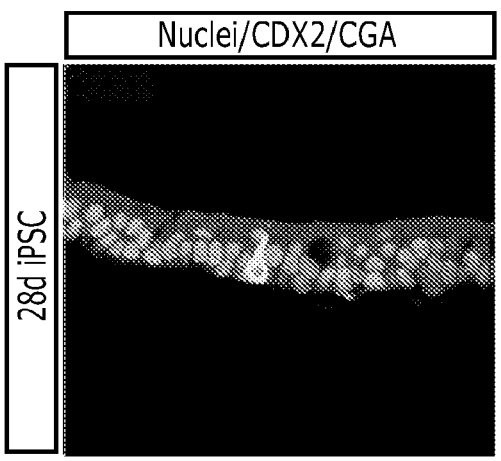
Figure 4C:
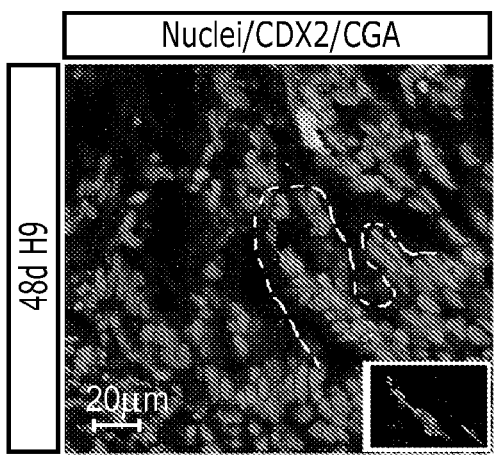
Figure 4D:
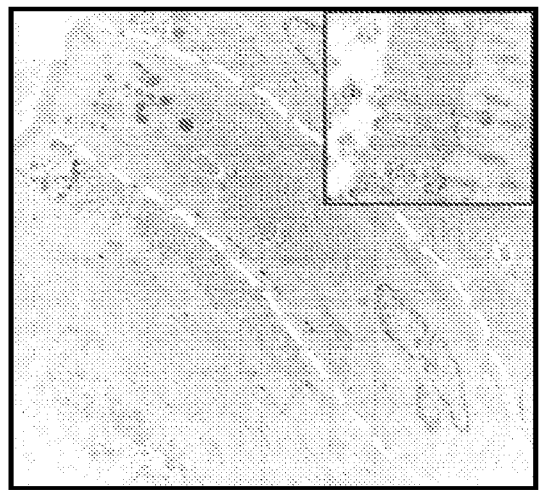
Figure 4E:
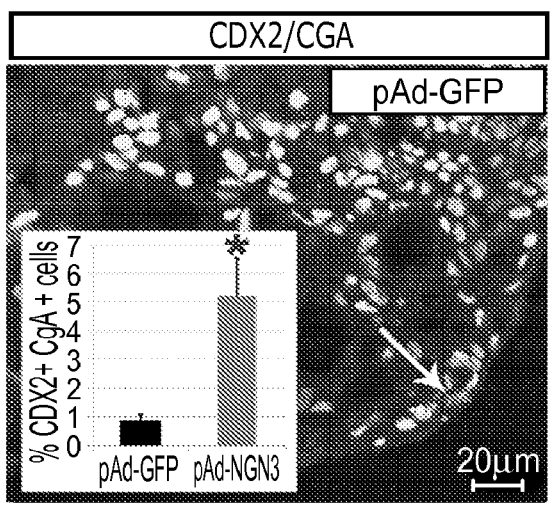
Figure 4F:
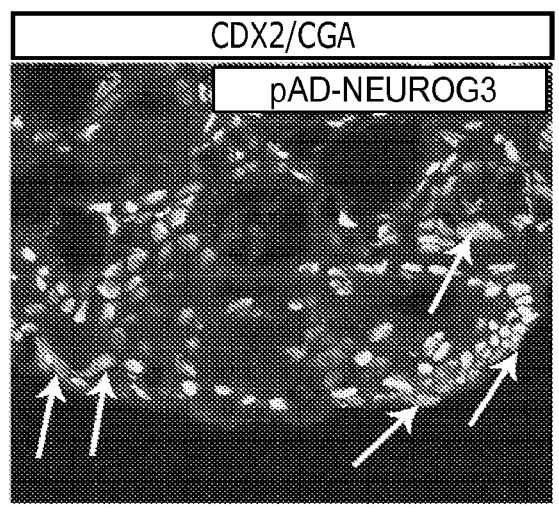

Marker analysis showed that after 14 days in culture, virtually all of the epithelium expressed the intestinal transcription factors CDX2, KLF5 and SOX9 broadly and was highly proliferative (FIG. 3b, c). By 28 days CDX2 and KLF5 remained broadly expressed, while SOX9 became localized to pockets of proliferating cells at the base of the villus-like protrusions (FIGS. 3d, e, h, i). Three-dimensional rendering of a series of confocal microscopic images further revealed that the proliferative zone was in a crypt-like structure that penetrated into the underlying mesenchyme (FIG. 3 h, i). The dynamic spatial expression of CDX2, KLF5 and SOX9 in maturing, 14-28 day intestinal organoids was similar to that of the developing fetal mouse intestines between e12.5 and e16.5 (FIG. 3i, j and FIG. 8). In particular, the restriction of SOX9 to the inter-villus proliferative zone is characteristic of the developing progenitor domain, which ultimately gives rise to the intestinal stem cell niche in the crypt of Lieberkühn.

Importantly, this method for directed differentiation into intestine should be broadly applicable to other PSC lines as intestinal tissues were generated from 2 hESC and 6 iPSC lines. The kinetics of differentiation and the formation of a patterned intestinal epithelium were indistinguishable between iPSCs and hESCs (FIG. 3j, FIGS. 6, 9, 10 and Table 1B). Additional data for information on generating and analyzing iPSC lines and for DNA microarray data comparing differentiation between H9 and iPSC lines can be found in Table 2.

Maintenance and directed differentiation of human ESCs and iPSCs into intestinal tissue. Human embryonic stem cells and induced pluripotent stem cells were maintained on Matrigel (BD Biosciences) in mTesR1 media without feeders. Differentiation into Definitive Endoderm was carried out as previously described. Briefly, a 3 day ActivinA (R&D systems) differentiation protocol was used. Cells were treated with ActivinA (100 ng/ml) for three consecutive days in RPMI 1640 media (Invitrogen) with increasing concentrations of 0%, 0.2%, 2% HyClone defined FBS (dFBS) (Thermo Scientific). For hindgut differentiation, DE cells were incubated in 2% dFBS-DMEM/F12 with 500 ng/ml FGF4 and 500 ng/ml Wnt3a (R&D Systems) for 2-4 days. After 2 days with treatment of growth factors, 3-dimensional floating spheroids were present and then transferred into three-dimensional cultures previously shown to promote intestinal growth and differentiation. Briefly, spheroids were embedded in Matrigel (BD Bioscience) containing 500 ng/mL R-Spondin1 (R&D Systems), 100 ng/ml Noggin (R&D Systems) and 50 ng/ml EGF (R&D Systems). After the Matrigel solidified, media (Advanced DMEM/F12 (Invitrogen) supplemented with L-Glutamine, 10 µM Hepes, N2 supplement (R&D Systems), B27 supplement (Invitrogen), and Pen/Strep containing growth factors was overlaid and replaced every 4 days.

More details can be found in, for example, Gracz, A. D., Ramalingam, S. & Magness, S. T. Sox9-Expression Marks a Subset of CD24-expressing Small Intestine Epithelial Stem Cells that Form Organoids in vitro. *Am J Physiol Gastrointest Liver Physiol* 298, G590-600 (2010); Sato, T., et al. Single Lgr5 stem cells build crypt-villus structures in vitro without a mesenchymal niche. *Nature* 459, 262-265 (2009); Kroon, E., et al. Pancreatic endoderm derived from human embryonic stem cells generates glucose-responsive insulin-secreting cells in vivo. *Nat Biotechnol* (2008); Ludwig, T. E., et al. Feeder-independent culture of human embryonic stem cells. *Nat Methods* 3, 637-646 (2006); Ludwig, T. E., et al. Derivation of human embryonic stem cells in defined conditions. *Nat Biotechnol* 24, 185-187 (2006); D'Amour, K. A., et al. Efficient differentiation of human embryonic stem cells to definitive endoderm. *Nat Biotechnol* 23, 1534-1541 (2005); each of which is incorporated herein in its entirety.

FIGS. 3a through 3j illustrate exemplary embodiments in accordance with the present invention, showing the formation of intestine-like organoids from hESCs and hiPSCs. a, Time course of organoid growth for 13 days. (a) Organoids underwent epithelial growth and budding, forming highly convoluted epithelial structures by day 9. (b-e) Analysis of characteristic intestinal transcription factor expression (KLF5, CDX2, SOX9) and cell proliferation on serial sections of organoids after 14 and 28 days of culture (serial sections are b and c, d and e). (f) and (g) Expression of KLF5, CDX2, and SOX9 in mouse fetal intestine at e14.5 (f) and e16.5 (g) is similar to developing intestinal organoids. (h) and (i), whole mount immunofluorescence z-stacks of two different organoids for BrDU, CDX2, and SOX9 showing proliferative zones in crypt-like structures associated with the mesenchyme. (j) human iPSCs derived from keratinocytes form intestinal organoids in an identical manner to hESCs as measured by KLF5, CDX2, and localized SOX9 expression. The insets to the right in (d), (e), (g) and (j) show separated color channels.

Figure 6B:
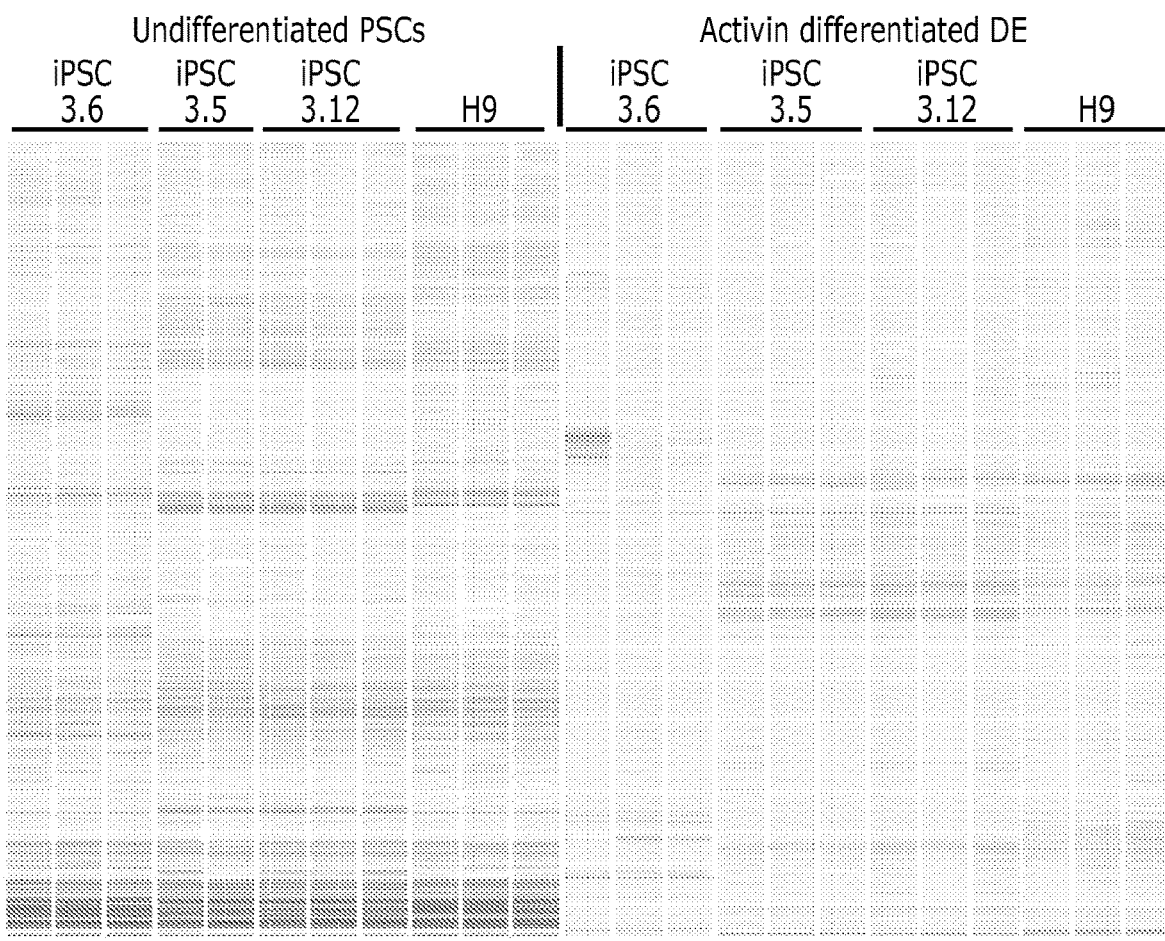

FIGS. 6a and 6b illustrate exemplary embodiments in accordance with the present invention, depicting characterization of DE formation from hESC and iPSC lines by immuno-fluorescence (IF) and Microarray analysis. (a) Undifferentiated hESCs stained with the pluripotency marker OCT4 (green) were treated for 3 days with ActivinA. This DE induction protocol routinely results in 80-90% SOX17 (green)/FOXA2 (red) double positive cells in both hESCs and iPSCs. (b) Transcriptional profile of DE induction. hESC-H9 and iPSC lines 3.5, 3.6 and 3.12 were analyzed before and after DE formation (activin differentiation) by Affymetrix DNA microarray analysis. Clustering analysis of transcripts that were differentially regulated during DE formation indicated that iPSC lines 3.5 and 3.12 differentiate in manner that is highly similar to hESC-H9 cells (see Tables 1A and 1B for gene list and fold expression changes). iPSC line 3.6 had a more divergent transcriptional profile and was therefore not used for subsequent experiments.

FIG. 8 illustrates exemplary embodiments in accordance with the present invention, depicting molecular marker expression during mouse intestinal development. Embryonic stages include e12.5, e14.5, e16.5 and e18.5. Transcription factors detected were CDX2, KLF5, and SOX9. Epithelial markers used were E-cadherin (Ecad), Villin and DPP4. Vimentin (Vim) and Smooth Muscle Actin (SMA) were used as mesenchymal markers. Differentiation markers used were Lysozyme (Lyso) for paneth cells, Mucin (Muc2) and UEA-1 for goblet cells, Chromogranin A (CgA) for enteroendocrine cells. Phosphohistone H3 (PHH3) shows mitotic cells.

Figure 9A:
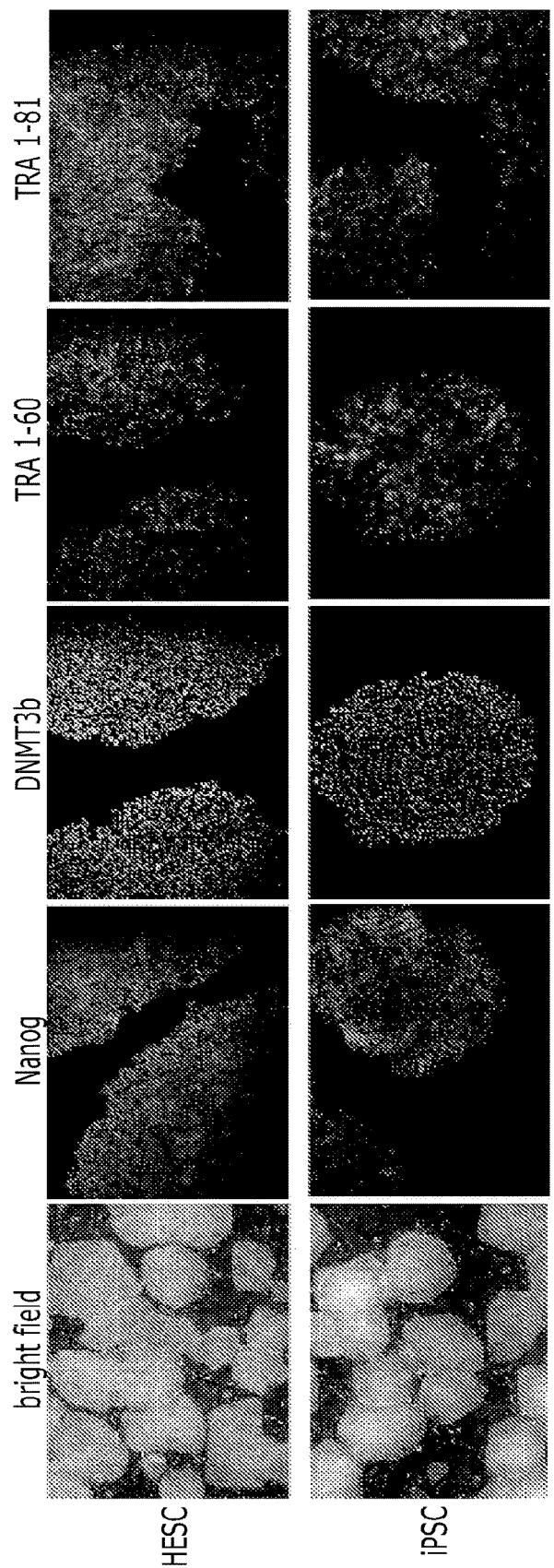
FIGS. 9A and 9B illustrate exemplary embodiments in accordance with the present invention.
Figure 9B:
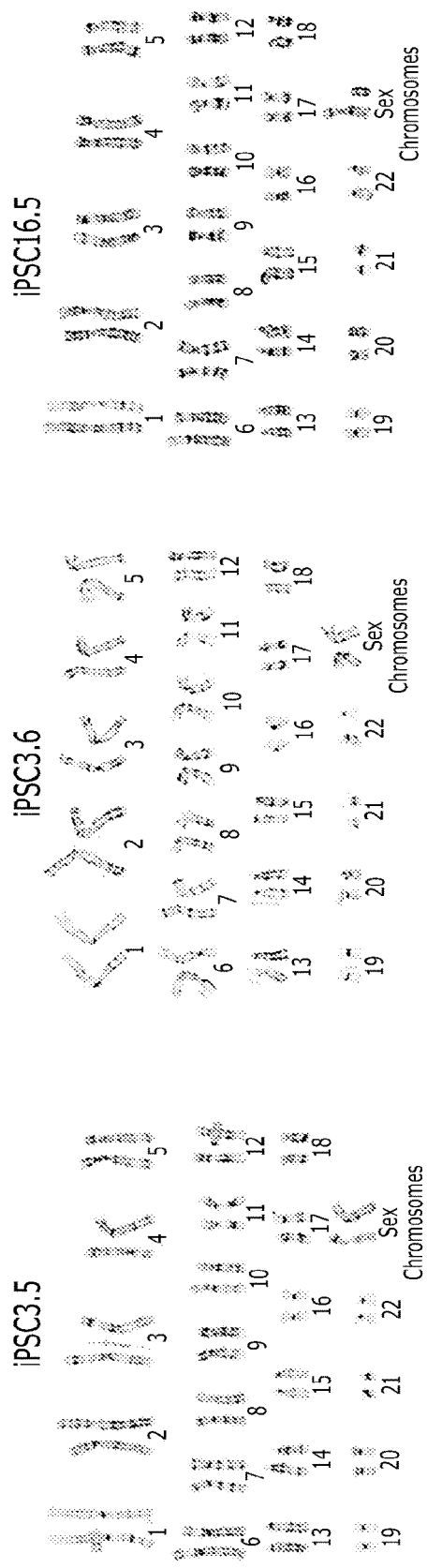

FIGS. 9a and 9b illustrate exemplary embodiments in accordance with the present invention, showing the characterization of induced pluripotent stem cell lines. All cell lines were compared to either hESC-H9 or hESC-H1 for morphology, pluripotency marker expression and karyotype. (a) Example of hESC and iPSC morphology and expression of pluripotency markers NANOG, DNMT3b, TRA 1-60 and TRA 1-81. (b) Examples of karyotypic analysis of iPSC lines 3.5, 3.6 and 16.5.

Figure 10A:
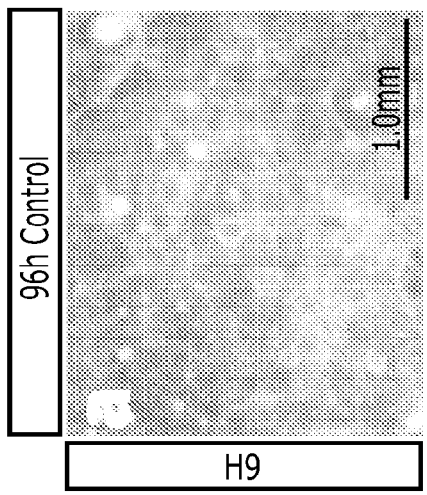
Figure 10B:
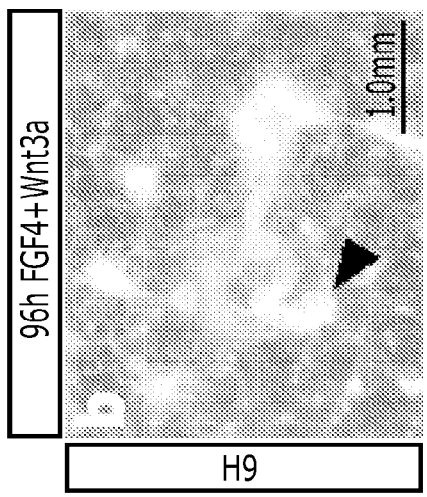
Figure 10C:
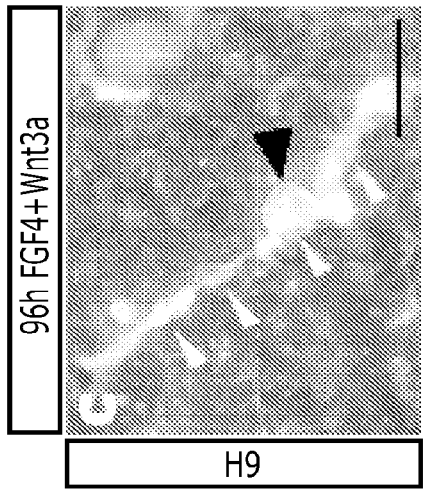
Figure 10D:
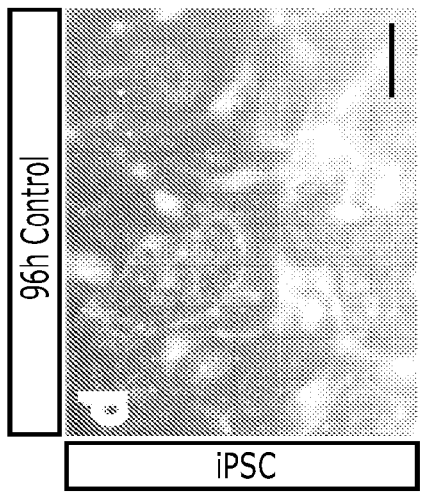
Figure 10E:
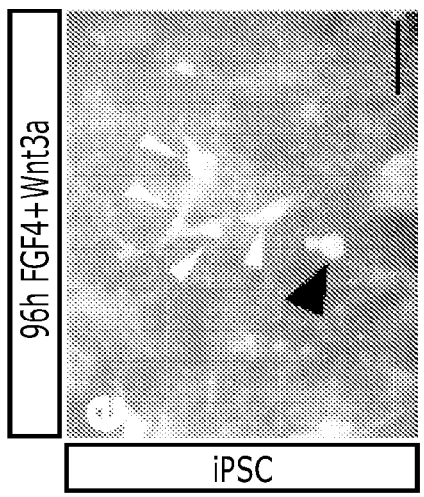
Figure 10F:
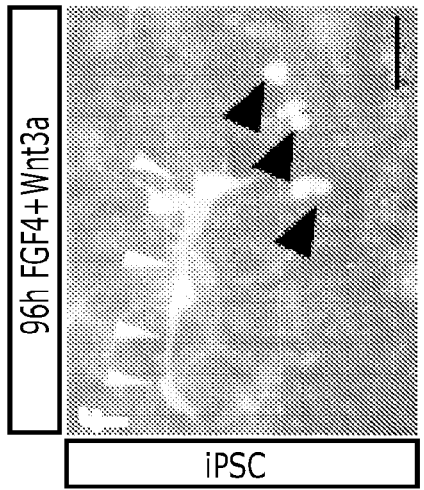
Figure 11G:
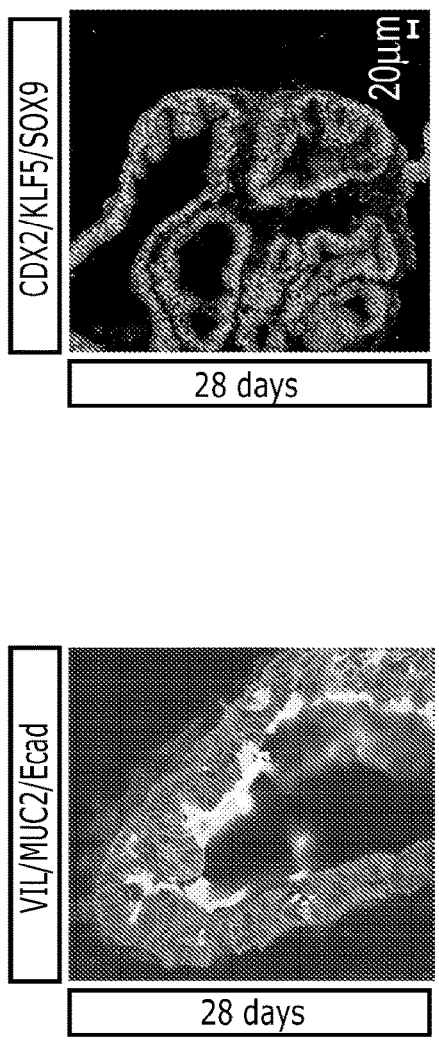
Figure 11G:
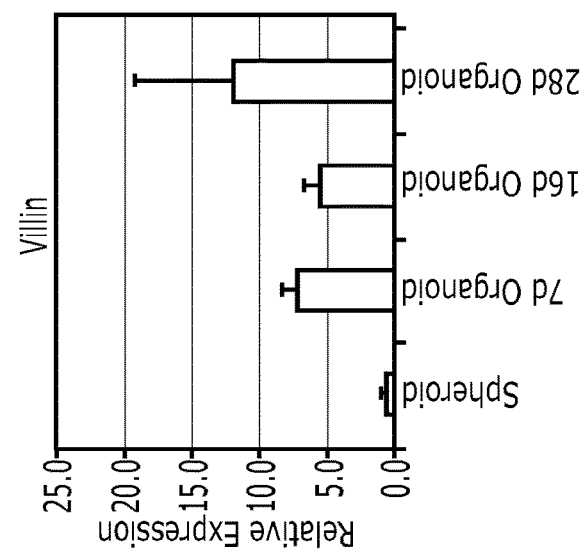
Figure 11G:
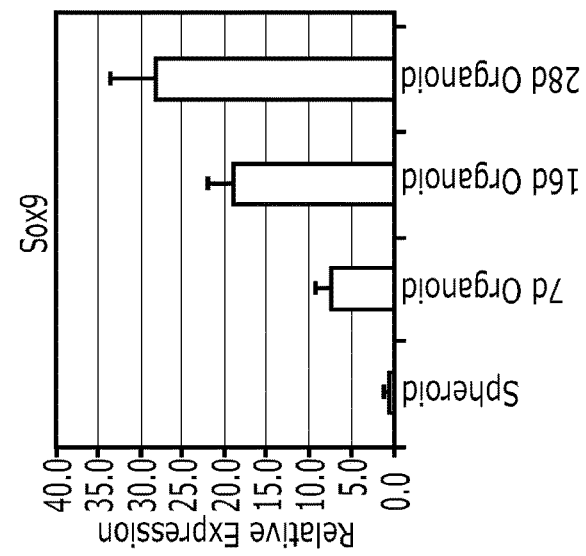
Figure 11G:
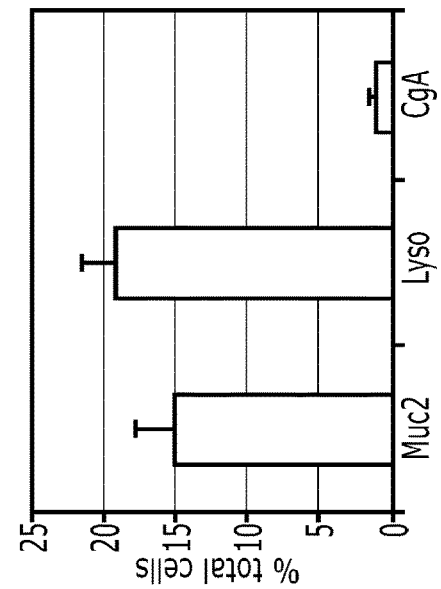
Figure 11L:
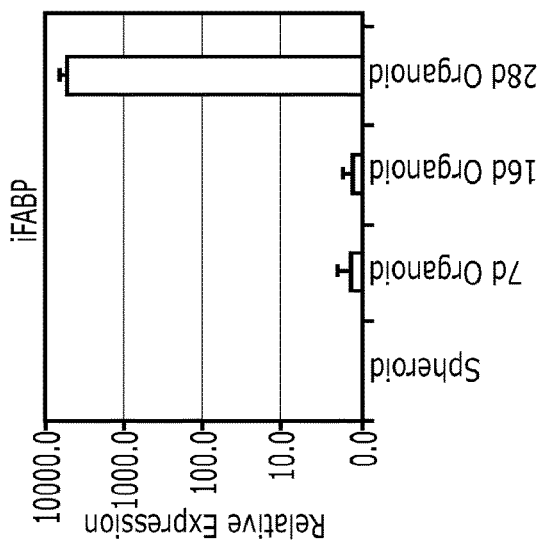
Figure 11K:
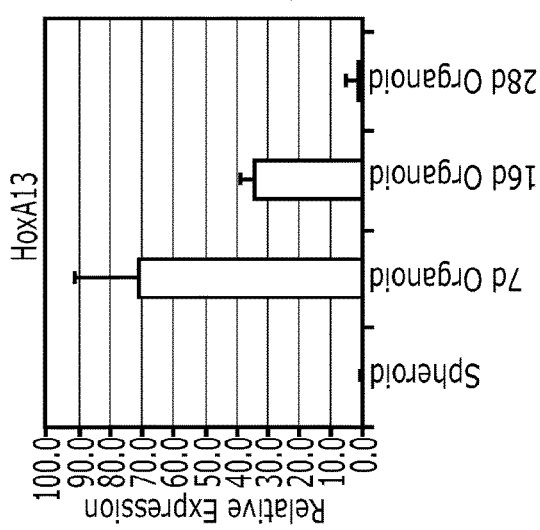
Figure 11J:
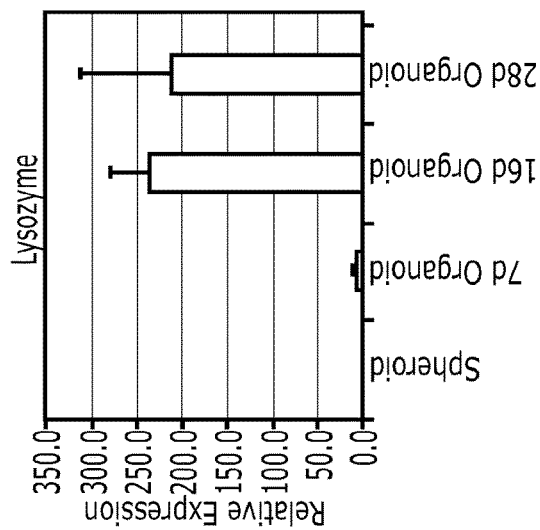
Figure 11M:
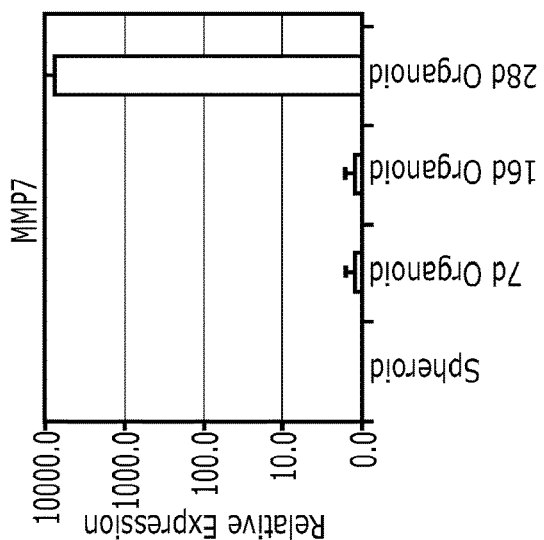

FIGS. 10a through 10g4 illustrate exemplary embodiments in accordance with the present invention, showing the morphologic comparison of hESC and iPSC organoid formation. (a)-(f) Hindgut spheroid formation from H9 human ESCs (a)-(c) or iPSCs (d)-(f) that were differentiated into endoderm and cultured without growth factors, see (a) and (d); or with 500 ng/mL FGF4+Wnt3a, see (b), (c), (e), and (0, for 96 hours. Control cultures contained little evidence of three dimensional structures (a,d) whereas FGF4+Wnt3a treated cultures contained tube like structures (yellow arrowheads; (c), (e), (f)) and free floating spheroids (black arrowheads; (b), (c), (e), (f)). (g) Examples of four different iPSC spheroids that were expanded in matrigel for 18 days (g1)-(g4). As with hESC-derived organoids, iPSC organoids contain an internal epithelium surrounded by mesenchyme.

Example 3

Cytodifferentiation of PSCs into Mature Intestinal Cell Types

Between 18 and 28 days in vitro, it was observed that cytodifferentiation of the stratified epithelium into a columnar epithelium containing brush borders and all of the major cell lineages of the gut as determined by immunofluorescence and RT-qPCR (FIG. 4 and FIG. 11). By 28 days of culture Villin (FIG. 4a, a') and DPPIV were localized to the apical surface of the polarized columnar epithelium and transmission electron microscopy revealed a brush border of apical microvilli indistinguishable from those found in mature intestine (FIG. 4d and FIG. 5). Cell counting revealed that the epithelium contained approximately 15% MUC2+ goblet cells (FIGS. 4a, a'), which secrete mucin into the lumen of the organoid (FIG. 11e), 18% lysozyme positive cells that are indicative of Paneth cells (FIG. 4b, b') and about 1% chromogranin A-expressing enteroendocrine cells (FIG. 4 c, c'; and FIG. 11). RT-qPCR confirmed presence of additional markers of differentiated enterocytes (iFABP) and Paneth cells (MMP7). The analysis of GATA4 and GATA6 and HOX factors suggested that individual organoids are a mix of proximal (GATA4+/GATA6+) and distal (GATA4-/GATA6+)(HOXA13-expressing) intestine (FIG. 12).

The molecular basis of congenital malformations in humans is often inferred from studies in model organisms. For example, Neurogenin 3 (NEUROG3) was investigated as a candidate gene responsible for congenital loss of intestinal enteroendocrine cells in humans because of its known role in enteroendocrine cell development in mouse. Since it has not yet been possible to directly determine if NEUROG3 regulates cytodifferentiation during human intestinal development, a NEUROG3-GFP fusion protein or a GFP-only control was expressed in 28 day human organoids using Adenoviral-mediated transduction. After six days, Ad-NEUROG3 infected organoids contained 5-fold more chromograninA+ endocrine cells than control organoids (Ad-EGFP) (FIG. 4e, f), demonstrating that NEUROG3 expression was sufficient to promote an enteroendocrine cell fate. The fact that cells that maintained NEUROG3-GFP expression did not differentiate into chromograninA+ endocrine cells is consistent with need to down regulate NEUROG3 prior to terminal differentiation.

More details can be found in, for example, Haveri, H., et al. Transcription factors GATA-4 and GATA-6 in normal and neoplastic human gastrointestinal mucosa. *BMC Gastroenterology* 8, 9 (2008); Wang, J., et al. Mutant neurogenin-3 in congenital malabsorptive diarrhea.[see comment]. *New England Journal of Medicine* 355, 270-280 (2006); Jenny, M., et al. Neurogenin3 is differentially required for endocrine cell fate specification in the intestinal and gastric epithelium. *Embo J* 21, 6338-6347 (2002); Lee et al., Neurogenin 3 is essential for the proper specification of gastric enteroendocrine cells and the maintenance of gastric epithelial cell identity. *Genes Dev* 16, 1488-1497 (2002); Lopez-Diaz, L., et al. Intestinal Neurogenin 3 directs differentiation of a bipotential secretory progenitor to endocrine cell rather than goblet cell fate. *Dev Biol* 309, 298-305 (2007); Ootani, A., et al. Sustained in vitro intestinal epithelial culture within a Wnt-dependent stem cell niche. *Nat Med* 15, 701-706 (2009); Zhou, Q., Brown, J., Kanarek, A., Raj agopal, J. & Melton, D. A. In vivo reprogramming of adult pancreatic exocrine cells to beta-cells. *Nature* 455, 627-632 (2008); each of which is incorporated herein in its entirety.

FIGS. 4a through 4f illustrate exemplary embodiments in accordance with the present invention, showing the formation of all major intestinal cell types and directed differentiation of the endocrine lineage with Neurogenin 3 (NEUROG3). 28 day iPSC-derived or 48 day H9 HES-derived organoids were analyzed for villin (VIL) (a) and (a'), the goblet cell marker mucin (MUC2); (b) and (b'), the paneth cell marker lysozyme (LYSO); or (c) and (c'), the endocrine cell marker chromogranin A (CGA). (d) Electron micrograph showing an enterocyte cell with a characteristic brush border with microvilli (inset). (e) and (f) Promoting endocrine cell lineage development using adenoviral-mediated expression of Neurogenin 3 (NEUROG3). pAd-NEUROG3 causes a 5-fold increase in the percent of CGA+ cells compared to a control adenovirus (pAd-GFP). Error bars denote standard error mean. Significance is shown by;* (p=0.005)

Figure 5C:
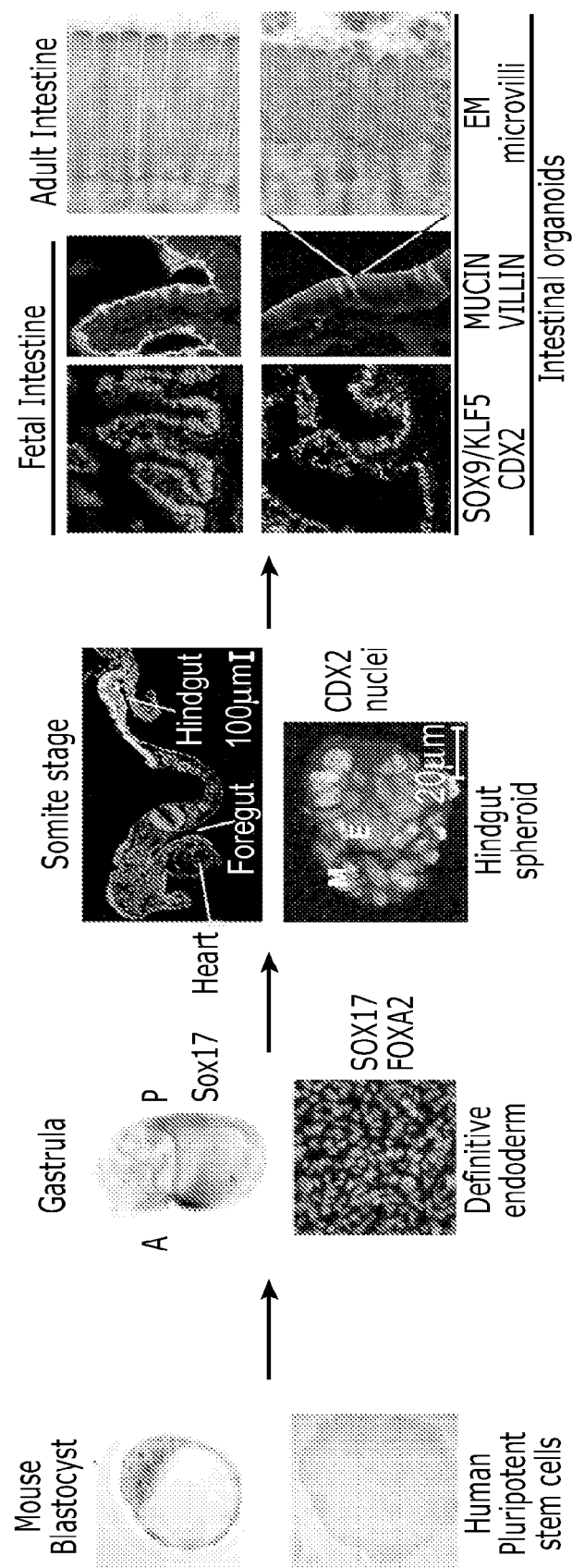

FIGS. 5a-5c illustrate exemplary embodiments, showing a model comparing embryonic intestinal development versus directed differentiation of human PSCs into intestinal tissue in vitro. (a) Schematic of human intestinal development. At the blastocyst stage, the inner cell mass (ICM) gives rise to the entire embryo. The ICM is also the source of embryonic stem cells. At the gastrula stage, the embryo contains the three germ layers including the embryonic/definitive endoderm (yellow). The definitive endoderm forms a primitive gut tube, with the hindgut forming in the posterior region of the embryo. The hindgut undergoes intestinal morphogenesis forming the small and large intestines. (b) Schematic of directed differentiation of PSCs into intestinal tissue. PSCs cultured for 3 days in ActivinA form definitive endoderm (DE) co-expressing SOX17 and FOXA2. DE cultured for 4 days in FGF4 and Wnt3a (500 ng/ml each) form three-dimensional hindgut spheroids expressing the posterior marker CDX2. Spheroids formed intestinal organoids when grown in three dimensional conditions that favor expansion and differentiation of intestinal precursors (matrigel with 500 ng/ml R-Spondin1, 100 ng/ml Noggin and 50 ng/ml EGF. (c) Side-by-side comparison of mouse embryonic intestinal development (top) and human intestinal organoid development (bottom). PSCs underwent staged differentiation in a manner that was highly reminiscent of embryonic intestinal development and formed intestinal tissue. Stages of development in c are the same as schematically shown in (a) and (b).

FIGS. 11a through 11m illustrate exemplary embodiments in accordance with the present invention, showing the molecular analysis of stages of epithelial growth, maturation and cytodifferentiation. (a) 96 hours after FGF4+Wnt3a exposure, hindgut spheroids contained a highly proliferative cuboidal epithelium that expressed CDX2. (b)-(d) 18 day iPSC-derived organoids contained a pseudostratified epithelium that broadly expressed CDX2, KLF5 and SOX9 (b), had weak apical villin staining (c), and had begun expressing markers of cytodifferentiation including lysozyme (Lyso) (d). (e) and (f) At 28 days, organoids secreted mucin into the lumen (e-green), broadly expressed CDX2 and KLF5 and showed restricted expression of SOX9 (f). (g) The number of cells that expressed cytodifferentiation markers ChromograninA (ChA), lysozyme (Lyso) or Mucin (Muc2) was quantified and represented as a percent of total CDX2+ epithelial cells in 28d hESC organoids. (h)-(m) Quantitative analysis of intestinal markers SOX9, Villin (enterocytes), Lysozyme (Paneth cells), HOXA13, IFABP (enterocytes) and MMP7 (Paneth cells) during intestinal organoid development by RT-qPCR. Error bars denote standard deviation of triplicates.

FIGS. 12a and 12b illustrate exemplary embodiments in accordance with the present invention, showing GATA factor expression. (a) H9 hESC derived organoids show that most Cdx2 (blue) positive nuclei express Gata6 (red), whereas only a few nuclei express Gata4 (green, white arrowheads). Gata4/6 double positive cells (white arrowheads) are indicative of proximal intestine, where as Gata6+/Gata4− cells are indicative of distal intestine. (b) human iPSC derived organoids show that almost all Cdx2 positive cells (blue) are Gata6 positive (red). In this example, the organoid did not express Gata4 (green) in this section of tissue, indicating that this intestinal tissue is distal intestine.

Example 4

Mesenchymal Differentiation into Smooth Muscle

Figure 13C:
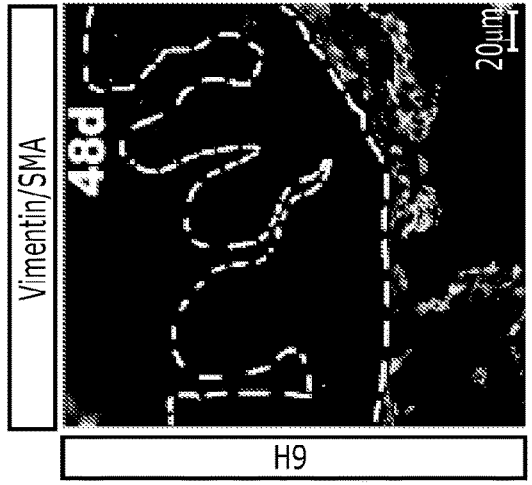
FIGS. 13A-13F illustrate exemplary embodiments in accordance with the present invention.
Figure 13F:
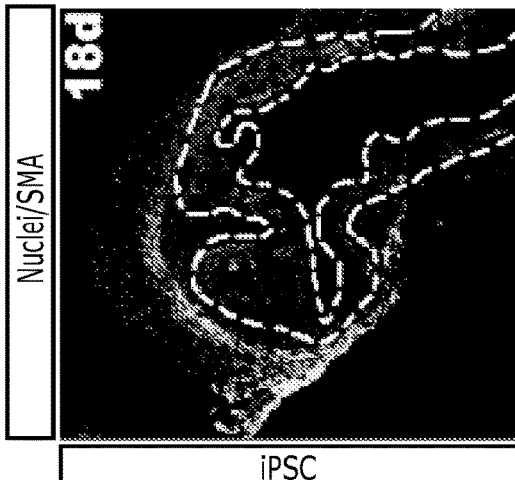
Figure 13B:
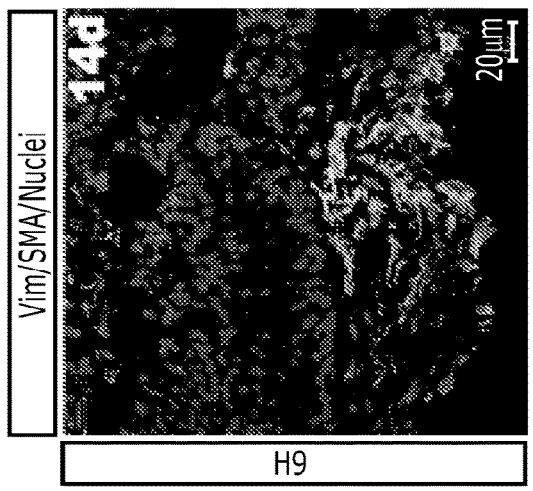
Figure 13E:
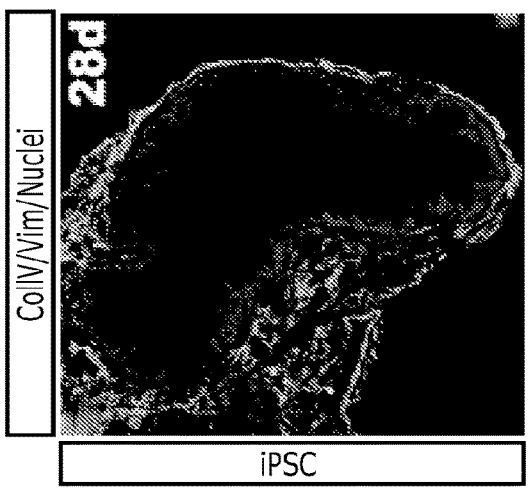

During intestinal development, epithelial and mesenchymal differentiation is regulated via a series of reciprocal signaling events. In PSC-derived cultures, the gut mesenchyme, which likely arises from the few mesoderm cells found in DE cultures, underwent stereotypic differentiation similar to developing mesenchyme in vivo. In the early stages of culture the mesenchyme underwent extensive proliferation (FIG. 3) and formed a homogeneous vimentin+/collagenIV+ layer around the epithelium (FIG. 13) similar to an e12.5 embryonic intestine (FIG. 8). By 18 days there was evidence of regional expression collagen IV, vimentin, or smooth muscle actin (SMA) in different mesenchymal layers (FIGS. 13d and 13f). By 28 days SMA+ cells had further expanded around the epithelium and by 48 days became one of several thin layers of cells adjacent to the epithelium (FIG. 13c). The fact that intestinal mesenchyme differentiation coincided with overlying epithelium suggests that epithelial-mesenchymal crosstalk may be important in the development of PSC-derived intestinal organoids.

In conclusion, this is the first report demonstrating that human PSCs can be efficiently directed to differentiate in vitro into intestinal tissue that includes multiple secretory and absorptive cell types. These findings establish an accessible and genetically tractable system to investigate the molecular basis of human congenital gut defects in vitro and to generate intestinal tissue for transplantation. Moreover human intestinal cultures are a potentially powerful tool for mechanistic studies of drug transport and absorption.

More details can be found in, for example, Zorn, A. M. & Wells, J. M. Vertebrate Endoderm Development and Organ Formation. *Annu Rev Cell Dev Biol* 25, 1-31 (2009); McLin, V. A., Henning, S. J. & Jamrich, M. The role of the visceral mesoderm in the development of the gastrointestinal tract. *Gastroenterology* 136, 2074-2091 (2009); Spence, J. R. & Wells, J. M. Translational embryology: Using embryonic principles to generate pancreatic endocrine cells from embryonic stem cells. *Developmental Dynamics* 236, 3218-3227. (2007); each of which is incorporated herein in its entirety.

Figure 13A:
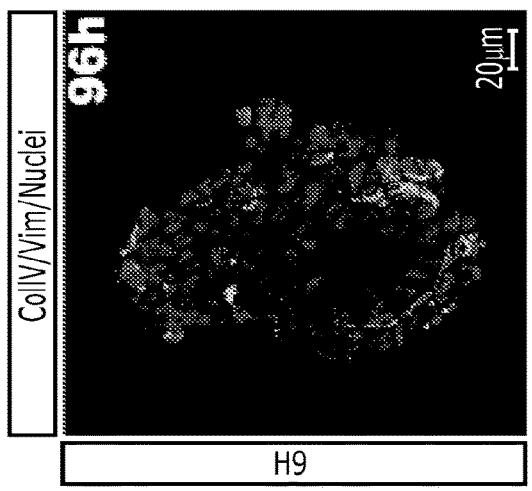
Figure 13D:
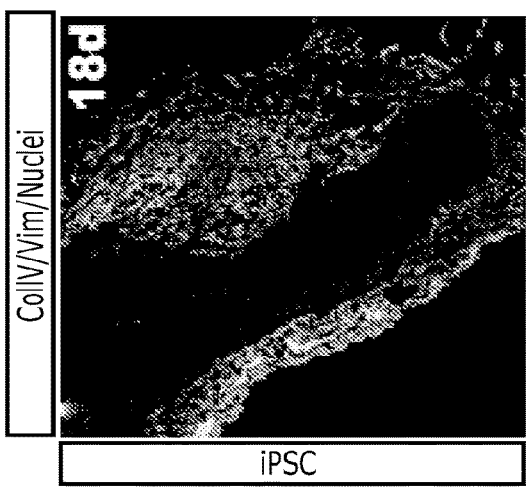

FIGS. 13a and 13f illustrate exemplary embodiments in accordance with the present invention, showing mesenchymal development. (a)-(f) Expression of the pan-mesenchymal markers Collagen IV (ColIV, red) and Vimentin (Vim, green) and the mesenchymal differentiation marker smooth muscle actin (SMA) during organoid development. a, 96 hour H9 spheroid showed Collagen IV staining (red) in the basal layer under the epithelium and weak expression of vimentin (green). b and d, By 14 to 18 days Vimentin and Collagen IV was broadly expressed in the mesenchyme surrounding the organoid epithelium. (b), (c), (f) Smooth muscle actin (SMA) was broadly expressed in 14 day organoids (b) but was restricted to a ring of cells in the 18 day organoid (f). SMA progressively became restricted to a thin layer of mesenchyme surrounding the epithelium at 48 days (c). Nuclei are stained with Draq5 and pseudo-colored blue where indicated.

Example 5

Generation and Characterization of Human iPSC Lines

For preparation of primary keratinocytes from human foreskins, tissues were cultured in dispase to remove the dermis from the epidermis, then trypsinized and cultured in serum-free low calcium medium (Epilife medium, Cascade Biologics, Portland, Oreg.) and antibiotics. For generating iPSC lines, human keratinocytes were transduced with recombinant retroviruses expressing Oct4, Sox2, Klf4 and c-Myc and plated onto mouse embryonic fibroblast (MEF) feeders in the presence of the HDAC inhibitor valproic acid. After 2-4 weeks, iPSC colonies were picked and expanded into cell lines. The iPSC lines were expanded and passaged and analyzed for hESC-like morphology, expression of pluripotency markers (SSEA3 and Tra1-81), and karyotype. iPSC lines were maintained on MEFs or in feeder-free, defined conditions.

Example 6

Generation and Characterization of Induced Pluripotent Stem Cell Lines

Normal human skin keratinocytes (NHSK) were obtained from donors with informed consent (CCHMC IRB protocol CR_2008-1331). NHSKs were isolated from punch biopsies following trypsinization and subsequent culture on irradiated NIH3T3 feeder cells in F media. For iPSC generation, NHSKs were transduced on two consecutive days with a 1:1:1:1 mix of recombinant RD114-pseudotyped retroviruses expressing Oct4, Sox2, Klf4 and cMyc in the presence of 8 µg/mL polybrene. Twenty-four hours after the second transduction the virus mix was replaced with fresh F media and cells were incubated for an additional three days. Cells were then trypsinized and seeded into 6 well dishes containing $1.875 \times 10^5$ irradiated mouse fibroblasts per well and Epilife medium. On the following day, media was replaced with DMEM/F12 50:50 media supplemented with 20% knockout serum replacement, 1 mM L-glutamine, 0.1 mM β-mercaptoethanol, 1× non-essential amino acids, 4 ng/mL basic fibroblast growth factor, and 0.5 mM valproic acid. Morphologically identifiable iPSC colonies arose after 2-3 weeks and were picked manually, expanded and analyzed for expression of human pluripotent stem cell markers Nanog, DNMT3b, Tra1-60 and Tra1-81. Early passage iPSC lines were adapted to feeder-free culture conditions consisting of maintenance in mTeSR1 (Stem Cell Technologies) in culture dishes coated with matrigel (BD Biosciences) and lines were karyotyped.

More details can be found in, for example, Lambert, P. F., et al. Using an immortalized cell line to study the HPV life cycle in organotypic "raft" cultures. *Methods in molecular medicine* 119, 141-155 (2005); Takahashi et al. Induction of pluripotent stem cells from adult human fibroblasts by defined factors. *Cell* 131, 861-872 (2007); Takahashi, K. & Yamanaka, S. Induction of pluripotent stem cells from mouse embryonic and adult fibroblast cultures by defined factors. *Cell* 126, 663-676 (2006); D'Amour et al., Production of pancreatic hormone-expressing endocrine cells from human embryonic stem cells. *Nat Biotechnol* 24, 1392-1401 (2006); Richards et al., The transcriptome profile of human embryonic stem cells as defined by SAGE. *Stem Cells* 22, 51-64 (2004); Thomson, J. A., et al. Embryonic stem cell lines derived from human blastocysts. *Science* 282, 1145-1147 (1998); each of which is incorporated herein in its entirety.

Example 7

Microarray Analysis of Human ESCs, iPSCs and DE Cultures

For microarray analysis, RNA was isolated from undifferentiated and 3-day activin treated hESC and iPSC cultures and used create target DNA for hybridization to Affymetrix Human 1.0 Gene ST Arrays using standard procedures (Affymetrix, Santa Clara, Calif.). Independent biological triplicates were performed for each cell line and condition. Affymetrix microarray Cel files were subjected to Robust Multichip Average (RMA) normalization in GeneSpring 10.1. Probe sets were first filtered for those that are overexpressed or underexpressed and then subjected to statistical analysis for differential expression by 3 fold or more between undifferentiated and differentiated cultures with $p<0.05$ using the Students T-test. This procedure generated a list of 530 probe sets, as shown in Table 2. Log 2 gene expression ratios were then subjected to hierachical clustering using the standard correlation distance metric as implemented in GeneSpring.

TABLE 2

Variations of Transcript levels (2-fold or more) during DE formation in hESC-H9 and iPSC lines 3.12, 3.5 and 3.6

| GENE SYMBOL | DIFF'D-H9] vs [UNDIFF'D-H9] (folds) | [DIFF'D-IPSC3.12] vs [UNDIFF'D-IPSC3.12] (folds) | [Diff'd-iPSC3.4] vs [Undiff'd-iPSC3.4] (folds) | GENE DESCRIPTION |
|---|---|---|---|---|
| CER1 | 137.61 | 67.98 | 66.76 | cerberus 1, cysteine knot superfamily, homolog (Xenopus laevis) |
| HAS2 | 32.29 | 15.27 | 13.43 | hyaluronan synthase 2 |
| PRDM1 | 30.35 | 24.92 | 21.56 | PR domain containing 1, with ZNF domain |
| SEMA3E | 30.17 | 21.66 | 19.36 | sema domain, immunoglobulin domain (Ig), short basic domain, secreted, (semaphorin) 3E |
| MFAP4 | 28.35 | 29.08 | 35.47 | microfibrillar-associated protein 4 |
| EOMES | 28.31 | 19.85 | 27.72 | eomesodermin homolog (Xenopus laevis) |
| CYP26A1 | 28.12 | 41.18 | 47.21 | cytochrome P450, family 26, subfamily A, polypeptide 1 |
| SLC40A1 | 27.82 | 33.13 | 34.77 | solute carrier family 40 (iron-regulated transporter), member 1 |
| CXCR4 | 24.73 | 23.19 | 19.91 | chemokine (C—X—C motif) receptor 4 |
| FGF17 | 17.92 | 15.78 | 19.00 | fibroblast growth factor 17 |
| TRPA1 | 17.40 | 25.46 | 23.50 | transient receptor potential cation channel, subfamily A, member 1 |
| ANKRD1 | 17.20 | 11.45 | 8.97 | ankyrin repeat domain 1 (cardiac muscle) |
| LOC100132916 | 15.91 | 12.59 | 9.65 | similar to hCG1811192 |
| PCDH10 | 15.88 | 18.81 | 23.07 | protocadherin 10 |
| RHOBTB3 | 15.76 | 12.01 | 8.61 | Rho-related BTB domain containing 3 |
| LGR5 | 15.44 | 12.18 | 12.88 | leucine-rich repeat-containing G protein-coupled receptor 5 |
| CD48 | 14.69 | 18.02 | 15.22 | |
| ST8SIA4 | 14.68 | 10.83 | 9.75 | ST8 alpha-N-acetyl-neuraminide alpha-2,8-sialyltransferase 4 |
| COL5A2 | 14.57 | 13.25 | 15.28 | collagen, type V, alpha 2 |
| COLEC12 | 13.69 | 11.08 | 12.98 | collectin sub-family member 12 |
| FLRT3 | 12.96 | 15.64 | 11.19 | fibronectin leucine rich transmembrane protein 3 |
| CHL1 | 12.67 | 2.89 | 3.63 | cell adhesion molecule with homology to L1CAM (close homolog of L1) |
| ELOVL2 | 12.67 | 6.73 | 6.61 | elongation of very long chain fatty acids (FEN1/Elo2, SUR4/Elo3, yeast)-like 2 |
| CCL2 | 12.64 | 18.30 | 14.69 | chemokine (C-C motif) ligand 2 |
| MIXL1 | 12.51 | 7.17 | 8.06 | Mix1 homeobox-like 1 (Xenopus laevis) |
| MGST2 | 11.94 | 15.71 | 13.68 | microsomal glutathione S-transferase 2 |
| EHHADH | 11.32 | 9.12 | 8.12 | enoyl-Coenzyme A, hydratase/3-hydroxyacyl Coenzyme A dehydrogenase |
| PLXNA2 | 11.05 | 9.37 | 9.50 | plexin A2 |
| DIO3 | 10.97 | 9.31 | 7.22 | deiodinase, iodothyronine, type III |
| KLF8 | 10.94 | 6.17 | 5.97 | Kruppel-like factor 8 |
| PEG10 | 10.92 | 3.35 | 3.97 | paternally expressed 10 |
| TDRD7 | 10.91 | 9.40 | 9.32 | tudor domain containing 7 |
| MANEA | 10.90 | 8.67 | 8.97 | mannosidase, endo-alpha |
| UPK1B | 10.83 | 5.46 | 5.74 | uroplakin 1B |
| ROR2 | 10.22 | 8.35 | 8.35 | receptor tyrosine kinase-like orphan receptor 2 |
| CCKBR | 9.79 | 12.68 | 9.37 | cholecystokinin B receptor |
| DKK1 | 9.66 | 6.27 | 7.27 | dickkopf homolog 1 (Xenopus laevis) |
| SERPINB9 | 9.32 | 10.27 | 10.52 | serpin peptidase inhibitor, clade B (ovalbumin), member 9 |
| OR5P2 | 9.18 | 5.08 | 6.24 | olfactory receptor, family 5, subfamily P, member 2 |
| OVCH2 | 9.06 | 6.77 | 7.92 | ovochymase 2 |
| FRZB | 8.79 | 5.92 | 5.20 | frizzled-related protein |
| SAMD3 | 8.40 | 8.88 | 7.82 | sterile alpha motif domain containing 3 |
| HHEX | 8.37 | 15.27 | 10.62 | hematopoietically expressed homeobox |
| PPAPDC1A | 8.00 | 4.50 | 3.94 | phosphatidic acid phosphatase type 2 domain containing 1A |
| MYL7 | 7.96 | 6.41 | 7.32 | myosin, light chain 7, regulatory |
| PLSCR4 | 7.87 | 7.11 | 8.62 | phospholipid scramblase 4 |
| ITGA5 | 7.82 | 4.31 | 4.38 | integrin, alpha 5 (fibronectin receptor, alpha polypeptide) |

TABLE 2-continued

Variations of Transcript levels (2-fold or more) during DE formation in hESC-H9 and iPSC lines 3.12, 3.5 and 3.6

| GENE SYMBOL | DIFF'D-H9] vs [UNDIFF'D-H9] (folds) | [DIFF'D-IPSC3.12] vs [UNDIFF'D-IPSC3.12] (folds) | [Diff'd-iPSC3.4] vs [Undiff'd-iPSC3.4] (folds) | GENE DESCRIPTION |
|---|---|---|---|---|
| ENC1 | 7.76 | 3.37 | 3.08 | ectodermal-neural cortex (with BTB-like domain) |
| TNC | 7.73 | 6.30 | 9.01 | tenascin C (hexabrachion) |
| C5 | 7.59 | 14.18 | 14.56 | complement component 5 |
| SOX17 | 7.34 | 7.29 | 7.58 | SRY (sex determining region Y)-box 17 |
| RLBP1L2 | 7.31 | 6.87 | 6.65 | retinaldehyde binding protein 1-like 2 |
| VAMP8 | 7.30 | 3.74 | 4.09 | vesicle-associated membrane protein 8 (endobrevin) |
| PLCE1 | 7.11 | 7.55 | 6.70 | phospholipase C, epsilon 1 |
| NTN4 | 7.09 | 6.11 | 5.15 | netrin 4 |
| PROS1 | 7.01 | 4.02 | 4.07 | protein S (alpha) |
| LRIG3 | 6.97 | 9.55 | 9.18 | leucine-rich repeats and immunoglobulin-like domains 3 |
| CDH2 | 6.89 | 8.08 | 7.38 | cadherin 2, type 1, N-cadherin (neuronal) |
| CFLAR | 6.84 | 6.90 | 6.63 | CASP8 and FADD-like apoptosis regulator |
| ARHGAP24 | 6.74 | 5.33 | 5.92 | Rho GTPase activating protein 24 |
| C6ORF60 | 6.67 | 7.85 | 6.40 | chromosome 6 open reading frame 60 |
| MCC | 6.48 | 3.48 | 3.37 | mutated in colorectal cancers |
| GPR177 | 6.42 | 5.21 | 4.84 | G protein-coupled receptor 177 |
| CPE | 6.36 | 7.33 | 6.89 | carboxypeptidase E |
| C9ORF19 | 6.14 | 5.15 | 5.52 | chromosome 9 open reading frame 19 |
| PLSCR1 | 5.99 | 4.35 | 3.70 | phospholipid scramblase 1 |
| BMP2 | 5.95 | 7.43 | 6.96 | bone morphogenetic protein 2 |
| OR5P3 | 5.80 | 3.50 | 4.65 | olfactory receptor, family 5, subfamily P, member 3 |
| FN1 | 5.77 | 3.80 | 3.73 | fibronectin 1 |
| TBC1D9 | 5.72 | 5.94 | 5.11 | TBC1 domain family, member 9 (with GRAM domain) |
| VWF | 5.69 | 5.27 | 5.12 | von Willebrand factor |
| NODAL | 5.66 | 5.77 | 5.00 | nodal homolog (mouse) |
| GSC | 5.57 | 5.37 | 5.22 | goosecoid homeobox |
| SMAD6 | 5.53 | 2.54 | 2.97 | SMAD family member 6 |
| S100Z | 5.52 | 4.68 | 4.36 | S100 calcium binding protein Z |
| ARHGAP29 | 5.52 | 4.47 | 4.19 | Rho GTPase activating protein 29 |
| LHX1 | 5.51 | 4.72 | 4.60 | LIM homeobox 1 |
| ARSE | 5.42 | 5.47 | 5.25 | arylsulfatase E (chondrodysplasia punctata 1) |
| CNGA4 | 5.39 | 4.06 | 4.78 | cyclic nucleotide gated channel alpha 4 |
| AHNAK | 5.34 | 4.93 | 4.71 | |
| SEPP1 | 5.28 | 5.27 | 4.42 | selenoprotein P, plasma, 1 |
| PROS1 | 5.23 | 3.60 | 3.95 | protein S (alpha) |
| CALCR | 5.20 | 3.44 | 3.13 | calcitonin receptor |
| IER3 | 5.14 | 6.06 | 5.38 | immediate early response 3 |
| MAN1A1 | 5.12 | 4.60 | 4.23 | mannosidase, alpha, class 1A, member 1 |
| KCNG1 | 5.09 | 3.70 | 4.11 | potassium voltage-gated channel, subfamily G, member 1 |
| BNIP3 | 5.08 | 3.56 | 3.35 | BCL2/adenovirus E1B 19 kDa interacting protein 3 |
| H2AFY2 | 5.05 | 7.17 | 6.81 | H2A histone family, member Y2 |
| FAM122C | 5.03 | 4.61 | 4.20 | family with sequence similarity 122C |
| FMN2 | 5.03 | 3.77 | 4.77 | formin 2 |
| PPFIBP2 | 5.03 | 4.02 | 4.10 | PTPRF interacting protein, binding protein 2 (liprin beta 2) |
| ARRDC3 | 4.99 | 4.14 | 3.33 | arrestin domain containing 3 |
| GATM | 4.99 | 4.95 | 3.94 | glycine amidinotransferase (L-arginine:glycine amidinotransferase) |
| C21ORF129 | 4.97 | 10.33 | 8.83 | chromosome 21 open reading frame 129 |
| KRT8 | 4.96 | 2.41 | 2.50 | keratin 8 |
| ADAM19 | 4.96 | 4.37 | 4.36 | ADAM metallopeptidase domain 19 (meltrin beta) |
| BTG2 | 4.90 | 3.29 | 3.20 | BTG family, member 2 |
| ARRB1 | 4.90 | 2.66 | 3.03 | arrestin, beta 1 |
| AGL | 4.90 | 3.65 | 3.09 | amylo-1, 6-glucosidase, 4-alpha-glucanotransferase (glycogen debranching enzyme, glycogen storage disease type III) |

TABLE 2-continued

Variations of Transcript levels (2-fold or more) during DE formation in hESC-H9 and iPSC lines 3.12, 3.5 and 3.6

| GENE SYMBOL | [DIFF'D-H9] vs [UNDIFF'D-H9] (folds) | [DIFF'D-IPSC3.12] vs [UNDIFF'D-IPSC3.12] (folds) | [Diff'd-iPSC3.4] vs [Undiff'd-iPSC3.4] (folds) | GENE DESCRIPTION |
|---|---|---|---|---|
| IFLTD1 | 4.86 | 2.44 | 2.79 | intermediate filament tail domain containing 1 |
| TIPARP | 4.84 | 4.13 | 3.77 | TCDD-inducible poly(ADP-ribose) polymerase |
| NFKBIA | 4.83 | 4.56 | 4.41 | nuclear factor of kappa light polypeptide gene enhancer in B-cells inhibitor, alpha |
| RNF19A | 4.79 | 5.77 | 4.63 | ring finger protein 19A |
| PDZK1 | 4.77 | 3.94 | 3.57 | PDZ domain containing 1 |
| RNF152 | 4.77 | 4.66 | 4.52 | ring finger protein 152 |
| RPRM | 4.76 | 4.83 | 4.58 | reprimo, TP53 dependent G2 arrest mediator candidate |
| TGFB1 | 4.74 | 2.98 | 3.54 | transforming growth factor, beta 1 |
| CAMK2D | 4.64 | 4.00 | 3.77 | calcium/calmodulin-dependent protein kinase (CaM kinase) II delta |
| ARL4D | 4.62 | 4.07 | 3.95 | ADP-ribosylation factor-like 4D |
| ARHGAP28 | 4.60 | 3.54 | 3.27 | Rho GTPase activating protein 28 |
| C8ORF49 | 4.59 | 4.09 | 3.45 | chromosome 8 open reading frame 49 |
| MATN3 | 4.57 | 4.36 | 5.19 | matrilin 3 |
| DUSP10 | 4.54 | 4.45 | 4.76 | dual specificity phosphatase 10 |
| PTPRM | 4.51 | 5.04 | 5.21 | protein tyrosine phosphatase, receptor type, M |
| RNF125 | 4.49 | 3.53 | 3.28 | ring finger protein 125 |
| ACOX3 | 4.48 | 5.42 | 5.45 | acyl-Coenzyme A oxidase 3, pristanoyl |
| SLC22A3 | 4.40 | 4.27 | 5.11 | solute carrier family 22 (extraneuronal monoamine transporter), member 3 |
| IER3 | 4.39 | 4.79 | 4.34 | immediate early response 3 |
| NR0B1 | 4.39 | 11.17 | 9.41 | nuclear receptor subfamily 0, group B, member 1 |
| s1PR3|C9ORF47 | 4.39 | 3.21 | 4.05 | sphingosine-1-phosphate receptor 3| chromosome 9 open reading frame 47 |
| IER3 | 4.39 | 4.80 | 4.34 | immediate early response 3 |
| c8ORF79 | 4.32 | 3.02 | 2.86 | chromosome 8 open reading frame 79 |
| EPSTI1 | 4.32 | 4.91 | 4.62 | epithelial stromal interaction 1 (breast) |
| KRT19 | 4.27 | 2.48 | 2.56 | keratin 19 |
| USP53 | 4.26 | 3.53 | 3.00 | ubiquitin specific peptidase 53 |
| GPSM2 | 4.21 | 5.06 | 4.09 | G-protein signaling modulator 2 (AGS3-like, *C. elegans*) |
| PRSS35 | 4.19 | 5.55 | 5.36 | protease, serine, 35 |
| RELN | 4.13 | 3.02 | 3.30 | reelin |
| RBM24 | 4.12 | 4.75 | 3.60 | RNA binding motif protein 24 |
| RASGEF1B | 4.05 | 3.15 | 3.59 | RasGEF domain family, member 1B |
| MERTK | 4.01 | 3.13 | 3.67 | c-mer proto-oncogene tyrosine kinase |
| OTX2 | 4.01 | 5.22 | 5.32 | orthodenticle homeobox 2 |
| MAML3 | 4.00 | 3.41 | 3.52 | mastermind-like 3 (*Drosophila*) |
| PDE10A | 3.98 | 4.60 | 4.58 | phosphodiesterase 10A |
| PLCXD3 | 3.98 | 3.34 | 2.49 | phosphatidylinositol-specific phospholipase C, X domain containing 3 |
| GREM2 | 3.97 | 3.14 | 3.50 | gremlin 2, cysteine knot superfamily, homolog (*Xenopus laevis*) |
| MYO3A | 3.93 | 4.17 | 4.62 | myosin IIIA |
| NEK7 | 3.92 | 3.53 | 3.02 | NIMA (never in mitosis gene a)-related kinase 7 |
| LEPREL1 | 3.92 | 6.42 | 6.24 | leprecan-like 1 |
| MOBP | 3.92 | 2.68 | 2.52 | myelin-associated oligodendrocyte basic protein |
| KCNH8 | 3.87 | 4.09 | 3.76 | potassium voltage-gated channel, subfamily H (eag-related), member 8 |
| FAM20A | 3.84 | 4.69 | 5.21 | family with sequence similarity 20, member A |
| MID2 | 3.83 | 2.46 | 2.43 | midline 2 |
| SETD7 | 3.82 | 3.65 | 3.68 | SET domain containing (lysine methyltransferase) 7 |
| MYCT1 | 3.79 | 6.63 | 6.07 | myc target 1 |
| KIAA0825 | 3.75 | 4.30 | 4.73 | |
| FLRT2 | 3.74 | 2.88 | 3.40 | fibronectin leucine rich transmembrane protein 2 |
| PREX1 | 3.73 | 2.87 | 3.03 | phosphatidylinositol 3,4,5-trisphosphate-dependent RAC exchanger 1 |

TABLE 2-continued

Variations of Transcript levels (2-fold or more) during DE formation in hESC-H9 and iPSC lines 3.12, 3.5 and 3.6

| GENE SYMBOL | DIFF'D-H9] vs [UNDIFF'D-H9] (folds) | [DIFF'D-IPSC3.12] vs [UNDIFF'D-IPSC3.12] (folds) | [Diff'd-iPSC3.4] vs [Undiff'd-iPSC3.4] (folds) | GENE DESCRIPTION |
|---|---|---|---|---|
| ASAM | 3.73 | 3.68 | 3.58 | adipocyte-specific adhesion molecule |
| CYP1B1 | 3.71 | 2.20 | 2.15 | cytochrome P450, family 1, subfamily B, polypeptide 1 |
| YPEL5 | 3.70 | 2.91 | 2.95 | yippee-like 5 (Drosophila) |
| SEMA5A | 3.69 | 5.53 | 5.37 | sema domain, seven thrombospondin repeats (type 1 and type 1-like), transmembrane domain (TM) and short cytoplasmic domain, (semaphorin) 5A |
| LEFTY2 | 3.68 | 8.55 | 6.11 | left-right determination factor 2 |
| C9ORF52 | 3.62 | 3.58 | 3.12 | chromosome 9 open reading frame 52 |
| SLITRK2\|LOC100129095 | 3.62 | 3.66 | 3.73 | SLIT and NTRK-like family, member 2\|similar to CXorf2 protein |
| SERPINE2 | 3.61 | 3.78 | 3.80 | serpin peptidase inhibitor, clade E (nexin, plasminogen activator inhibitor type 1), member 2 |
| B3GNT5 | 3.57 | 2.85 | 2.91 | UDP-GlcNAc:betaGal beta-1,3-N-acetylglucosaminyltransferase 5 |
| SLCO2A1 | 3.57 | 2.32 | 2.14 | solute carrier organic anion transporter family, member 2A1 |
| SLC35F3 | 3.55 | 3.21 | 3.38 | solute carrier family 35, member F3 |
| SOX5 | 3.55 | 4.09 | 3.99 | SRY (sex determining region Y)-box 5 |
| NUDT4P1 | 3.54 | 2.88 | 2.42 | nudix (nucleoside diphosphate linked moiety X)-type motif 4 pseudogene 1 |
| ANGPT2 | 3.54 | 5.23 | 3.90 | angiopoietin 2 |
| CAP2 | 3.53 | 2.97 | 3.00 | CAP, adenylate cyclase-associated protein, 2 (yeast) |
| NETO2 | 3.50 | 2.25 | 2.21 | neuropilin (NRP) and tolloid (TLL)-like 2 |
| TRY6\|PRSS2\|PRSS1\|PRSS3\|LOC100134294 | 3.50 | 3.12 | 3.59 | trypsinogen C\|protease, serine, 2 (trypsin 2)\|protease, serine, 1 (trypsin 1)\|protease, serine, 3\|hypothetical protein LOC100134294 |
| ANGPT1 | 3.49 | 3.56 | 3.37 | angiopoietin 1 |
| VANGL1 | 3.48 | 2.94 | 2.79 | vang-like 1 (van gogh, Drosophila) |
| CDA | 3.48 | 4.14 | 3.63 | cytidine deaminase |
| MCF2L2 | 3.46 | 3.33 | 3.11 | MCF.2 cell line derived transforming sequence-like 2 |
| C9ORF95 | 3.44 | 2.28 | 2.13 | chromosome 9 open reading frame 95 |
| GATA4 | 3.42 | 2.89 | 2.77 | GATA binding protein 4 |
| MAGI3 | 3.39 | 3.20 | 3.13 | membrane associated guanylate kinase, WW and PDZ domain containing 3 |
| WNT3 | 3.39 | 2.97 | 3.36 | wingless-type MMTV integration site family, member 3 |
| APOBEC3G\|APOBEC3F | 3.36 | 2.79 | 2.90 | apolipoprotein B mRNA editing enzyme, catalytic polypeptide-like 3G\|apolipoprotein B mRNA editing enzyme, catalytic polypeptide-like 3F |
| FOXA2 | 3.36 | 3.08 | 3.93 | forkhead box A2 |
| BRDT | 3.34 | 2.82 | 2.33 | bromodomain, testis-specific |
| TCAG7.1177 | 3.33 | 2.60 | 3.10 | opposite strand transcription unit to STAG3 |
| LOC389523\|LOC729438\|LOC730322 | 3.33 | 2.59 | 3.10 | similar to opposite strand transcription unit to Stag3 |
| ZSWIM5 | 3.32 | 2.79 | 2.75 | zinc finger, SWIM-type containing 5 |
| COCH | 3.32 | 2.08 | 2.53 | coagulation factor C homolog, cochlin (Limulus polyphemus) |
| EPHA4 | 3.31 | 4.54 | 4.66 | EPH receptor A4 |
| C1ORF61 | 3.30 | 3.51 | 3.49 | chromosome 1 open reading frame 61 |
| KEL | 3.29 | 4.02 | 4.07 | Kell blood group, metallo-endopeptidase |
| PPM1K | 3.29 | 3.71 | 3.74 | protein phosphatase 1K (PP2C domain containing) |
| SORCS1 | 3.29 | 3.64 | 4.01 | sortilin-related VPS10 domain containing receptor 1 |
| SLC46A3 | 3.28 | 2.01 | 2.00 | solute carrier family 46, member 3 |
| BHLHB2 | 3.23 | 2.26 | 2.43 | basic helix-loop-helix domain containing, class B, 2 |
| BMPR2 | 3.23 | 3.64 | 3.57 | bone morphogenetic protein receptor, type II (serine/threonine kinase) |

TABLE 2-continued

Variations of Transcript levels (2-fold or more) during DE formation in hESC-H9 and iPSC lines 3.12, 3.5 and 3.6

| GENE SYMBOL | DIFF'D-H9] vs [UNDIFF'D-H9] (folds) | [DIFF'D-IPSC3.12] vs [UNDIFF'D-IPSC3.12] (folds) | [Diff'd-iPSC3.4] vs [Undiff'd-iPSC3.4] (folds) | GENE DESCRIPTION |
|---|---|---|---|---|
| CAMKK2 | 3.21 | 2.94 | 3.14 | calcium/calmodulin-dependent protein kinase kinase 2, beta |
| DAB2 | 3.21 | 2.38 | 2.30 | disabled homolog 2, mitogen-responsive phosphoprotein (Drosophila) |
| ELMO1 | 3.20 | 5.68 | 4.76 | engulfment and cell motility 1 |
| SEMA6D | 3.20 | 6.82 | 6.05 | sema domain, transmembrane domain (TM), and cytoplasmic domain, (semaphorin) 6D |
| CXCR7 | 3.20 | 3.18 | 3.21 | chemokine (C—X—C motif) receptor 7 |
| P4HA1 | 3.20 | 2.63 | 2.45 | procollagen-proline, 2-oxoglutarate 4-dioxygenase (proline 4-hydroxylase), alpha polypeptide I |
| YAF2 | 3.17 | 2.48 | 2.87 | YY1 associated factor 2 |
| TMOD1 | 3.16 | 2.61 | 2.62 | tropomodulin 1 |
| RALB | 3.16 | 2.41 | 2.11 | v-ral simian leukemia viral oncogene homolog B (ras related; GTP binding protein) |
| FBN2 | 3.13 | 3.58 | 4.30 | fibrillin 2 (congenital contractural arachnodactyly) |
| KIAA1161 | 3.10 | 2.84 | 3.74 | |
| LTB4DH | 3.10 | 3.08 | 2.77 | leukotriene B4 12-hydroxydehydrogenase |
| DUSP4 | 3.10 | 3.14 | 2.43 | dual specificity phosphatase 4 |
| GPR39 | 3.09 | 5.74 | 6.56 | G protein-coupled receptor 39 |
| CNTN4 | 3.08 | 2.58 | 2.54 | contactin 4 |
| FRRS1 | 3.06 | 2.21 | 2.07 | ferric-chelate reductase 1 |
| PGM1 | 3.03 | 2.67 | 2.67 | phosphoglucomutase 1 |
| PDK1 | 3.03 | 4.84 | 5.36 | pyruvate dehydrogenase kinase, isozyme 1 |
| SOAT1 | 3.03 | 3.19 | 2.88 | sterol O-acyltransferase (acyl-Coenzyme A: cholesterol acyltransferase) 1 |
| CCDC92 | 3.00 | 2.79 | 2.97 | coiled-coil domain containing 92 |
| ZNF792 | 3.00 | 2.44 | 2.22 | zinc finger protein 792 |
| SLC35A3 | 3.00 | 3.55 | 2.83 | solute carrier family 35 (UDP-N-acetylglucosamine (UDP-GlcNAc) transporter), member A3 |
| SMAD7 | 3.00 | 2.23 | 2.07 | SMAD family member 7 |
| CEP55 | 2.99 | 2.02 | 2.08 | centrosomal protein 55 kDa |
| DDAH2 | 2.99 | 2.14 | 2.44 | dimethylarginine dimethylaminohydrolase 2 |
| DDAH2 | 2.98 | 2.15 | 2.44 | dimethylarginine dimethylaminohydrolase 2 |
| APOC1 | 2.97 | 2.73 | 2.14 | apolipoprotein C-I |
| TMEM133 | 2.95 | 3.63 | 3.12 | transmembrane protein 133 |
| HNF1B | 2.95 | 2.25 | 2.64 | HNF1 homeobox B |
| FLJ32810 | 2.94 | 3.55 | 2.92 | |
| RAP1GDS1 | 2.91 | 2.27 | 2.38 | RAP1, GTP-GDP dissociation stimulator 1 |
| DDAH2 | 2.90 | 2.08 | 2.29 | dimethylarginine dimethylaminohydrolase 2 |
| C5ORF36 | 2.90 | 2.59 | 2.45 | chromosome 5 open reading frame 36 |
| GCNT1 | 2.89 | 4.78 | 5.38 | glucosaminyl (N-acetyl) transferase 1, core 2 (beta-1,6-N-acetylglucosaminyltransferase) |
| APOBEC3D | 2.89 | 2.21 | 2.03 | apolipoprotein B mRNA editing enzyme, catalytic polypeptide-like 3D |
| NPPB | 2.88 | 3.62 | 3.57 | natriuretic peptide precursor B |
| MLYCD | 2.87 | 2.89 | 2.78 | malonyl-CoA decarboxylase |
| AADAT | 2.86 | 2.49 | 2.25 | aminoadipate aminotransferase |
| STMN2 | 2.85 | 5.88 | 5.04 | stathmin-like 2 |
| SULF2 | 2.85 | 3.19 | 2.99 | sulfatase 2 |
| ANKRD6 | 2.84 | 3.01 | 3.06 | ankyrin repeat domain 6 |
| TBX3 | 2.84 | 2.18 | 2.16 | T-box 3 (ulnar mammary syndrome) |
| APOA2 | 2.83 | 3.62 | 3.42 | apolipoprotein A-II |
| PPFIBP1 | 2.83 | 2.60 | 2.45 | PTPRF interacting protein, binding protein 1 (liprin beta 1) |
| ALDH1A1 | 2.82 | 2.46 | 2.18 | aldehyde dehydrogenase 1 family, member A1 |

TABLE 2-continued

Variations of Transcript levels (2-fold or more) during DE formation in hESC-H9 and iPSC lines 3.12, 3.5 and 3.6

| GENE SYMBOL | DIFF'D-H9] vs [UNDIFF'D-H9] (folds) | [DIFF'D-IPSC3.12] vs [UNDIFF'D-IPSC3.12] (folds) | [Diff'd-iPSC3.4] vs [Undiff'd-iPSC3.4] (folds) | GENE DESCRIPTION |
|---|---|---|---|---|
| LIFR | 2.82 | 2.31 | 2.51 | leukemia inhibitory factor receptor alpha |
| ID1 | 2.81 | 2.49 | 2.73 | inhibitor of DNA binding 1, dominant negative helix-loop-helix protein |
| MTUS1 | 2.81 | 2.72 | 2.99 | mitochondrial tumor suppressor 1 |
| MYL4 | 2.80 | 2.45 | 2.05 | myosin, light chain 4, alkali; atrial, embryonic |
| YPEL2 | 2.80 | 2.68 | 2.30 | yippee-like 2 (Drosophila) |
| FZD5 | 2.80 | 6.24 | 5.60 | frizzled homolog 5 (Drosophila) |
| TNNC1 | 2.80 | 2.31 | 2.03 | troponin C type 1 (slow) |
| TMPRSS11E\|TMPRSS11E2 | 2.79 | 3.23 | 3.04 | transmembrane protease, serine 11E\|transmembrane protease, serine 11E2 |
| CCDC75 | 2.78 | 2.47 | 2.15 | coiled-coil domain containing 75 |
| EGF | 2.78 | 4.20 | 3.94 | epidermal growth factor (beta-urogastrone) |
| KIT | 2.78 | 4.03 | 3.60 | v-kit Hardy-Zuckerman 4 feline sarcoma viral oncogene homolog |
| TMPRSS11E\|TMPRSS11E2 | 2.76 | 3.23 | 2.97 | transmembrane protease, serine 11E\|transmembrane protease, serine 11E2 |
| KCNG1 | 2.72 | 2.33 | 2.68 | potassium voltage-gated channel, subfamily G, member 1 |
| CUGBP2 | 2.72 | 2.54 | 2.11 | CUG triplet repeat, RNA binding protein 2 |
| CDH10 | 2.71 | 3.23 | 4.02 | cadherin 10, type 2 (T2-cadherin) |
| LEFTY1 | 2.70 | 4.86 | 5.04 | left-right determination factor 1 |
| C20ORF95 | 2.68 | 3.26 | 3.35 | chromosome 20 open reading frame 95 |
| ACSS3 | 2.67 | 2.12 | 2.10 | acyl-CoA synthetase short-chain family member 3 |
| FAM126B | 2.67 | 2.27 | 2.00 | family with sequence similarity 126, member B |
| PERP | 2.66 | 2.40 | 2.73 | |
| GATA6 | 2.65 | 3.93 | 4.05 | GATA binding protein 6 |
| ANKS1B | 2.64 | 2.39 | 2.26 | ankyrin repeat and sterile alpha motif domain containing 1B |
| CA2 | 2.61 | 2.48 | 2.36 | carbonic anhydrase II |
| TMEM135 | 2.58 | 2.71 | 2.72 | transmembrane protein 135 |
| CCDC3 | 2.58 | 2.68 | 2.84 | coiled-coil domain containing 3 |
| JAKMIP1 | 2.57 | 2.02 | 2.07 | janus kinase and microtubule interacting protein 1 |
| APOBEC3C\|APOBEC3D | 2.55 | 2.40 | 2.44 | apolipoprotein B mRNA editing enzyme, catalytic polypeptide-like 3C\|apolipoprotein B mRNA editing enzyme, catalytic polypeptide-like 3D |
| FZD8 | 2.54 | 3.57 | 3.26 | frizzled homolog 8 (Drosophila) |
| SYNJ1 | 2.54 | 2.43 | 2.33 | synaptojanin 1 |
| GATA3 | 2.54 | 2.04 | 2.15 | GATA binding protein 3 |
| QPCT | 2.53 | 3.59 | 3.29 | glutaminyl-peptide cyclotransferase (glutaminyl cyclase) |
| C8ORF79 | 2.52 | 2.17 | 2.90 | chromosome 8 open reading frame 79 |
| ZNF702 | 2.52 | 2.41 | 2.01 | zinc finger protein 702 |
| EDNRA | 2.52 | 2.69 | 2.27 | endothelin receptor type A |
| MAGED1 | 2.51 | 2.89 | 2.99 | melanoma antigen family D, 1 |
| DTWD2 | 2.50 | 2.53 | 2.32 | DTW domain containing 2 |
| KITLG | 2.48 | 2.12 | 2.82 | KIT ligand |
| APOBEC3F\|APOBEC3G | 2.48 | 2.48 | 2.29 | apolipoprotein B mRNA editing enzyme, catalytic polypeptide-like 3F\|apolipoprotein B mRNA editing enzyme, catalytic polypeptide-like 3G |
| ETS2 | 2.47 | 2.17 | 2.05 | v-ets erythroblastosis virus E26 oncogene homolog 2 (avian) |
| GNAL | 2.46 | 3.70 | 3.72 | guanine nucleotide binding protein (G protein), alpha activating activity polypeptide, olfactory type |
| ZNF518B | 2.45 | 3.00 | 2.39 | zinc finger protein 518B |
| HGSNAT | 2.45 | 2.95 | 2.90 | heparan-alpha-glucosaminide N-acetyltransferase |
| B4GALT4 | 2.42 | 2.12 | 2.05 | UDP-Gal:betaGlcNAc beta 1,4-galactosyltransferase, polypeptide 4 |

TABLE 2-continued

Variations of Transcript levels (2-fold or more) during DE formation in hESC-H9 and iPSC lines 3.12, 3.5 and 3.6

| GENE SYMBOL | DIFF'D-H9] vs [UNDIFF'D-H9] (folds) | [DIFF'D-IPSC3.12] vs [UNDIFF'D-IPSC3.12] (folds) | [Diff'd-iPSC3.4] vs [Undiff'd-iPSC3.4] (folds) | GENE DESCRIPTION |
|---|---|---|---|---|
| ATP8A1 | 2.42 | 2.91 | 2.77 | ATPase, aminophospholipid transporter (APLT), class I, type 8A, member 1 |
| SYT10 | 2.41 | 2.13 | 2.26 | synaptotagmin X |
| EFNA5 | 2.41 | 2.62 | 2.83 | ephrin-A5 |
| SMARCD3 | 2.40 | 2.70 | 2.39 | SWI/SNF related, matrix associated, actin dependent regulator of chromatin, subfamily d, member 3 |
| WDR44 | 2.40 | 2.48 | 2.26 | WD repeat domain 44 |
| EPHA2 | 2.39 | 2.03 | 2.12 | EPH receptor A2 |
| BCAR3 | 2.38 | 2.41 | 2.31 | breast cancer anti-estrogen resistance 3 |
| UNC50 | 2.36 | 3.44 | 3.34 | unc-50 homolog (*C. elegans*) |
| LY6E | 2.36 | 2.35 | 2.14 | lymphocyte antigen 6 complex, locus E |
| SLC5A9 | 2.34 | 7.86 | 6.18 | solute carrier family 5 (sodium/glucose cotransporter), member 9 |
| COL4A1 | 2.33 | 2.20 | 2.15 | collagen, type IV, alpha 1 |
| KIAA0825 | 2.32 | 2.72 | 2.49 | |
| NSUN3 | 2.32 | 2.41 | 2.15 | NOL1/NOP2/Sun domain family, member 3 |
| HEBP2 | 2.32 | 2.58 | 2.45 | heme binding protein 2 |
| COL6A1 | 2.32 | 2.20 | 2.52 | collagen, type VI, alpha 1 |
| PMEPA1 | 2.31 | 2.35 | 2.24 | prostate transmembrane protein, androgen induced 1 |
| STC1 | 2.30 | 2.94 | 3.30 | stanniocalcin 1 |
| MBNL3 | 2.29 | 2.65 | 2.47 | muscleblind-like 3 (*Drosophila*) |
| FST | 2.29 | 2.59 | 2.99 | follistatin |
| TNRC18| LOC27320 | 2.28 | 2.09 | 2.17 | trinucleotide repeat containing 18| hypothetical protein LOC27320 |
| LRRC3 | 2.25 | 2.18 | 2.53 | leucine rich repeat containing 3 |
| INPP4A | 2.25 | 2.50 | 2.55 | inositol polyphosphate-4-phosphatase, type I, 107 kDa |
| RRAGB | 2.25 | 2.26 | 2.21 | Ras-related GTP binding B |
| SLC9A9 | 2.25 | 2.70 | 3.10 | solute carrier family 9 (sodium/hydrogen exchanger), member 9 |
| TMEM123 | 2.25 | 2.26 | 2.27 | transmembrane protein 123 |
| GPR151 | 2.24 | 5.25 | 4.07 | G protein-coupled receptor 151 |
| NR3C1 | 2.24 | 2.58 | 2.64 | nuclear receptor subfamily 3, group C, member 1 (glucocorticoid receptor) |
| FAM89A | 2.22 | 2.14 | 2.32 | family with sequence similarity 89, member A |
| SHISA3 | 2.21 | 3.03 | 2.52 | shisa homolog 3 (*Xenopus laevis*) |
| GLT1D1 | 2.21 | 2.71 | 2.37 | glycosyltransferase 1 domain containing 1 |
| NRIP1 | 2.21 | 2.18 | 2.02 | nuclear receptor interacting protein 1 |
| WNT8A | 2.21 | 3.19 | 2.99 | wingless-type MMTV integration site family, member 8A |
| AKAP13 | 2.20 | 2.05 | 2.08 | A kinase (PRKA) anchor protein 13 |
| GPR37 | 2.20 | 2.36 | 2.53 | G protein-coupled receptor 37 (endothelin receptor type B-like) |
| COL4A6 | 2.19 | 2.76 | 3.25 | collagen, type IV, alpha 6 |
| DMN | 2.19 | 2.05 | 2.34 | desmuslin |
| PHF10 | 2.17 | 2.02 | 2.05 | PHD finger protein 10 |
| CCDC46 | 2.17 | 2.06 | 2.09 | coiled-coil domain containing 46 |
| TBX20 | 2.15 | 2.06 | 2.21 | T-box 20 |
| RCAN3 | 2.15 | 2.42 | 2.48 | RCAN family member 3 |
| ATP2B4 | 2.15 | 2.96 | 2.97 | ATPase, Ca++ transporting, plasma membrane 4 |
| FBXO34 | 2.15 | 2.05 | 2.19 | F-box protein 34 |
| C1ORF97 | 2.15 | 2.13 | 2.08 | chromosome 1 open reading frame 97 |
| MAPK10 | 2.14 | 2.59 | 2.41 | mitogen-activated protein kinase 10 |
| CCNG2 | 2.13 | 2.17 | 2.08 | cyclin G2 |
| CYP27A1 | 2.12 | 3.89 | 3.49 | cytochrome P450, family 27, subfamily A, polypeptide 1 |
| FUT8 | 2.12 | 3.09 | 2.80 | fucosyltransferase 8 (alpha (1,6) fucosyltransferase) |
| CTBS | 2.11 | 2.58 | 2.41 | chitobiase, di-N-acetyl- |
| ODZ4 | 2.10 | 2.46 | 2.76 | odz, odd Oz/ten-m homolog 4 (*Drosophila*) |

TABLE 2-continued

Variations of Transcript levels (2-fold or more) during DE formation in hESC-H9 and iPSC lines 3.12, 3.5 and 3.6

| GENE SYMBOL | DIFF'D-H9] vs [UNDIFF'D-H9] (folds) | [DIFF'D-IPSC3.12] vs [UNDIFF'D-IPSC3.12] (folds) | [Diff'd-iPSC3.4] vs [Undiff'd-iPSC3.4] (folds) | GENE DESCRIPTION |
|---|---|---|---|---|
| TRAF5 | 2.10 | 2.09 | 2.02 | TNF receptor-associated factor 5 |
| FZD4 | 2.09 | 2.40 | 2.63 | frizzled homolog 4 (*Drosophila*) |
| PCDH7 | 2.09 | 3.85 | 4.19 | protocadherin 7 |
| IL18R1 | 2.09 | 2.89 | 2.88 | interleukin 18 receptor 1 |
| PLXNA4 | 2.06 | 2.09 | 2.27 | plexin A4 |
| KCNK12 | 2.06 | 2.44 | 2.20 | potassium channel, subfamily K, member 12 |
| GPM6A | 2.04 | 5.17 | 5.20 | glycoprotein M6A |
| MAGED2 | 2.04 | 2.12 | 2.28 | melanoma antigen family D, 2 |
| PDGFC | 2.04 | 2.14 | 2.30 | platelet derived growth factor C |
| IFI16 | 2.03 | 4.18 | 3.33 | interferon, gamma-inducible protein 16 |
| ABCC4 | 2.03 | 3.31 | 2.93 | ATP-binding cassette, sub-family C (CFTR/MRP), member 4 |
| C4ORF35 | 2.02 | 2.19 | 2.01 | chromosome 4 open reading frame 35 |
| ELMOD2 | 2.01 | 2.42 | 2.07 | ELMO/CED-12 domain containing 2 |
| SH3RF1 | 2.01 | 2.35 | 2.34 | SH3 domain containing ring finger 1 |

Example 8

Tissue Processing, Immunohistochemistry and Microscopy

Tissues were fixed for 1 hour to overnight in 4% paraformaldehyde or 3% glutaraldehyde for transmission electron microscopy (TEM). Cultured PSCs and DE cells were stained directly. Hindgut and intestinal organoids were, embedded in paraffin, epoxy resin LX-112 (Ladd Research, Burlington, Vt.), or frozen in OCT. Sections were cut 6-10 micrometers for standard microscopy and 0.1 micrometers for TEM. TEM sections were stained with uranyl acetate. Parrafin sections were deparaffinized, subjected to antigen retrieval, blocked in the appropriate serum (5% serum in 1×PBS+0.5% triton-X) for 30 minutes, and incubated with primary antibody overnight at 4 degrees Celsius. Slides were washed and incubated in secondary antibody in blocking buffer for 2 hours at room temperature. For a list of antibodies used and dilutions, see Table 3A and 3B. Slides were washed and mounted using Fluormount-G. Confocal images were captured on a Zeiss LSM510 and Z-stacks were analyzed and assembled using AxioVision software. A Hitachi H7600 transmission electron microscope was used to capture images.

TABLE 3A

Primary Antibodies.

| PRIMARY ANTIBODY | SOURCE | DILUTION |
|---|---|---|
| Mouse anti-Phosphohistone H3 | Abcam | 1:500 |
| Rat anti-BrdU | Abcam | 1:500-1:1000 |
| Rabbit anti-Ki67 | Dako | 1:500 |
| Goat anti-Sox17 | R&D Systems | 1:500 |
| Mouse anti-FoxA2 | Novus Biologicals | 1:500 |
| Goat anti-Villin | Santa Cruz | 1:200-1:500 |
| Mouse anti-Cdx2 | BioGenex | 1:500 |
| Rabbit anti-ChromograninA | ImmunoStar | 1:1000 |
| Rabbit anti-Mucin (MUC2) | Santa Cruz | 1:200 |
| Rabbit anti-Lysozyme | Zymed Laboratories | 1:1000 |
| Rat anti-Klf5 | Dr. Ichiro Manabe | 1:2000 |
| Rabbit anti-Sox9 | Millipore | 1:1000 |
| Rabbit anti-Albumin | Sigma | 1:1000 |
| Rabbit anti-Laminin | Abcam | 1:500 |
| Mouse anti-E-Cadherin | BD Biosciences | 1:500 |
| Mouse anti-Smooth Muscle Actin | Millipore | 1:500 |
| Mouse anti-Neurogenin 3 | DSHB | 1:100 |
| Goat anti-Vimentin | Santa Cruz | 1:1000 |
| Goat anti-Pdx1 | Abcam | 1:5000 |
| Goat anti-Dpp4 | R&D Systems | 1:500 |
| Rabbit anti-Phosphohistone H3 | Cell Signaling | 1:500 |
| Goat anti-Gata4 | Santa Cruz | 1:200 |
| Rabbit anti-Gata6 | Santa Cruz | 1:200 |
| Rabbit anti-Nanog | Cosmo Bio. Co. | 1:2500 |
| Chicken anti-DNMT3b | Millipore | 1:1000 |
| Mouse anti-Tra 1-60 | Millipore | 1:500 |
| Mouse anti-Tra 1-81 | Millipore | 1:500 |

TABLE 3B

Secondary Antibodies.

| SECONDARY ANTIBODY | SOURCE | DILUTION |
|---|---|---|
| Goat anti-guinea pig Cy5 | Jackson Immuno | 1:500 |
| Goat anti-rabbit Cy5 | Jackson Immuno | 1:500 |
| Goat anti-rabbit Cy3 | Jackson Immuno | 1:500 |
| Goat anti-mouse Cy3 | Jackson Immuno | 1:500 |
| Goat anti-mouse 488 | Invitrogen | 1:500 |
| Goat anti-rabbit 488 | Invitrogen | 1:500 |
| Donkey anti-guinea pig Cy5 | Jackson Immuno | 1:500 |
| Donkey anti-rabbit Cy5 | Jackson Immuno | 1:500 |
| Donkey anti-rabbit Cy3 | Jackson Immuno | 1:500 |
| Donkey anti-mouse Cy3 | Jackson Immuno | 1:500 |
| Donkey anti-rabbit 488 | Invitrogen | 1:500 |
| Donkey anti-mouse 488 | Invitrogen | 1:500 |

Example 9

Adenovirus Production and Transduction

Adenoviral plasmids were obtained from Addgene and particles were generated according to the manufacturers protocol (Invitrogen—ViraPower Adenoviral Gateway Expression System) as previously described. 28 day organoids were removed from Matrigel and manually bisected with a scalpal. One half of each organoid was then incubated in Ad-GFP or Ad-Neurog3 viral supernatant and media at a 1:1 ratio for approximately 4 hours. Organoids were then re-embedded in Matrigel and incubated overnight with viral supernatant and media at a 1:1 ratio. The next day, fresh organoid media was placed on the cultures and was changed as described until the end of the experiment.

Adenoviral-Mediated Expression of NEUROG3.

Adenoviral plasmids were obtained from Addgene and particles were generated as previously described. Transduction was done on 28 day organoids that were removed from Matrigel, manually bisected then incubated in Ad-GFP or Ad-Neurog3 viral supernatant and media at a 1:1 ratio for approximately 4 hours. Organoids were then re-embedded in Matrigel and incubated overnight with viral supernatant and media at a 1:1 ratio, then transferred to fresh media until the end of the experiment.

More details can be found, for example, in Zhou et al., "In vivo reprogramming of adult pancreatic exocrine cells to beta-cells," *Nature* 455, 627-632 (2008); which is incorporated herein in its entirety.

Example 10

RNA Isolation, Reverse Transcription and Quantitative PCR (qPCR)

RNA was isolated using the Nucleospin II RNA isolation kit (Clonetech). Reverse Transcription was carried out using the SuperScriptIII Supermix (Invitrogen) according to manufacturers protocol. Finally, qPCR was carried out using Quantitect SybrGreen MasterMix (Qiagen) on a Chromo4 Real-Time PCR (BioRad). PCR primers sequences were typically obtained from qPrimerDepot (http://primerdepot<dot>nci<dot>nih<dot>gov/). Exemplary primers (SEQ ID NO.: 1-16 used can be found in the following Table 4.

Example 11

Regulation of Formation of Foregut and Hindgut from Human Embryonic and Induced Pluripotent Stem Cells Results and mechanisms for signaling network that regulates foregut, hindgut and intestinal development are shown in FIGS. 14-16. A summary of the pathways involved is shown in FIG. 14A.

Following definitive endoderm (DE) induction with activin (100 ng/ml) for 3 days, a 2-4 day treatment was performed with the indicated combination of factors: Wnt3a (500 ng/ml) and Fgf4 (500 ng/ml), Retinoic acid (RA) in a range of 0.2-20 µM the BMP antagonist Noggin (50 ng/ml), the WNT antagonist Dkk (1-500 ng/ml).

The Noggin completely abolishes the Wnt/Fgf-induced Cdx2 expression (FIG. 14B). Retinoic acid (2 µM) can posteriorize newly-formed definitive endoderm, especially in the first two days following DE induction. The Retinoic acid (RA)-induced posteriorization is also dependent on endogenous BMP signaling, as the addition of Noggin potently inhibits Cdx2 expression.

For investigating the impact of BMP signaling on intestinal regionalization after hindgut formation, hindgut spheroids were plated in matrigel and BMP or noggin were added to EGF/Rspondid1 containing media. Intestinal organoids were analyzed after 28 days.

It has been identified that, in addition to FGF and WNT signaling, BMP and RA signaling are capable of promoting a posterior/hindgut fate and repressing foregut fate. Additionally, BMP signaling regulates formation of distinct regional types of intestine. Inhibition of BMP with noggin after the hindgut stage promotes a proximal intestinal fate (duodenum/jejunum). Activation of BMP signaling after the hindgut stage promotes a more distal intestinal cell fate (cecum/colon).

FIGS. 14B-14D demonstrate the effects of FGF, WNT, and BMP signaling on differentiation of Definitive endo-

TABLE 4

Exemplary primers used.

| GENES | FORWARD PRIMERS | REVERSE PRIMERS |
|---|---|---|
| Beta-Tubulin | GATACCTCACCGTGGCTGCT (SEQ ID NO.: 1) | AGAGGAAAGGGGCAGTTGAGT (SEQ ID NO.: 2) |
| Pdx1 | CGTCCGCTTGTTCTCCTC (SEQ ID NO.: 3) | CCTTTCCCATGGATGAAGTC (SEQ ID NO.: 4) |
| Albumin | AACGCCAGTAAGTGACAGAGTC (SEQ ID NO.: 5) | AGGTCTCCTTATCGTCAGCCT (SEQ ID NO.: 6) |
| Cdx2 | GGGCTCTCTGAGAGGCAGGT (SEQ ID NO.: 7) | GGTGACGGTGGGGTTTAGCA (SEQ ID NO.: 8) |
| Sox9 | GTACCCGCACTTGCACAAC (SEQ ID NO.: 9) | GTGGTCCTTCTTGTGCTGC (SEQ ID NO.: 10) |
| Villin | CCAAAGGCCTGAGTGAAATC (SEQ ID NO.: 11) | CCTGGAGCAGCTAGTGAACA (SEQ ID NO.: 12) |
| Lysozyme | ACAAGCTACAGCATCAGCGA (SEQ ID NO.: 13) | GTAATGATGGCAAAACCCCA (SEQ ID NO.: 14) |
| HoxA13 | GCACCTTGGTATAAGGCACG (SEQ ID NO.: 15) | CCTCTGGAAGTCCACTCTGC (SEQ ID NO.: 16) | derm into foregut and hindgut. In particular, FIGS. 14B and 14D depict the activation of FGF/WNT/BMP signaling promotes posterior/hindgut fate as indicated by expression of Cdx2. Repression of BMP signaling with noggin suppresses hindgut fate and promotes foregut fate. Activation of FGF/WNT/BMP signaling represses foregut fate as indicated by expression of Sox2 (FIG. 14C). Repression of WNT signaling with Dkk promotes anterior gene expression (HHex and Cerberus) and represses posterior/hindgut fate (Cdx2) (FIG. 14D).

Figure 15A:
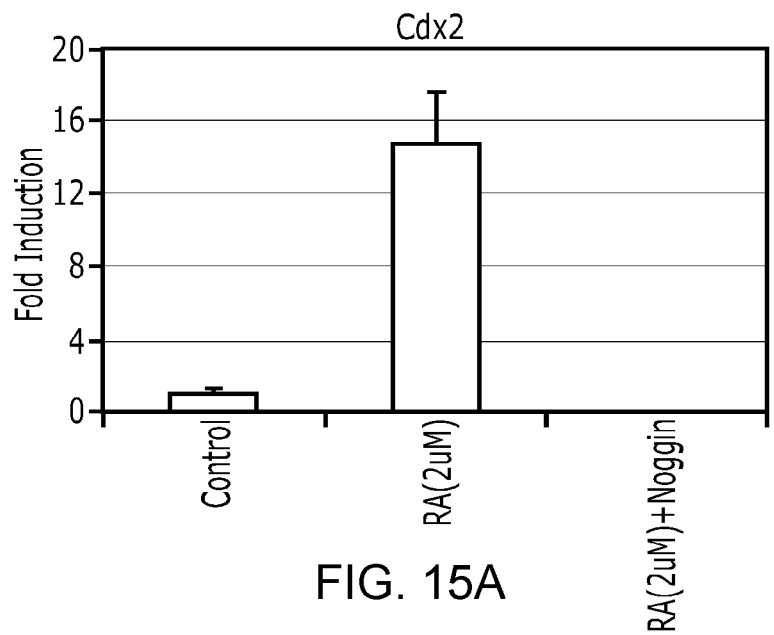
FIGS. 15A-15D illustrate exemplary embodiments in accordance with the present invention.
Figure 15B:
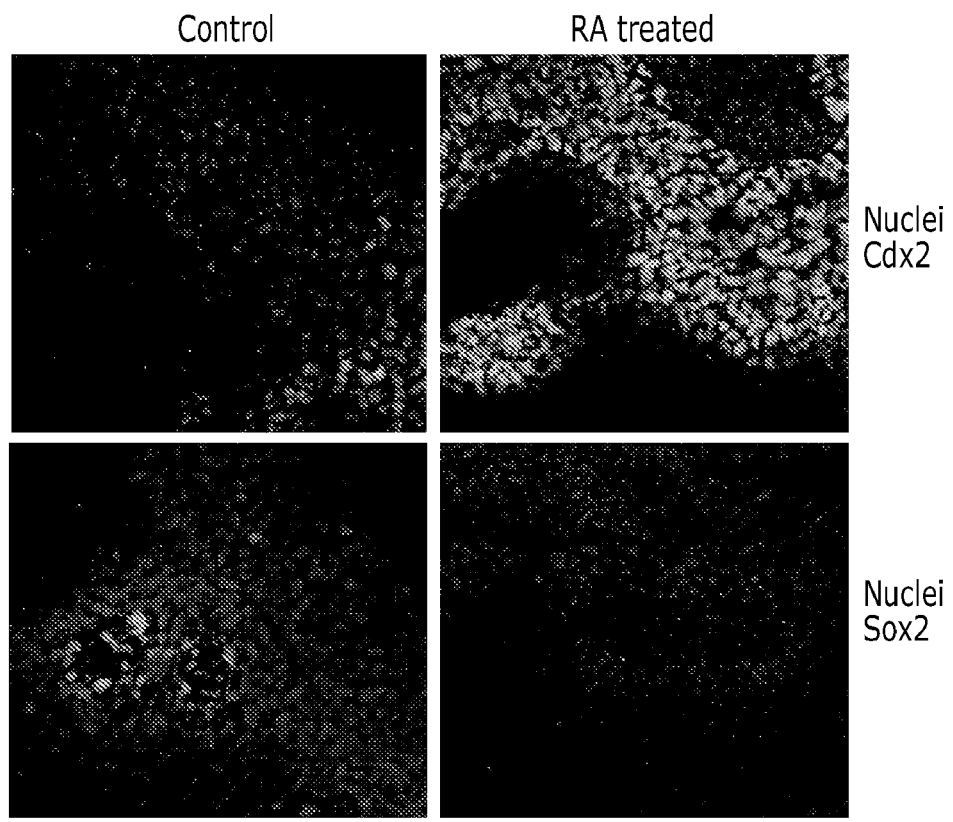
Figure 15C:
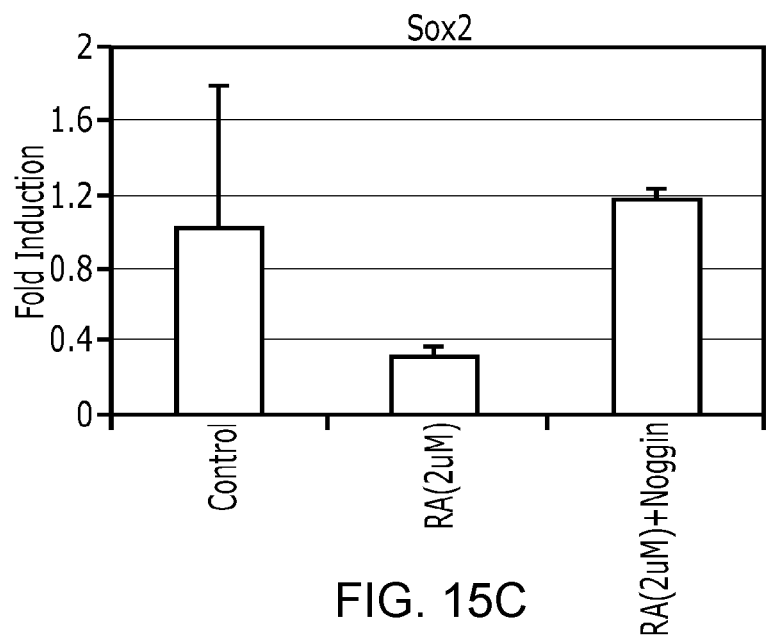
Figure 15D:
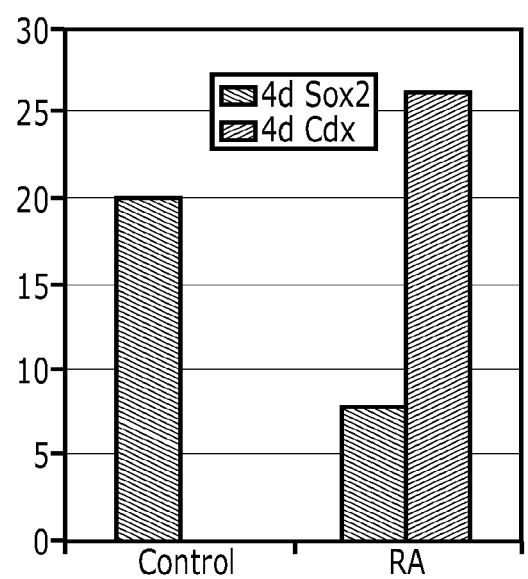

The effects of Retinoic Acid in promoting hindgut differentiation in a BMP dependent manner (FIGS. 15A-15D). Quantitative realtime PCR was used to compare the effects of Retinoic Acid and inhibition of BMP on differentiation of Definitive endoderm into foregut and hindgut (FIGS. 15A and 15B). Similar comparison was also performed by immunostaining (FIGS. 15C and 15D). Activation of RA signaling promotes posterior/hindgut fate as indicated by expression of Cdx2 and represses foregut fate as indicated by expression of Sox2. Immunostaining in FIG. 15C is quantified in FIG. 15D using an automated cell counting program.

Figure 16A:
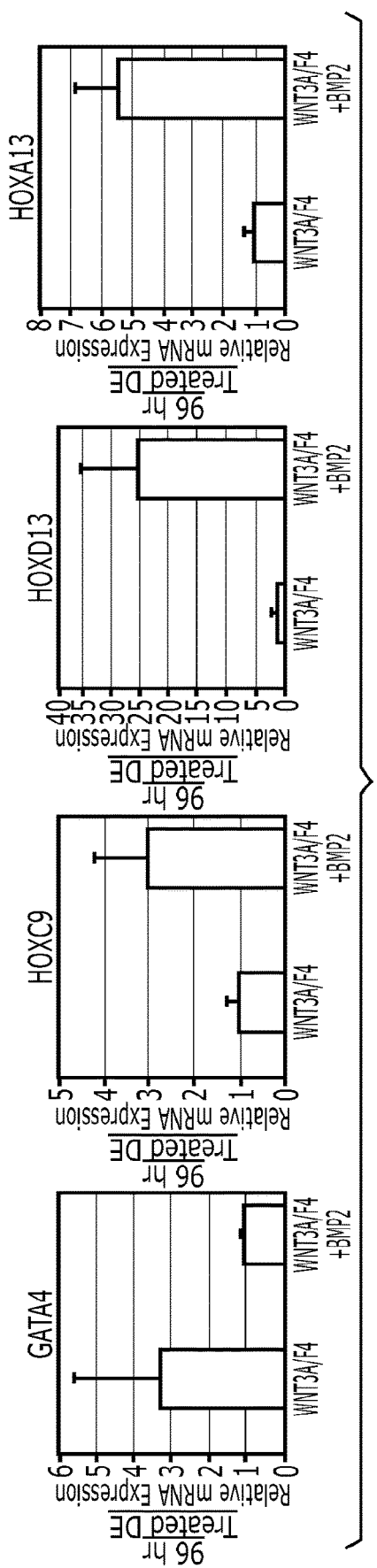
FIGS. 16A-16C illustrate exemplary embodiments in accordance with the present invention.
Figure 16B:
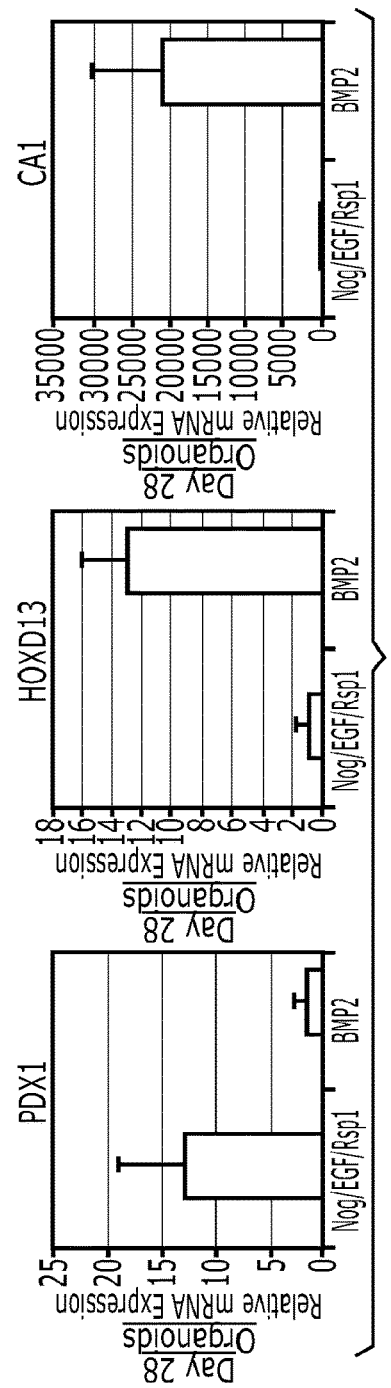
Figure 16C:
Figure 16C:

FIGS. 16A through 16C demonstrate that BMP signaling regulates formation of proximal and distal intestine formation from human embryonic and induced pluripotent stem cells. FIG. 16A shows that BMP2 promotes a posterior fate for monolayers when added during 96-hour WNT/FGF (W/F) treatment as shown by decreased expression of GATA4 compared to W/F alone and by increased expression of HOXC9 (distal small bowel and proximal colon), HOXD13, and HOXA13 compared to W/F alone.

FIG. 16B shows that, after formation of hindgut sphereoids, addition of BMP2 to 3D cultures promotes patterning of developing intestinal organoids to a distal fate after 28 days compared to the Nog/EGF/Rspo1 cocktail without BMP2 as shown by decreased relative expression of PDX1 and increased expression of HOXD13 and CA1 (carbonic anhydrase-colonocyte marker).

FIG. 16C shows that Day 138 Noggin/EGF/Rspondid1 treated organoids express CCK in the epithelium by immunostaining thus indicating a proximal small bowel fate.

FIGS. 14A-14D depict formation of foregut and hindgut from human embryonic and induced pluripotent stem cells is regulated by WNT, FGF, BMP and Retinoic acid (RA) signaling. A) Summary of the signaling network that regulates hindgut and intestinal development. B-D) Effects of FGF, WNT, and BMP signaling on differentiation of definitive endoderm into foregut and hindgut. B) and D). Activation of FGF/WNT/BMP signaling promotes posterior/hindgut fate as indicated by expression of Cdx2. Repression of BMP signaling with noggin suppresses hindgut fate and promotes foregut fate. C) Activation of FGF/WNT/BMP signaling represses foregut fate as indicated by expression of Sox2. D) Repression of WNT signaling with Dkk promotes anterior gene expression (HHex and Cerberus) and represses posterior/hindgut fate (Cdx2).

FIGS. 15A-15D depict retinoic acid promotes hindgut differentiation in a BMP dependent manner. Comparing the effects of Retinoic Acid and inhibition of BMP on differentiation of Definitive endoderm into foregut and hindgut by quantitative realtime PCR A) and B) or by immunostaining C) and D). Activation of RA signaling promotes posterior/hindgut fate as indicated by expression of Cdx2 and represses foregut fate as indicated by expression of Sox2. Immunostaining in C is quantified in D using an automated cell counting program.

FIGS. 16A-16C depict BMP signaling regulates formation of proximal and distal intestine formation from human embryonic and induced pluripotent stem cells. A) BMP2 promotes a posterior fate for monolayers when added during 96-hour WNT/FGF (W/F) treatment as shown by decreased expression of GATA4 compared to W/F alone and by increased expression of HOXC9 (distal small bowel and proximal colon), HOXD13, and HOXA13 compared to W/F alone. B) After formation of hindgut sphereoids, addition of BMP2 to 3D cultures promotes patterning of developing intestinal organoids to a distal fate after 28 days compared to the Nog/EGF/Rspo1 cocktail without BMP2 as shown by decreased relative expression of PDX1 and increased expression of HOXD13 and CA1 (carbonic anhydrase—colonocyte marker). C) Day 138 Noggin/EGF/Rspondid1 treated organoids express CCK in the epithelium by immunostaining thus indicating a proximal small bowel fate.

The various methods and techniques described above provide a number of exemplary ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof. Many variations and alternative elements have been disclosed in embodiments of the present invention. Still further variations and alternate elements will be apparent to one of skill in the art.

In some embodiments, the numbers expressing quantities of ingredients, properties such as molecular weight, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable.

The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Many modifications and variations of the present invention can be made without departing from its spirit and scope, as will be apparent to those skilled in the art. The specific embodiments described herein are offered by way of example only, and the invention is to be limited only by the terms of the appended claims along with the full scope of equivalents to which such claims are entitled.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

REFERENCES CITED

All references cited are incorporated herein by reference in their entireties and for all purposes to the same extent as if each individual publication or patent or patent application was specifically and individually indicated to be incorporated by reference in its entirety for all purposes.

What is claimed is:

1. A method of inducing formation of an organoid in vitro, wherein said organoid expresses CDX2, KLF5, and SOX9, comprising the steps of:
    a) contacting a population of definitive endoderm cells with an FGF signaling pathway activator and a Wnt signaling pathway activator until CDX2+ posterior definitive endoderm cells are obtained, wherein said posterior definitive endoderm cells maintain expression of CDX2 following removal of said FGF signaling pathway activator and said Wnt signaling pathway activator;
    b) culturing said posterior definitive endoderm cells of step (a) to obtain a 3-dimensional spheroid, wherein said 3-dimensional spheroid comprises a CDX2+ polarized epithelium and a CDX2+ mesenchyme; and
    c) contacting said 3-dimensional spheroid of step (b) with epidermal growth factor (EGF) until said organoid expressing CDX2, KLF5, and SOX9 is obtained.

2. The method of claim 1, wherein said Wnt signaling pathway activator is one or more molecules selected from Wnt1, Wnt2, Wnt2b, Wnt3, Wnt3a, Wnt4, Wnt5a, Wnt5b, Wnt6, Wnt7a, Wnt7b, Wnt8a, Wnt8b, Wnt9a, Wnt9b, Wnt10a, Wnt10b, Wnt11, Wnt16, Lithium Chloride; 2-amino-4,6-disubstituted pyrimidine (hetero) arylpyrimidines; IQ1; QS11; NSC668036; DCA beta-catenin; 2-amino-4-[3,4-(methylenedioxy)-benzyl -amino]-6-(3-methoxyphenyl) pyrimidine, and combinations thereof.

3. The method of claim 1, wherein said FGF signaling pathway activator is one or more molecules selected from FGF1, FGF2, FGF3, FGF4, FGF10, FGF11, FGF12, FGF13, FGF14, FGF15, FGF16, FGF17, FGF18, FGF19, FGF20, FGF21, FGF22, and FGF23.

4. The method of claim 1, wherein said FGF signaling pathway activator is FGF4 and said Wnt signaling pathway activator is Wnt3a.

5. The method of claim 4, wherein said definitive endoderm cell is contacted by Wnt3a during a first activation period and by FGF4 during a second activation period.

6. The method of claim 5, wherein said first activation period and said second activation period overlap.

7. The method of claim 5, wherein said first activation period and said second activation period do not overlap.

8. The method of claim 1, wherein said specified activation period is between 24 and 120 hours.

9. The method of claim 1, wherein said population of definitive endoderm cells is contacted with Wnt3a at a concentration between 50-1500 ng/ml.

10. The method of claim 1, wherein the definitive endoderm cell is derived from a mouse or human pluripotent stem cell.

11. The method of claim 10, wherein said pluripotent stem cell is an embryonic stem cell, an embryonic stem cell, or an induced pluripotent stem cell.

12. The method of claim 1, wherein said definitive endoderm cell is derived by contacting the pluripotent stem cell with one or more molecules selected from the group consisting of Activin, the BMP subgroups of the TGF-beta superfamily of growth factors; Nodal, Activin A, Activin B, BMP4, Wnt3a, and a combinations thereof.

13. The method of claim 10, wherein said pluripotent stem cell is a human pluripotent stem cell.

14. The method of claim 13, wherein said human pluripotent stem cell is selected from the group consisting of a human embryonic stem cell, a human embryonic germ cell, and an induced human pluripotent stem cell.

* * * * *